(12) United States Patent
Yamasaki et al.

(10) Patent No.: US 8,349,365 B2
(45) Date of Patent: Jan. 8, 2013

(54) CELLOOLIGOSACCHARIDE-CONTAINING COMPOSITION

(75) Inventors: Naoaki Yamasaki, Tokyo (JP); Ichiro Ibuki, Tokyo (JP); Yoshihito Yaginuma, Tokyo (JP); Yoshinaga Tamura, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 1120 days.

(21) Appl. No.: 12/088,218

(22) PCT Filed: Sep. 27, 2006

(86) PCT No.: PCT/JP2006/319119
§ 371 (c)(1),
(2), (4) Date: Sep. 16, 2008

(87) PCT Pub. No.: WO2007/037249
PCT Pub. Date: Apr. 5, 2007

(65) Prior Publication Data
US 2009/0232892 A1    Sep. 17, 2009

(30) Foreign Application Priority Data
Sep. 27, 2005    (JP) .................................. 2005-279157

(51) Int. Cl.
*A61K 9/14*    (2006.01)
(52) U.S. Cl. ...................................... 424/489
(58) Field of Classification Search ........................ None
See application file for complete search history.

(56) References Cited

U.S. PATENT DOCUMENTS

| | | | |
|---|---|---|---|
| 4,908,311 | A | 3/1990 | Sasaki et al. |
| 5,219,842 | A | 6/1993 | Okada et al. |
| 6,482,429 | B1 | 11/2002 | Etzler |
| 6,861,077 | B1 | 3/2005 | Cannell et al. |
| 2004/0053887 | A1 | 3/2004 | Obae et al. |

FOREIGN PATENT DOCUMENTS

| | | | |
|---|---|---|---|
| EP | 415720 A2 | * | 3/1991 |
| JP | 62-273921 | | 11/1987 |
| JP | 1-256394 | | 10/1989 |
| JP | 3-262460 | | 11/1991 |
| JP | 6-116162 | | 4/1994 |
| JP | 7-138166 | | 5/1995 |
| JP | 07184678 A | * | 7/1995 |
| JP | 7-252156 | | 10/1995 |
| JP | 8-73368 | | 3/1996 |

(Continued)

OTHER PUBLICATIONS

English translation of Digestibility, Absorptivity and Physiological Effects of Cellooligosaccharides in Human and Rat, Journal of Japanese Society of Nutrition and Food Sciences, 1996, 49, 143-148.*
Machine translation of JP 07184678 A, Jan. 2012.*
Satouchi et al., "Digestibility, Absorptivity and Physiological Effects of Cellooligosaccharides in Human and Rat," Journal of Japanese Society of Nutrition and Food Science, 1996, vol. 49, No. 3, p. 143-148.
Nakamura et al., "Bioavailability of cellobiose by tolerance test and breath hydrogen excretion in humans," Nutrition, vol. 20, p. 979-983, 2004.

(Continued)

*Primary Examiner* — Paul Dickinson
(74) *Attorney, Agent, or Firm* — Morgan, Lewis & Bockius LLP

(57) ABSTRACT

Disclosed is a cellooligosaccharide composition comprising, as the main ingredient, at least one cellooligosaccharide selected from the group consisting of cellobiose, cellotriose, cellotetraose, cellopentaose and cellohexaose, which is in the powdery form having an average L/D value of 3.0 or lower, a bulk density of 0.80 g/mL or lower and an angle of repose of 60° or lower.

30 Claims, 1 Drawing Sheet

FOREIGN PATENT DOCUMENTS

| | | |
|---|---|---|
| JP | 8-73372 | 3/1996 |
| JP | 11-43443 | 2/1999 |
| JP | 11-80781 | 3/1999 |
| JP | 11-279049 | 10/1999 |
| JP | 11-279076 | 10/1999 |
| JP | 2001-226280 | 8/2001 |
| JP | 2002-348248 | 12/2002 |
| JP | 2003-526646 | 9/2003 |
| JP | 2004-321068 | 11/2004 |
| JP | 2005-89355 | 4/2005 |
| JP | 2005-139075 | 6/2005 |
| JP | 2005-232260 A | 9/2005 |
| JP | 2006-45186 | 2/2006 |
| JP | 1-225457 | 9/2008 |
| WO | 02/02643 A1 | 1/2002 |

OTHER PUBLICATIONS

"New Technologies of Wood Chemicals," CMC Publishing Co., Ltd., p. 66-72, 2000, with partial English transation.

"Development of physiological functions of cellooligosaccharides," Cellulose Communications, vol. 5, No. 2, p. 91-97, 1998.

"Advancement and future prospect of evaluation techniques for usefulness of cosmetics technologies," Yakuji Nippo Limited, p. 82-101, 2001, partial English translation.

"Functional cosmetics," Japan Cosmetics Science Association Ed., JISC, p. 232-252, 1991, partial English translation.

Supplementary European Search Report for European Patent Application No. EP 06 81 0610 dated Jan. 4, 2012.

* cited by examiner

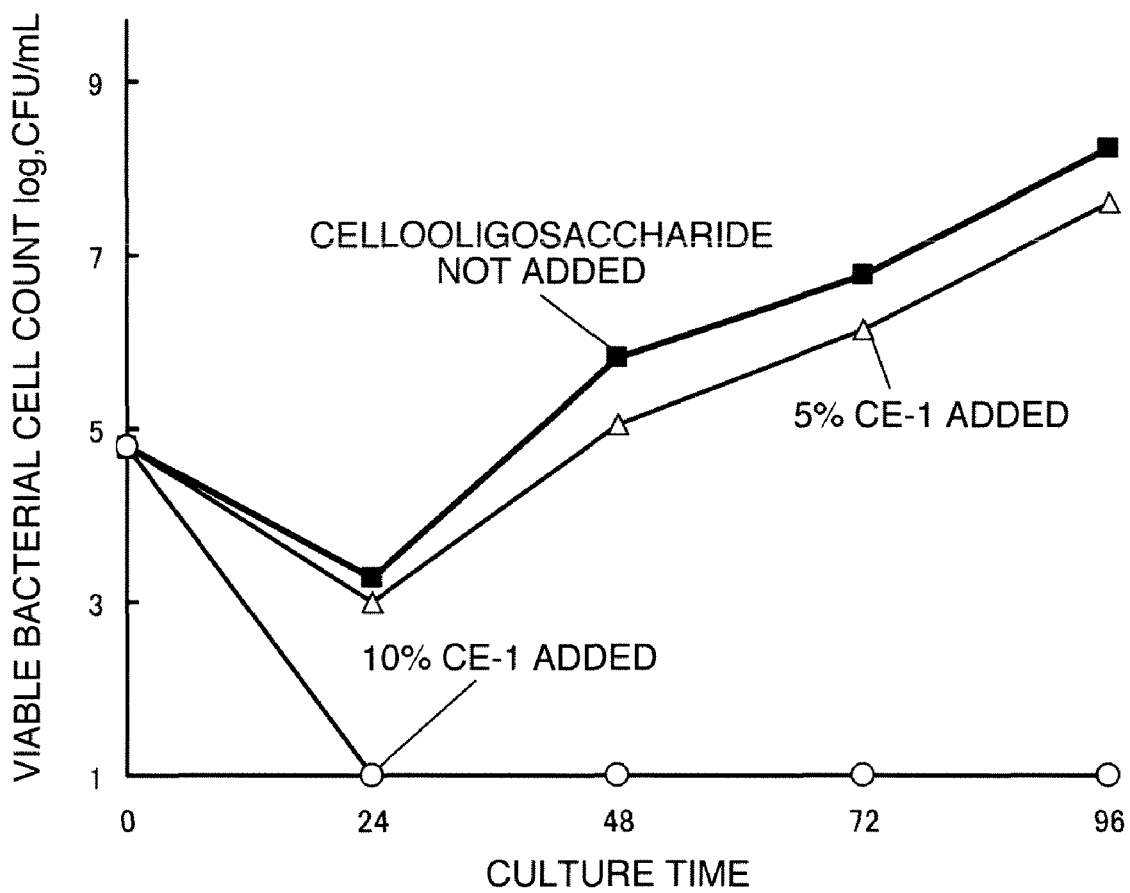

CELLOOLIGOSACCHARIDE-CONTAINING COMPOSITION

The present application is a U.S. National Phase Application of International Application No. PCT/JP2006/319119 (filed Sep. 27, 2006) which claims the benefit of Japanese Patent Application No. 2005-279157 (filed Sep. 27, 2005), both of which are hereby incorporated by reference in their entireties.

TECHNICAL FIELD

The present invention provides a cellooligosaccharide-containing composition for prevention or improvement of lifestyle-related diseases in the fields of foods and internal medicines, wherein the cellooligosaccharide-containing composition decreases neutral fat and total cholesterol concentrations in the liver by oral intake thereof because it comprises a cellooligosaccharide which has a regulated saccharide composition and suppresses a decrease of a blood adiponectin concentration. The present invention also provides a cellooligosaccharide-containing composition with a property of activating enteric bacteria that is not assimilated by harmful intestinal bacteria and selectively activates useful bacteria. The present invention also provides a cellooligosaccharide-containing composition suppressing *Helicobacter pylori* by suppressing propagation of *Helicobacter pylori* or by a bacteriostatic effect against *Helicobacter pylori*.

Furthermore, the present invention provides a cellooligosaccharide-containing composition for improving a ski barrier function in the fields of cosmetics, drugs, and quasi-drugs, as a topical agent that has an excellent Moistening effect for improving damaged skin such as rough skin, sensitive skin and dry skin, promotes recovery of transepidermal water loss, and has favorable usability and excellent handling properties. The present invention also provides a cellooligosaccharide-containing composition for improving indigenous dermal bacteria flora that is not assimilated by harmful epidermal bacteria and selectively activates useful bacteria.

Furthermore, in the fields of foods, cosmetics, drugs, and quasi-drugs, the present invention provides a high fluidity cellooligosaccharide powder which is excellent in oil retention in addition to powder fluidity and uniform dispersibility; hardly absorbs moisture; and is excellent in handling properties such as a compression moldability, heat resistance, acid resistance, a property of preventing starch retrogradation, and a property of preventing protein modification with regard to a high fluidity cellooligosaccharide powder and a composition comprising this cellooligosaccharide powder. The present invention also provides a food, a cosmetic, a drug, or a quasi-drug. Cellooligosaccharide therein are not agglutinated; dispersivity thereof is improved; excellent compression moldability, heat resistance, and acid resistance are imparted thereto; and starch retrogradation and protein modification thereof are prevented by comprising the high fluidity cellooligosaccharide powder.

BACKGROUND ART

Cellooligosaccharide is a generic name for cellobiose, cellotriose, cellotetraose, cellopentaose, and cellohexaose and is an oligosaccharide with 1 to 6 glucopyranose units linked by a β-1,4 bond in one molecule.

In the present specification, a composition containing other components, for example, glucose in addition to these cellooligosaccharides is referred to as a "cellooligosaccharide composition."

Furthermore, in the present specification, a composition that comprises this "cellooligosaccharide composition" as an active ingredient and may contain other additives or the like is referred to as a "cellooligosaccharide-containing composition" or "drug composition").

Cellooligosaccharide are hardly digested and absorbed by humans, and therefore, they are useful as low-calorie sweeteners. In addition, they are also useful as general foods, functional foods, cosmetics, drugs and additives hereof, other raw materials for chemical conversion, and raw materials for fermentation (Non-patent Document 1).

With a focus on lipids in the liver that can cause pathological conditions such as diabetes, arteriosclerosis, and cirrhosis in adults, the present invention can be used as an agent for preventing or improving a lifestyle-related disease because a composition comprising a cellooligosaccharide composition with a specific saccharide composition suppresses a decrease of a blood adiponectin concentration and decreases lipids in the liver.

Non-patent Document 2 discloses bioavailability of dietary intake calorie, blood sugar levels, blood insulin concentrations, and the like when healthy humans (females) ingest a cellooligosaccharide composition consisting of 92.9% of cellobiose, 3.3% of cellooligosaccharides with a degree of polymerization of 3 or higher, and 3.8% of glucose. In the document, only blood sugar levels and insulin concentrations were measured to confirm digestibility of the cellooligosaccharide composition, and the composition was only orally administered to humans to obtain exact dietary intake calories. Furthermore, the document includes no description or suggestion about the intake of the cellooligosaccharide composition and the neutral fat concentration in the liver. Therefore, the document is completely different from the cellooligosaccharide composition of the present invention, which has a specific saccharide composition and a low decreasing rate of blood adiponectin, and is used as an agent for preventing or improving a lifestyle-related disease since the composition is effective in decreasing the neutral fat concentration in the liver by oral intake thereof.

The following reports are available on the attempts to use cellooligosaccharides for lipid metabolization.

Non-patent Documents 1, 3, and 4 describe results after breeding SD male rats for 4 weeks by feeding a high sucrose diet (64.7 parts by mass of sucrose, 25 parts by mass of casein, 5 parts by mass of corn oil, 4 parts by mass of mineral, 1 part by mass of vitamins, 0.2 parts by mass of choline hydrochloride, and 0.05 parts by mass of vitamin E) of which 1 or 2.5% by mass was replaced with a cellooligosaccharide composition comprising 85.7% by mass of cellobiose, 3.7% by mass of cellotriose, and 9.3% by mass of glucose as a saccharide composition. According to the document, intake of the cellooligosaccharide composition having the above-mentioned saccharide composition decreased serum total cholesterol, HDL-cholesterol, and triglyceride levels and body fat rates as compared with a group without the cellooligosaccharide composition. However, although the cellooligosaccharide of the documents showed a decreasing effect of serum lipid, the weights of the internal organs such as a liver did not change. Furthermore, a decreasing effect of visceral lipid was not observed. On the other hand, the present invention provides an agent for preventing or improving a lifestyle-related disease that has a specific saccharide composition; suppresses a decrease of a blood adiponectin concentration; comprises a cellooligosaccharide composition; and has an excellent decreasing effect of lipid in the liver. Therefore, it is totally different from the cellooligosaccharide of the documents decreasing the serum lipid.

Furthermore, Patent Document 1 describes food/feed additives for regulating intestinal functions and promoting lipid metabolism which are characterized in that lactic bacteria cells (*Lactobacillus rhamnosus*) and cellobiose are contained in mixture ratios of 1:2.5 to 8. The document describes results after breeding male Wister rats for 14 days by feeding an elemental diet 20.0 parts by mass of casein, 0.3 parts by mass of DL-methionine, 3.5 parts by mass of minerals, 1.0 parts by mass of vitamins, 7.0 parts by mass of soybean oil) of which 10% by mass was replaced with cellobiose. According to the document, the group fed with diet containing cellobiose alone had no effect on serum or visceral lipid metabolism as compared with the group fed with diet not containing the same. The lipid levels were decreased only when cellobiose and the above-mentioned lactic bacterium were used in combination. Therefore, it is essentially different from an agent for preventing or improving a lifestyle-related disease such as the saccharide composition of the present invention, which comprises cellooligosaccharides having a highly regulated saccharide composition, and decreases fat levels in the liver by cellooligosaccharides alone. Furthermore, since the diet for promoting the lipid metabolism of the document requires simultaneous intake of cellobiose and viable bacterial cells, there is a problem that the effect thereof decreases to a considerable extent before use because of poor stability of viable bacterial cells in a formulation.

Therefore, there has been known no lifestyle-related disease preventing or improving agent which comprises, as an active ingredient, an Insulin-non-increasing cellooligosaccharide composition having a specific saccharide composition and suppressing a decrease in a blood adiponectin concentration and decreases lipids in the liver by taking the same.

Hereafter, activation of the enteric bacteria flora by the cellooligosaccharide composition of the present inanition or the cellooligosaccharide-containing composition of the present invention will be explained. In recent years, it has been revealed that the enteric bacteria flora is closely related to human health. For example, bifidobacteria, lactic bacteria and the like are useful bacteria that bring health to humans. Since they decrease with aging, attempts have been made to improve the enteric bacteria flora (intestinal flora) with functional foods such as prebiotics (served as nutrients for enteric bacteria and having a function to increase them). There are many existing functional foods that propagate bifidobacteria and lactic bacteria.

In particular, the above-mentioned prebiotics with a higher selective activity of activating only useful intestinal bacteria and not activating harmful bacteria are more efficient. Examples of the existing attempts include foods that activate useful bacteria while inhibiting propagation of *Clostridium perfringens*, a kind of a Welch *bacillus*, as harmful intestinal bacteria.

Among the above-described attempts of increasing bifidobacteria and lactic bacteria and suppressing Wench *bacillus*, those related to oligosaccharides with β bonds will be described below.

Patent Document 2 describes the substance for improving intestinal flora comprising glucoolroosaccharides having β-glucosidic bonds and/or a reduced product thereof as an active ingredient. The glucooligosaccharide described in the document is one or two or more types selected from cellobiose, sophorose, laminaribiose, gentiobiose, and gentiooligosyl-D-glucose. This oligosaccharide undoubtedly promotes propagation of useful bacteria such as bifidobacteria and lactic bacteria and has an effect of suppressing propagation of Welch *bacillus*.

However, there was a problem that harmful bacteria other than Welch *bacillus* such as *Bacteroides* fragilis and *Eubacterium aerofaciens* were increased to a considerable extent. *Bacteroides fragilis* and *Eubacterium aerofaciens* are anaerobic asporogenic Gram-negative *bacillus* which are harmful bacteria relating to various abscess forming infections and bacteremia caused by the mixed infection thereof with aerobic bacteria. The agent for improving intestinal flora of the above-mentioned document is totally different from the present invention of an agent for activating enteric bacteria which can propagate useful bacteria such as bifidobacteria and lactic bacteria and suppressing propagation of harmful bacteria such as *Bacteroides fragrlis* and *Eubacterium aerofaciens*. Therefore, there has been known no agent for activating enteric bacteria that has a regulated saccharide composition of cellooligosaccharides in a specific range; propagates useful bacteria such as bifidobacteria and lactic bacteria; and suppresses propagation of harmful bacteria such as *Bacteroides fragailis* and *Eubacterium aerofaciens.*

Hereafter, suppression of propagation of *Helicobacter pylori* or a bacteriostatic effect against *Helicobacter pylori* by the cellooligosaccharide composition or the cellooligosaccharide-containing composition of the present invention will be described. *Helicobacter pylori* is a microaerobic Gram-negative *bacillus*. *Helicobacter pylori* is thought to live in a strongly acidic environment in the stomach by producing ammonia from urea by the urease activity thereof to neutralize the gastric acid. It has been revealed that this ammonia produced by *Helicobacter pylori* damages the stomach mucous membrane and it is associated with stomach diseases such as gastritis, ulcer, stomach cancer, and lymphoma. It is recognized that suppression or regulation of the growth of *Helicobacter pylori* is an effective method for prevention or improvement of these diseases.

As a conventional method for suppressing *Helicobacter pylori*, administration of antibiotics has been attempted. This method undoubtedly has an effect of suppressing *Helicobacter pylori*. However, there was also a problem that the suppressing actions of the antibiotics affected not only *Helicobacter pylori*, but also enteric bacteria which are useful for the human body. Furthermore, there was also a problem that the antibiotics had no small effects on the human body such as causing diarrhea as the adverse drug reaction. Therefore, a suppressing agent that is safe to the human body and acts selectively on *Helicobacter pylori* has been desired. As prior art, examples of the agent for suppressing *Helicobacter pylori* comprising a saccharide as an active ingredient include the following.

Patent Document 3 discloses an antitumor agent comprising fucoidan as an active ingredient. The antitumor agent of this document utilizes inhibition of *Helicobacter pylori* colonization on the stomach wall by fucoidan and has effects of preventing infection of *Helicobacter pylori*. On the other hand, since the agent for suppressing *Helicobacter pylori* of the present invention comprising a cellooligosaccharide as an active ingredient directly suppresses *Helicobacter pylori* irrespective of colonization on the stomach wall, it has an effect of improvement in addition to prevention and is totally different from the preventing-agent of the document.

The present invention is a composition comprising a cellooligosaccharide composition with a specific saccharide composition as an active ingredient. There has been known no agent for suppressing *Helicobacter pylori* or no bacteriostatic agent against *Helicobacter pylori* that is safe to the human body which suppresses propagation of *Helicobacter pylori* by orally taking.

Hereafter, the property of the cellooligosaccharide composition for improving the skin barrier function or the cellooligosaccharide-containing composition of the present invention will be described. In the human skin, the horny cell layer functions as a barrier against the external environment of an organism. The barrier function of the skin is closely related to the amount of transepidermal water loss of the skin, and suppression of this transepidermal water loss is critical in maintaining flexibility and moisture of the skin (Non-patent Documents 5 and 6). So far, inventions have been made with a focus on regeneration of the lamellar structure of the horny cell layer using saccharides or oligosaccharides as an active ingredient.

Patent Document 4 describes an agent regenerating the lamellar structure of the horny cell layer cells in the skin that comprises glucose and/or raffinose, and an agent regenerating the lamellar structure of the horny cell layer cells in the skin characterized in that glucose and oligosaccharides are contained.

The document describes, as a lamellar structure regenerating agent, a topical agent comprising glucose as an essential component and one or more oligosaccharides selected from the group consisting of raffinose, melibiose, trehalose, sucrose, maltose, cellobiose, gentianose, stachyose, and cyclodextrin. According to this document, a lamellar structure regenerating effect is undoubtedly observed in raffinose, melibiose, trehalose, sucrose, and cyclodextrin, and an effect of decreasing "greasiness" is further observed by combination use of glucose and raffinose. However, this document has no description about recovery of the transepidermal water loss by the above-mentioned cellooligosaccharides including cellobiose. In particular, it is not known that cellooligosaccharides are excellent in usability and promotion of recovery of the transepidermal water loss and improve the skin barrier function without addition of glucose. Furthermore, since the agent for improving lamellar structure of this document needs to contain a large amount of glucose such as 7.4% by mole or more in proportion to raffinose or oligosaccharides, there was a problem that, when it was used in combination with an amino acid or a component containing an amino group such as a protein and subjected to a heating process, browning or discoloration occurred due to the Maillard reaction, which markedly reduced the commodity value. The present invention is essentially different from the above-described invention in that it has minimal "greasiness"; decreases browning; and can improve the skin barrier function without containing glucose as an essential component. Therefore, there has been known no agent for improving skin barrier function of the present invention that comprises cellooligosaccharides including cellobiose in a specific range as an active ingredient; has favorable usability; causes minimal browning; and promotes recovery of transepidermal water loss without using glucose in combination.

Hereafter, the Indigenous dermal bacteria flora improving property of the cellooligosaccharide or the cellooligosaccharide composition of the present invention will be described.

The healthy human skin maintains epidermal pH as weakly acidic and is protected by beneficial indigenous dermal bacteria having an action for improving resistance. However, internal tissues of individuals with easily damaged skin due to dry skin, atopic dermatitis, or the like are infected with *Staphylococcus aureus* and *Pseudomonas aerugunosa*, harmful bacteria, from the injury on the skin surface. The infection causes further deterioration of the human skin condition. When internal tissue is exposed, *Staphylococus aureus* and *Pseudomonas aeruginosa* are attached to the injury and grow on the exudated body fluid even if the injury is as small as invisible. In fact, it is said that a large amount off *Staphylococcus aureus* is detected in the skin of patients with atopic dermatitis. Therefore, it is extremely important to maintain the cell count of beneficial dermal bacteria and suppress the cell count of *Staphylococcus aureus* and *Pseudomonas aeruginosa*, harmful bacteria on the human skin.

Furthermore, among the skins, more indigenous dermal bacteria exist in the skin of the scalp where hairs are more densely grown than other sites, and the balance of the cell counts of these bacteria is very important. Furthermore, it is also important to impart refreshing feeling and smoothness to dry hair as sensory effects.

Many drugs and raw material components for cosmetics having a bacteriostatic action against *Staphylococcus aureus* or *Pseudomonas aeruginosa* have been disclosed. Examples thereof include N-acylglutamic acid-containing detergents (Patent Document 5, iron-bound lactoferrin-containing agents Patent Document 6), various plant extracts (Patent Documents at 8, 9, 10, and 11), and so forth. However, since these agents also have a bacteriostatic action against beneficial indigenous dermal bacteria with potency comparable to or greater than the action against bacteria belonging to genus *Staphylococcus*, they could not be used as agents for improving indigenous dermal bacteria flora.

Furthermore, an agent for adjusting the balance of the counts of Living indigenous dermal bacteria by mixing a bittern and a rosemary extract or a licorice extract has been disclosed (Patent Document 12). However, the effect was not adequate, and bacteriostasis against *Pseudomonas aeruginosa* was not described. Furthermore, refreshing feeling or smoothness was not imparted as a touch in a dried condition, and the agent was expensive and was very difficult to use in practice.

Furthermore, an agent for improving indigenous dermal bacteria flora comprising isomaltooligosaccharide has been disclosed (Patent Document 13). According to this document, an agent for improving indigenous dermal bacteria flora comprising isomaltooligosaccharide and/or a sugar alcohol obtained by reducing isomaltooligosaccharide does not act on *staphylococcus ecidermidis* in a specific range of pH and amount thereof and has an effect of suppressing *Staphylococcus aureus*. As shown in the comparative examples of the present application, however, these effects are not adequate when high amounts of carbohydrate a added in order to improve the retention of skin moisture and a touch of a face lotion. Furthermore, the document has no description about bacteriostasis against *Pseudomonas aeruginosa*, and the agent did not impart refreshingness or smoothness as a touch in a dried condition.

Therefore, the agent for improving dermal bacteria flora of the document is fundamentally different from the agent for improving indigenous dermal bacteria flora of the present invention, which does not exhibit a bacteriostatic action against a beneficial dermal bacterium, i.e. *Staphylococcus epidermidis*; but exhibits a bacteriostatic action or a propagation-suppressing action against harmful bacteria, i.e. *Staphylococcus aureus* and *Pseudomonas aeruginosa*; and imparts refreshingness or smoothness as a touch of dried hair.

Finally, the high fluidity cellooligosaccharide powder of the present invention which is excellent in oil retention in addition to powder fluidity and uniform dispensability; hardly absorbs moisture; and is excellent in handling properties such as a compression moldability, heat resistance, acid resistance, a property of preventing starch retrogradation, and a property of preventing protein modification will be described below.

Patent Document 14 describes a solid formulation comprising cellobiose as the principal ingredient and cellooligosaccharide of a degree of polymerization of L to 7 as an excipient. This cellooligosaccharide excipient undoubtedly has water activity which is equal to that of sucrose and is useful as a low-calorie sweetener. According to this patent document, however, since lyophilization is performed when a cellooligosaccharide solution obtained by enzymatic degradation of cellulose is powderized, the cellooligosaccharide powder become light, and the powder fluidity is not necessarily satisfactory. Furthermore, the patent document has no description or suggestion about the crystal shape, powder fluidity, handling properties such as uniform dispersibility of the cellooligosaccharide powder. Therefore, the formulation is essentially different from the cellooligosaccharide powder of the present invention, which highly regulates the crystal shape and physical properties of the powder of cellooligosaccharide; is excellent in powder fluidity; and has improved uniform dispersibility.

Non-patent Documents 3 and 4 describe a cellooligosaccharide powder obtained by enzymatically degrading a sulfite pulp, subjecting the obtained cellooligosaccharide solution to ultrafiltration, purifying with diatom earth and an ion exchange resin then crystallizing with ethanol and isopropyl alcohol. However, crystallization treatment with a poor solvent of the document is intended only to produce cellobiose with higher purity, and there is no description about the crystal shape of cellooligosaccharides. The technique is totally different from that of the present invention for regulating the crystal shape and physical properties of the powder to improve powder fluidity and uniform dispensability of a cellooligosaccharide powder.

Therefore, there have been known no high fluidity cellooligosaccharide powder that has highly regulated saccharide composition and crystal shape of cellooligosaccharides; is excellent in oil retention in addition to powder fluidity and uniform dispersibility; hardly absorbs moisture; and is excellent in handling properties such as a compression moldability, heat resistance, acid resistance, a property of preventing starch retrogradation, and a property of preventing protein modification as that of the present invention, and a method for producing such cellooligosaccharide powder has not been known, too.

Non-patent Document 1: New technologies of wood chemicals, CMC Publishing Co, Ltd., 66-72 (2000)

Non-patent Document 2: Nutrition, 20, 979-983 (2004)

Non-patent Document 3: Journal of Japanese Society of Nutrition and Food Science 49, No. 3, 143-148 (1998)

Non-patent Document 4: Cellulose Communications, 5, No. 2, 91-97 (1998)

Non-patent Document 5: "Advancement and future prospect of evaluation techniques for usefulness of cosmetics", Yakuji Nippo Limited, 82-101 (2001

Non-patent Document 6: "Functional cosmetics", Japan Cosmetics Science Association Ed., JISC, 235-252 (1991)

Patent Document 1: JP-A-2004-321068
Patent Document 2: JP-A-3-262460
Patent Document 3: JP-A-7-138166
Patent Document 4: JP-A-2006-45186
Patent Document 5: JP-A-11-80781
Patent Document 6: JP-A-11-279076
Patent Document 7: JP-A-6-116162
Patent Document 8: JP-A-8-73368
Patent Document 9: JP-A-8-73372
Patent Document 10: JP-A-11-43443
Patent Document 11: JP-A-2001-226280
Patent Document 12: JP-A-2005-139075
Patent Document 13: JP-A-2005-89355
Patent Document 14: JP-A-62-273921

DISCLOSURE OF THE INVENTION

An object of the present invention is to provide a high fluidity cellooligosaccharide composition that is excellent in lipid metabolism in the liver; activates selectively useful intestinal bacteria; suppresses propagation of *Helicobacter pylori* or exhibits a bacteriostatic effect against *Helicobacter pylori* by oral intake thereof; improves the skin barrier function and the dermal indigenous bacteria flora by transdermal application; and further, has a highly regulated saccharide composition and crystal shape; is excellent in oil retention in addition to powder fluidity and uniform dispersion; hardly absorbs moisture; and is excellent in handling properties such as a compression moldability, heat resistance, acid resistance, a property of preventing starch retrogradation, and a property of preventing protein modification.

The inventors of the present invention found that cellooligosaccharides having a saccharide composition and/or a crystal shape regulated in a specific range are excellent in lipid metabolism in the liver; selectively activates useful intestinal bacteria; and suppresses propagation of *Helicobacter pylori* or exhibits a bacteriostatic effect against *Helicobacter pylori* by oral intake thereof; and further improves the skin barrier function and the indigenous derma bacteria flora by transdermal application; and furthermore, is excellent in oil retention in addition to powder fluidity and uniform dispersibility; hardly absorbs moisture; and is excellent in handling properties such as a compression moldability, heat resistance, acid resistance, a property of preventing starch retrogradation, and a property of preventing protein modification, and thus, the present invention has been accomplished.

Specifically, the present invention provides the followings.

(1) A cellooligosaccharide composition, which comprises, as a principal ingredient, a cellooligosaccharide comprising cellobiose and one or more selected from the group consisting of cellotriose, cellotetraose, cellopentaose, and cellohexaose and is a powder having an average L/D of 3.0 or lower, a bulk density of 0.80 g/mL or lower, and a repose angle of 60° or smaller.

(2) The cellooligosaccharide composition according to (1), wherein the average L/D is 2.5 or lower, and the bulk density is 0.55 g/mL or lower.

(3) The cellooligosaccharide composition according to (1) or (2), wherein the repose angle is 45° or smaller.

(4) The cellooligosaccharide composition according to any one of (1) to (3), wherein the amount of oil retention is 0.9 g/g or more.

(5) The cellooligosaccharide composition according to any one of 1) to (4), wherein the moisture absorption rate after allowed to stand in an environment with a relative humidity of 75% and a temperature of 40° C. for 18 hours is 1% by mass or lower.

(6) The cellooligosaccharide composition according to any one of (1) to (5), wherein a mold formed from 200 ma of the composition by compression with 10 kN using a mortar and a pestle with circular flat surfaces of φ8.0 mm has a hardness of 60 N or higher.

(7) The cellooligosaccharide composition according to any one of (1) to (6), wherein the cellooligosaccharide residual rate is 90% or higher after heat treatment at 100° C. or higher and pH 7 or lower for 10 minutes or longer.

(8) The cellooligosaccharide composition according to any one of (1) to (7), wherein the cellobiose content is 70% by mass or higher, and the content of one or more selected from the group consisting of cellotriose, cellotetraose, cellopentaose, and cellohexaose is 0 to 30% by mass.

(9) The cellooligosaccharide composition according to (8), which contains 9% by mass or lower of glucose relative to the cellooligosaccharides.

(10) The cellooligosaccharide composition according to (8) or (9), wherein the cellobiose content is 90% by mass or higher, the content of one or more selected from the group consisting of cellotriose, cellotetraose, cellopentaose, and cellohexaose is 0.1 to 10% by mass, and the glucose content is 3.5% by mass or lower.

(11) The cellooligosaccharide composition according to (10), wherein the cellobiose content is 95% by mass or higher, the content of one or more selected from the group consisting of cellotriose, cellotetraose, cellopentaose, and cellohexaose is 0.5 to 5% by mass, and the glucose content is 0.5% by mass or lower.

(12) The cellooligosaccharide composition according to (11), wherein the glucose content is 2% by mass or lower.

(13) A cellooligosaccharide composition, which comprises cellooligosaccharides comprising 50% by mass or higher of cellobiose and 0 to 50% by mass of one or more selected from the group consisting of cellotriose, cellotetraose, cellopentaose, and cellohexaose, wherein the cellooligosaccharide are dispersed or dissolved in water or a mixed solution of water/organic solvent.

(14) A cellooligosaccharide-containing composition used as an agent for preventing or improving a lifestyle-related disease, which comprises the cellooligosaccharide composition according to any one of (1) to (13) as an active ingredient and suppresses a decrease in a blood adiponectin concentration to 30% or lower by oral intake thereof.

(15) The cellooligosaccharide-containing composition according to (14), wherein the decreasing rate of a neutral fat concentration in the liver by oral intake thereof is 15% or higher.

(16) The cellooligosaccharide-containing composition according to (14) or (15), wherein the cellooligosaccharide composition surpresses the decreasing rate of a blood adiponectin concentration to 25% or lower by oral intake thereof.

(17) A cellooligosaccharide-containing composition used as an agent for activating enteric bacteria flora, which comprises the cellooligosaccharide composition according to any one of (1) to (13) as an active ingredient, wherein the cellooligosaccharide-containing composition has a property of activating enteric bacteria flora by being assimilated by useful intestinal bacteria and not being assimilated by harmful intestinal bacteria, propagates one or more bacteria selected from the group consisting of *Bifidobacterium adolescentis, Bifidobacterium breve, Lactobacillus acidophilus, Lactobacillus casei*, and *Lactobacillus gasseri* as useful intestinal bacteria, and suppresses propagation of *Bacteroides fragilis* or *Eubacterium aerofaciens* as harmful intestinal bacteria.

(18) A cellooligosaccharide-containing composition used as an agent for activating enteric bacteria flora, which comprises the cellooligosaccharide composition according to any one of (1) to (13) as an active ingredient, wherein the cellooligosaccharide-containing composition has a property of activating enteric bacteria flora by being assimilated by useful intestinal bacteria and not being assimilated by harmful intestinal bacteria, and suppresses propagation of *Clostridium perfringens* as a harmful intestinal bacterium.

(19) A cellooligosaccharide-containing composition used as an agent for suppressing *Helicobacter pylori* propagation or a bacteriostatic agent against *Helicobacter pylori*, which comprises the cellooligosaccharide composition according to any one of (1) to (13) as an active ingredient and has a suppressing rate of *Helicobacter pylori* propagation of 1% or higher.

(20) A cellooligosaccharide-containing composition used as a bone calcium concentration enhancer, which comprises the cellooligosaccharide composition according to any one of (1) to (13) as an active ingredient and has an increasing rate of calcium concentration in the thigh bone of 5% or higher by oral intake together with calcium.

(21) A cellooligosaccharide-containing composition used as an agent for improving skin barrier functions which comprises the cellooligosaccharide composition according to any one of (1) to (13) as an active ingredient and has a recovery-promoting rate of transepidermal water loss of 10% or higher by application to the skin.

(22) A cellooligosaccharide-contain Rae composition used as an agent for improving indigenous dermal bacteria flora, which comprises the cellooligosaccharide composition according to any one of (1) to (13) as an active ingredient, wherein the active ingredient does not exhibit a bacteriostatic effect against *Staphylococcus epidermidis* and exhibits a bacteriostatic effect against *Staphylococcus aureus* and *Pseudomonas aeruginosa*.

(23) A cellooligosaccharide-containing composition used as an agent for preventing starch retrogradation, which comprises the cellooligosaccharide composition according to any one of (1) to (13) as an active ingredient, and has a starch retrogradation rate of 20% or lower after stored in the coexistence with starch.

(24) A cellooligosaccharide-containing composition used as an agent for preventing protein modification, which comprises the cellooligosaccharide composition according to any one of (1) to (131 as an active ingredient, and has a protein modification rate of 10% or lower after stored in the coexistence with a protein.

(25) The cellooligosaccharide-containing composition according to any one of (14) to (24), wherein the cellooligosaccharide composition is contained in one or more components selected from food materials, cosmetic materials, medicinal components of drugs or additives used therein, and is in the form or granule, mold, aqueous solution, water dispersion, paste, or gel.

(26) The cellooligosaccharide-containing composition according to (25), wherein the cellooligosaccharide-containing composition in the form of the aqueous solution, water dispersion, paste, or gel contains any one or more of surfactants, thickening agents, or gelatinizing agents.

(27) A cellooligosaccharide-containing food, which comprises the cellooligosaccharide-containing composition according to (25) or (26).

(28) A cellooligosaccharide-containing cosmetic, which comprises the cellooligosaccharide-containing composition according to (25) or (26).

(29) A cellooligosaccharide-containing drug, which comprises the cellooligosaccharide-containing composition according to (25) or (26).

(30) A cellooligosaccharide-containing quasi-drug, which comprises the cellooligosaccharide-containing composition according to (25) or (26).

When the cellooligosaccharide composition or the cellooligosaccharide-containing composition of the present invention is orally ingested, lipid metabolism in the liver is improved; useful intestinal bacteria are selectively activated; propagation of *Helicobacter pylori* is suppressed or a bacteriostatic effect against *Helicobacter pylori* is exhibited. Furthermore, when it is transdermally applied, the skin barrier function and the indigenous dermal bacteria flora can be improved.

Furthermore, since the cellooligosaccharide composition of the present invention has a saccharide composition and a crystal shape that are highly regulated; is excellent in oil retention in addition to powder fluidity and uniform dispersibility; hardly absorbs moisture; and is excellent in a compression moldability, heat resistance, a property of preventing starch retrogradation, and a property of preventing protein modification, a food, a cosmetic, a drug and a quasi-drug with excellent handling properties can be obtained by preparing a composition in combination with various additives.

BRIEF DESCRIPTION OF THE DRAWINGS

FIG. 1 shows a graph comparing relationships of the culture time and the viable cell count between the cases where cellooligosaccharides were added and not added in Example 18.

BEST MODE FOR CARRYING OUT THE INVENTION

The present invention will be specifically explained with a particular focus on preferred embodiments thereof.

The cellooligosaccharide composition of the present invention needs to comprise cellobiose and one or more selected from the group consisting of cellotriose, cellotetraose, cellopentaose, and cellohexaose as the principal ingredient. The term "principal ingredient" here means that 50% by mass or more of the above-mentioned cellooligosaccharide is contained in the cellooligosaccharide composition. When the cellooligosaccharide composition of the present invention comprises cellooligosaccharides as the principal ingredient, a cellooligosaccharide-containing composition that is excellent in lipid metabolism in the liver, a property of selectively activating useful intestinal bacteria, and a property of suppressing of propagation of or exhibiting a bacteriostatic action against *Helicobacter pylori* can be obtained. Furthermore, when the cellooligosaccharide composition of the present invention comprises cellooligosaccharides as the principal ingredient, a cellooligosaccharide-containing composition that is excellent in a property of improving skin barrier function and a property of improving indigenous dermal bacteria flora can be obtained.

Furthermore, when the cellooligosaccharide composition of the present invention comprises cellooligosaccharides as the principal ingredient, it becomes a cellooligosaccharide composition that has a highly regulated crystal shape; is excellent in oil retention in addition to powder fluidity and uniform dispersibility; hardly absorbs moisture; and is excellent in a compression moldability, heat resistance, and acid resistance.

Furthermore, when the cellooligosaccharide composition of the present invention comprises cellooligosaccharides as the principal ingredient, a cellooligosaccharide composition or a cellooligosaccharide-containing composition that is excellent in a property of preventing starch retrogradation, and a property of preventing protein modification is obtained. Therefore, a cellooligosaccharide-containing composition, or a cellooligosaccharide-containing food, a cosmetic, a drug or a quasi-drug that is excellent in handling properties can be obtained by preparing compositions in combination with various additives.

The average L/D ratio of the particle of cellooligosaccharide composition of the present invention is 3.0 or lower. The average T/D is closely related to powder fluidity of a cellooligosaccharide composition. When a cellooligosaccharide composition with an average L/D of 3.0 or lower is used as a powder component, a powder with excellent powder fluidity can be obtained. The term "average L/D" here is an average value of the length/diameter ratios of the particle of the cellooligosaccharide composition. This value is expressed by the average value of 0 or more samples by dispersing a cellooligosaccharide composition in ethanol, photographing an image thereof using a microscope (manufactured by KEYENCE, trade name VH-7000) at 500-fold magnification and measuring the L/D ratio of a crystal having a length of 50 to 100 μm using an image analyzer (trade name image Hyper). This average L/D is preferably 2.5 or lower, more preferably 2.2 or lower, and particularly preferably 1.8 or lower. A lower average L/D is more preferable because the fluidity of a cellooligosaccharide composition is improved. Therefore, the lower limit thereof is not particularly limited, but the range of usually obtained average L/D is 1.0 or higher.

The bulk density of the cellooligosaccharide composition of the present invention is 0.80 g/mL or lower. When the bulk density of the cellooligosaccharide composition is within the above-mentioned range, the compression moldability becomes favorable in addition to the above-described powder fluidity. The bulk density referred to herein is expressed by the inverse number of the apparent specific volume obtained by a double cylinder technique (technique comprising roughly filling 5.0 g of sample powder into a 100-mL measuring cylinder with a quantitative feeder over 1 minute, leveling the top of the powder layer using a writing-brush-like brush, and divining the volume by a sample mass, and measuring the apparent specific volume). The bulk density is preferably 0.55 g/mL or lower, more preferably 0.50 g/mL or lower, particularly preferably 0.45 g/mL or lower. The bulk density of a cellooligosaccharide composition having excellent powder fluidity is preferably 0.05 g/mL or higher, more preferably 0.20 g/mL or higher, and particularly preferably 0.30 g/mL or higher.

The repose angle of the cellooligosaccharide composition of the present invention is 60° or smaller. This repose angle is an indicator showing powder fluidity. Since the cellooligosaccharide composition has excellent fluidity when the repose angle is 60° or smaller, uniform dispersibility is improved when the cellooligosaccharide composition is mixed with components other than cellooligosaccharides to prepare a formulation. Furthermore, the repose angle in this range is preferable because variations in amounts of filling into a molding machine can be decreased when the cellooligosaccharide composition is molded. The term "repose angle" means a dynamic repose angle when a powder is allowed to pass through a Sugihara's repose angle measuring instrument at a constant rate of 15 g per minute. The repose angle is more preferably 55° or smaller, particularly preferably 45° or smaller. The above-described effects are increased with a smaller repose angle. Therefore, the lower limit thereof is not particularly limited Out the range that can be obtained by a simple procedure 10° and higher.

The cellooligosaccharide composition of the present invention is preferably cellooligosaccharide crystals and/or a granulated body of the cellooligosaccharide crystals. The crystals referred to herein have the diffraction patterns of crystal diffractions of cellooligosaccharides such as cellobiose, cellotriose, cellotetraose, cellopentaose, and cellohexaose obtained by measuring a cellooligosaccharide composition by a powder wide-angle X-ray diffraction system (manufactured by Rigaku Corporation, trade name Rotor Flex RU-300), and diffraction intensity and crystallinity are not particularly limited. Furthermore, the term "granulated body" means a granulation product in which two or more of the above-mentioned cellooligosaccharide crystals are physicochemically bound. The cellooligosaccharide composition subjected to this powder wide-angle X-ray diffraction measurement can be powderized by a known method and used for measurement when it is dry. When it is moist, it can be dried by a known method, then powderized and used for measurement.

The cellooligosaccharide composition of the present invention preferably has an average particle size of 5 to 1000 μm. The average particle size is related to powder fluidity and mixture uniformity of a cellooligosaccharide composition. The average particle size of 5 to 1000 μm is preferable because the mixture uniformity is improved when a cellooligosaccharide composition is mixed with other components to prepare a formulation. The average particle size referred to herein is obtained by measuring distributions of mass frequency and grain sizes after sifting 10 g of a sample for 20 minutes using Ro-tap sieve shaker (manufactured by Taira Kosakusho Co., Ltd., trade name Sieve Shaker Type A) and a JIS-conforming sieve (product number Z8801-1987) and expressed by the size of particles with a cumulative mass of 50%. To obtain effects such as the above-described mixture uniformity, the average particle size is preferably 10 to 500 μm, particularly preferably 20 to 400 μm.

The mold hardness of the cellooligosaccharide composition of the present invention is preferably 60 N or higher. The "mold hardness" means a property of imparting mechanical strength to a mold in a procedure in which a cellooligosaccharide composition alone or a cellooligosaccharide composition mixed with other components is molded under pressures 200 mg of the cellooligosaccharide composition of the present invention is filled in a 980 mm steel cylindrical mortar and pressurized with compression force of 10 kN for 10 seconds using a φ8.0 mm steel flat pestle. The obtained cylindrical mold is allowed to stand for 2 hours after removing pressure a load is applied in the direction of a mold diameter using a hardness tester manufactured by Freund Corporation, trade name Schleuniger 6D), and the load when the mold is destroyed is expressed by the average of 3 samples. To impart an adequate compression moldability to a cellooligosaccharide composition alone or a composition of a cellooligosaccharide composition and other components, the above-described mold hardness is more preferably 75 N or higher, particularly preferably 100 N or higher.

The oil retention of the cellooligosaccharide composition of the present invention is preferably 0.9 g/g. The term "oil retention" means the amount of oil absorbed per 1 g of powder measured by placing 2 g of a cellooligosaccharide composition on a glass plate, kneading powder with a spatula while adding rapeseed oil (Nissin Canola Oil, dropwise using a pipette, and using the point at which oil soaks out of the powder surface as the end point and is expressed by Oil retention (g/g)=amount of oil absorption (g)/
amount of cellooligosaccharide composition (g).

A greater value is preferable because separation or soaking out of oil, semisolid or liquid can be prevented when a food, a cosmetic, a drug, or a quasi-drug is produced with a prescription containing oil or a prescription containing a semisolid or a liquid at room temperature. The oil retention is more preferably in the range of 1.0 g/g and higher, particularly preferably in the range of 1.1 g/g and higher.

As heat resistance and acid resistance, the cellooligosaccharide composition of the present invention preferably has a residual rate of 90% or higher after heated at 100° C. or higher and pH 7 or lower for 1 minute or longer. A higher residual rate is preferable because the cellooligosaccharides as an active ingredient remain in the composition even after heat treatment under an acidic condition, and effects of the above-described cellooligosaccharides are maintained even after heated. The heat resistance and acid resistance are reflected by a cellobiose residual rate after heat treatment and obtained by the following method. The cellooligosaccharide composition of the present invention is dissolved in 0.1 M acetic acid-sodium acetate buffer (pH 3) at 1% by mass, sealed, and heated at 120° C. for 20 minutes, and the aqueous solution is measured after heating by the above-described high performance liquid chromatography, and the residual rate is calculated from the cellobiose concentrations before and after heat (cellobiose concentration after heating/cellobiose concentration before heating×100%). This residual rate is more preferably 95% or higher, particularly preferably 97% or higher.

The cellooligosaccharide-containing composition used as an agent for preventing or improving a lifestyle-related disease in the present invention will be explained below.

The cellooligosaccharide composition used as an agent for preventing or improving a lifestyle-related disease of the present invention preferably contains 70% by mass or higher of cellobiose. A higher cellobiose content is preferable because water solubility of the cellooligosaccharide composition and bioavailability after administration are improved. This cellobiose content is more preferably 86% by mass or higher, further preferably 90% by mass or higher, particularly preferably 95% by mass or higher.

The content of one or more selected from the group consisting of cellotriose, cellotetraose, cellopentaose, and cellohexaose in the cellooligosaccharide composition as an agent for preventing or improving a lifestyle-related disease of the present invention is preferably 0 to 30% by mass. When these cellooligosaccharides are contained, the effect of decreasing the liver lipid is improved. However, if the content is too high, solubility decreases, and the above-described bioavailability is reduced. Therefore, this content needs to be within the above-described range. The content is more preferably in the range of 0.1 to 14% by mass, further preferably 0.1 to 10% by mass, further more preferably 0.1 to 5% by mass, particularly preferably 0.5 to 5% by mass.

The glucose content in the cellooligosaccharide composition as an agent for preventing or improving a lifestyle-related disease of the present invention is preferably 9% by mass or lower. When the glucose content is low, elevation of an insulin concentration in blood can be suppressed, and the liver lipid metabolism can be particularly improved. The glucose content is preferably 3.8% by mass or lower, more preferably 3.5% by mass or lower, particularly preferably 2% by mass or lower. Since the above-described effects are increased with a lower glucose content, the lower limit thereof is not particularly limited.

Methods for analyzing contents of various cellooligosaccharides and glucose in the lifestyle-related diseases prevention or improving agent of the present invention will be explained below. The cellooligosaccharide composition of the present invention is dissolved in pure water at a concentration of 1% by mass and analyzed by high performance liquid chromatography (chromatography system manufactured by Shimadzu corporation, trade name SCL-10A; column manufactured by Shimiadzu Corporation, trade name Asahipak $NH_2$P-50; mobile phase, acetonitrile or water=75/25 [volume ratio]). The saccharide composition of the cellooligosaccharides is expressed by mass percentages of saccharides in the total mass by converting the peak areas of cellobiose, cellotriose, cellotetraose, cellopentaose, and cellohexaose in the chromatogram obtained by the above-described method to mass. The glucose content is also obtained by similar methods and expressed by a percentage of the glucose mass in the total mass calculated from the peak areas of cellobiose and glucose.

The cellooligosaccharide-containing composition used as an agent for preventing or improving a lifestyle-related disease of the present invention has a decreasing rate of blood adiponectin concentration of 30% or lower after oral intake. The blood adiponectin concentration is an indicator of a lipid metabolic disorder, and a low decreasing rate thereof is preferable because lifestyle-related diseases such as diabetes and arteriosclerosis do not develop. The term "blood adiponectin concentration" means an adiponectin concentration (μg/mL-blood) measured by ELISA (Blood adiponectin ELISA kit manufactured by Otsuka Pharmaceutical Co., Ltd.) using blood. The decreasing rate thereof can be obtained by the following a expression from adiponectin concentrations measured using blood samples when the cellooligosaccharide-containing composition is ingested and when it is not ingested: Decreasing rate (%)=([concentration when cellooligosaccharide-containing composition is not ingested)]−[concentration when cellooligosaccharide-containing composition is ingested]/(concentration when cellooligosaccharide-containing composition is no ingested (%). Since the above-described effect is increased with a lower decreasing rate of adiponectin, 25% or lower is more preferable.

The cellooligosaccharide-containing composition used as an agent for preventing or improving a lifestyle-related disease of the present invention preferably has a decreasing rate of a neutral fat concentration in the liver of 15% or higher. The effects of preventing and improving lifestyle-related diseases such as diabetes, arteriosclerosis, liver failure, and cirrhosis are increased with a greater decreasing rate of a neutral fat concentration in the liver. The term "total neutral fat concentration" also means the total neutral fat amount existing in a unit amount of the liver (mg/g-Wet liver). The decreasing rate can be obtained by the following expression from total neutral fat concentrations in the liver when cellooligosaccharide is ingested and not ingested.

Decreasing rate(%)=(concentration when cellooligosaccharide-containing composition is not ingested]−[concentration when cellooligosaccharide-containing composition is ingested])/concentration when cellooligosaccharide-containing composition is not ingested)(%)

The above-described effect is increased with a greater decreasing rate of a neutral fat concentration. Therefore, 20% or higher is more preferable.

The cellooligosaccharide-containing composition used as an agent for preventing or improving a lifestyle-related disease of the present invention preferably has a decreasing rate of a total cholesterol concentration in the liver of 10% or higher. The effects of preventing or improving lifestyle-related diseases such as diabetes, arteriosclerosis, liver failure, and cirrhosis are increased with a greater decreasing rate of a total cholesterol in the liver. The term "total cholesterol concentration" means the total cholesterol amount existing in a unit amount of the liver (mg/g-Wet liver) as with the above-described neutral fat concentration. The decreasing rate can be obtained by the following expression from total cholesterol concentrations in the liver when cellooligosaccharide is ingested and not ingested.

Decreasing rate(%)=([concentration when cellooligosaccharide-containing composition is not ingested]−[concentration when cellooligosaccharide-containing composition is ingested])/(concentration when cellooligosaccharide-containing composition is not ingested)(%).

The above-described effects are increased with a greater decreasing rate of a total cholesterol concentration. Therefore, 15% or higher is more preferable.

The cellooligosaccharide-containing composition used as an agent for preventing or improving a lifestyle-related disease of the present invention preferably has an insulin non-elevating-property. The term "insulin non-elevating-property" means that the blood insulin level does not elevate after the cellooligosaccharide-containing composition is orally ingested as compared with the insulin level before the oral intake thereof. This is determined by the following method. 7-week-old SD rats were preliminarily bred for 1 week feeding AIN-93G (manufactured by Oriental Yeast Co., Ltd.) ad libitum, fasted for 16 hours, and given 1500 mg/kg of any aqueous cellooligosaccharide solution in Table 1 using a sonde. Before dosing, after dosing, and at 30 minutes after dosing, blood was collected from the extracranial vein of unanesthetized animals, and insulin levels were measured (ng/mL, using Lbis Insulin Kit manufactured by Shibayagi Co., Ltd.). The term "insulin non-elevating-property" means that the above-mentioned elevating rate of insulin level is 30% or lower, more preferably 25% or lower, particularly preferably 20% or lower.

The expression "prevention of lifestyle-related diseases" in the present invention means that even when a high-carbohydrate meal, a high-lipid meal, a high-calorie meal, or the like is ingested, elevation of blood and visceral lipid levels can be suppressed, and lifestyle-related diseases such as diabetes, arteriosclerosis, obesity, liver failure, and cirrhosis can be prevented by orally ingesting a preventive agent comprising the cellooligosaccharide composition of the present invention as an active ingredient.

On the other hand, the expression "improvement of lifestyle-related diseases" in the present invention means that blood and visceral lipids are decreased, and the above-described lifestyle-related diseases are improved by ingesting the cellooligosaccharide-containing composition of the present invention after the above-described lifestyle-related diseases develop. When a lifestyle-related diseases preventing or improving agent containing the cellooligosaccharide-containing composition of the present invention as an active ingredient is orally effects are obtained.

The cellooligosaccharide-containing composition as a lifestyle-related diseases prevention or improving agent of the present invention has actions of decreasing the liver neutral fat concentration and the total cholesterol concentration as well as effects of decreasing blood lipids and lipids in organs other than the liver by oral intake thereof.

The blood lipids in the present invention include neutral fat, HDL and LDL cholesterols, and phospholipids in blood and can be determined by known measurement methods using serum or plasma. The expression "decreases in blood lipids" means that the measured concentrations of the above-mentioned blood lipids are lower than values before the cellooligosaccharide-containing composition is administered or values when the cellooligosaccharide-containing composition is not administered.

Furthermore, the term "visceral lipids" in the present invention includes HDL and LDL cholesterols, phospholipids in the liver, epididymis lipids, and the above-described lipids existing in the abdominal cavity around the kidneys in addition to the above-described neutral fat and total cholesterol concentration in the liver. These lipids are also expressed by lipid concentrations or masses as with blood lipids, and the expression "decreases in visceral lipid concentrations" means that the lipid concentrations or masses decreased compared with that before cellooligosaccharides are administered or when a cellooligosaccharides are not administered.

The cellooligosaccharide-containing composition used as an agent for activating enteric bacteria of the present invention will be explained below.

The cellooligosaccharide-containing composition used as an agent for activating enteric bacteria flora of the present invention selectively activates useful bacteria such as intestinal bifidobacteria and lactic bacteria, and also has an effect as an agent for activating enteric bacteria that suppresses harmful bacteria, i.e. *Bacteroides fragilis* and *Eubacterium aerofaciens*. To achieve this, it is preferable to regulate the composition of cellobiose, cellotriose, cellotetraose, cellopentaose, and cellohexaose and the glucose content in the cellooligosaccharide within the specific range as shown below.

The cellooligosaccharide composition used as an agent for activating enteric bacteria flora of the present invention preferably contains 70% by mass or higher of cellobiose. Cellobiose has an effect of propagating useful bacteria classified as bifidobacteria and lactic bacteria and does not propagate harmful bacteria belonging to genera *Clostridium, Escherichia, Bacteroides*, and *Eubacterium*. The term "bifidobacaeria" here means useful bacteria belonging to the genus *Bifidobacterlum*, and examples thereof include *Bifidobacterium adolescentis* and *Bifidobacterium breve*. The term "lactic bacteria" means useful bacteria belonging to the genus Lactobacillus, and examples thereof include *Lactobacillus acidophilus, Lactobacillus casei*, and *Lactobacillus gasseri*.

Furthermore, the term "*Clostridium*" means harmful bacteria belonging to the genus *Clostridium*, and examples thereof include *Clostridium perfringens* (also known as Welch *bacillus*. Hereinafter referred to as *C. perfringens*). The term "*Escherichia*" means harmful bacteria belonging to the genus *Escherichia*, and examples thereof include *Escherichia coli* (also known as colon *bacillus*. Hereinafter referred to as *E. coli*). The term "*Bacteroides*" means harmful bacteria belonging to the genus *Bacteroides*, and examples thereof include *Bacteroides fragllis* (hereinafter referred to as *B. fragulis*). The term "*Eubacterium*" means harmful bacteria belonging the genus *Eubacterium*, and examples thereof include *Eubacterium aerofaciens* (S-12 strain, *E. aerofaciens*).

Cellobiose is particularly characterized in that it is not assimilated by *B. fragilis* among these bacteria. A higher cellobiose content is preferable because it can activate bifidobacteria and lactic bacteria while suppressing propagation of *C. perfringens, E. coli*, and *B. fragilis*. The cellobiose content is more preferably in the range of 80% by mass or higher, particularly preferably 95% by mass or higher. Since the above-described effects are increased with a higher cellobiose content, the upper limit thereof is not particularly limited, but the range that can be obtained by a simple procedure is 99.9% by mass and lower.

The cellooligosaccharide used as an agent for activating enteric bacteria flora of the present invention needs to contain 0 to 30% by mass of one or more selected from the group consisting of cellotriose, cellotetraose, cellopentaose, and cellohexaose. These cellooligosaccharides have an effect of activating useful bacteria such as bifidobacteria and lactic bacteria comparable to that of cellobiose. However, they have a different harmful bacteria assimilation property different from that of cellobiose and are characterized in that they are hardly assimilated particularly by *E. aerofaciens*. Since propagation of *E. aerofaciens* can be suppressed, and bifidobacteria and lactic bacteria can be activated to a greater extent with a higher content of one or more selected from the group consisting of cellotriose, cellotetraose, cellopentaose, and cellohexaose, a higher content is preferable. However, when this content is high, the effect of suppressing propagation *B. fragilis* is decreased. Therefore, to selectively activate bifidobacteria and lactic bacteria and to suppress the propagation of any harmful bacteria such as *Bacteroides* and *Eubacterium* in addition to Welch *bacillus* and *Escherichia coli*, the content should be within the above-described range. The content is preferably in the range 0.1 to 20% mass, more preferably in the range of 0.1 to 10% by mass, further preferably in the range of 0.1 to 5% by mass, particularly preferably in the range of 0.1 to 3% by mass.

In the cellooligosaccharide composition used as an agent for activating enteric bacteria flora of the present invention, the glucose content is preferably 9% by mass or lower, more preferably 3.8% by mass or lower, particularly preferably 2% by mass or lower. Since glucose propagates *C. perfringens, E. coli, B. fragilis*, and *E. aerofaciens*, the glucose content needs to meet the above-described range to selectively activate only useful bacteria. Since the selective activation effect is promoted with a lower glucose content, the glucose content is further preferably in the range of 1.5% by mass or lower, particularly preferably in the range of 1% by mass or lower. The lower limit is not particularly established, but the range that can be obtained by a simple procedure is 0.1% by mass and higher. The contents of cellooligosaccharides and glucose in the agent for activating enteric bacteria of the present invention are analyzed as described above.

The effect of improving enteric bacteria flora of the cellooligosaccharide-containing composition of the present invention can be confirmed by the following method.

First, 0.5% by mass of the cellooligosaccharide-containing composition of the present invention is added to a Peptone-Yeast-Fildes solution (PYF, manufactured by Nihon Pharmaceutical Co., Ltd.) medium to prepare 1.5 mL of sterilized medium pH 7.2), 0.03 mL of test bacterial solutions in which bifidobacteria, lactic bacteria, *C. perfringens, E. coli, B. fragilis*, and *E. aerofaciens* are separately pre-cultured beforehand, inoculated to a Fildes solution-added CAM bouillon medium (0.4% by volume of Fildes solution is added to GAM bouillon [product name] manufactured by Nihon Pharmaceutical Co., Ltd.), and anaerobically cultured at 37° C. for 96 hours, and pH is measured to determine an assimilation property. When the pH is lower than 5.5, it can be determined that the bacterial strain assimilates the cellooligosaccharides. A lower pH means that the more propagation of the bacterial strain proceeds to a greater extent.

The cellooligosaccharide-containing composition used as an agent for suppressing *Helicobacter pylori* or a bacteriostatic agent against *Helicobacter pylori* of the present invention will be explained below.

The cellooligosaccharide-containing composition used as an agent for suppressing *Helicobacter pylori* or a bacteriostatic agent against *Helicobacter pylori* of the present invention preferably contains 70% by mass or higher of cellobiose. Cellobiose has an effect of suppressing propagation of *Helicobacter pylori* in an aqueous medium. Therefore, the higher cellobiose content is preferable because propagation of *Helicobacter pylori* is suppressed to a greater extent. The content is preferably 90% by mass or higher, more preferably 95% by mass or higher.

The cellooligosaccharide-containing composition used as an agent for suppressing *Helicobacter pylori* or a bacteriostatic agent against *Helicobacter pylori* of the present invention preferably contains 0 to −0% by mass of one or more selected from cellotriose, cellotetraose, cellopentaose, and cellohexaose. These saccharides also have the same effect of suppressing *Helicobacter pylori* propagation as cellobiose. However, since solubility in an aqueous medium decreases with the increase in glucose residues, this content needs to be within the above-described range to obtain effects of the present invention as cellooligosaccharides. The content is preferably in the range of 0 to 10% by mass, more preferably in the range of 0 to 5% by mass, particularly preferably in the range of 0.5 to 5% by mass.

In the cellooligosaccharide-containing composition of the present invention used as an agent for suppressing *Helicobacter pylori* or a bacteriostatic agent against *Helicobacter pylori*, the glucose content is preferably 30% by mass or lower. Since glucose propagates *Helicobacter pylori*, the effect of suppressing *Helicobacter pylori* of the cellooligosaccharides is decreased when a large amount of glucose is contained. Therefore, the glucose content needs to be within the above-described range. The effect of suppressing *Helicobacter pylori* is promoted with a lower glucose content. The glucose content is preferably in the range of 20% by mass or lower, more preferably in the range of 10% by mass or lower, particularly preferably in the range of 5% by mass or lower the lower limit is not particularly established, bur the range that can be obtained by a simple procedure is 0.1% by mass and higher.

*Helicobacter pylori* of which propagation is suppressed by the cellooligosaccharide-containing composition or used as an agent for suppressing *Helicobacter pylori* or a bacteriostatic agent against *Helicobacter pylori* of the present invention corresponds to bacteria classified as "*Helicobacter pylori*", and examples thereof include stored bacterial strains such as *Helicobacter pylori* ATCC 43504 and 43526 strains and clinical isolates. The suppressing rate of *Helicobacter pylori* propagation of the agent for suppressing *Helicobacter pylori* or a bacteriostatic agent against *Helicobacter pylori* comprising cellooligosaccharides of the present invention is preferably 1% or higher. The term "suppressing rate of propagation" means a percentage of the viable cell count when *Helicobacter pylori* is cultured with addition of the cellooligosaccharides (viable cell count 1) to the viable cell count when *Helicobacter pylori* is cultured without adding the cellooligosaccharides (viable cell count 2) and can be expressed by the following expression Suppressing rate of propagation(%)=(viable cell count 2−viable cell count 1)/viable cell count 2×100

Since the *Helicobacter pylori* suppressing effect or a bacteriostatic effect is increased with a higher suppressing rate of propagation, the rate is preferably in the range of 10% or higher, more preferably in the 40% or higher, particularly preferably in the 50% or higher.

The viable cell count of *Helicobacter pylori* in the present invention can be measured by the following method. The test bacterial strain (*Helicobacter pylori* ATCC43504) is microaerobically cultured in a sheep blood agar medium K (BBL) at 35° C. for 3 days and adjusted with sterilized physiological saline to obtain McFarland No. 2 (about $10^7$ to $10^8$ CFU/mL). This solution is 100-fold diluted with a sterilize physiological saline to obtain a bacterial solution for addition. 5% equine serum is added to *Brucella* broth (manufactured by Eiken Chemical) 10-fold diluted with water to obtain a test solution containing no cellooligosaccharide. To this solution is added cellooligosaccharides having predetermined concentrations to obtain a cellooligosaccharide-added test solution. 1 mL of the bacterial solution for addition is added to 9 mL of each test solution, and the bacterial cells are cultured at 35° C. under a microaerobic condition with stirring to use it as a sample solution. After 48 hours of culture, each sample solution is collected, a series of 10-fold diluted solutions are prepared with sterilized physiological saline. 50 μL each of the stock solution and the series of diluted solutions are smeared with a Conradi's glass rod to a sheep blood aqar medium K and cultured under a microaerobic condition at 35° C. for 4 to 5 days. After 0 hour, only test solutions are quantified. The number of bacterial cells that grew after the culture are counted to obtain the viable cell count per mL.

The cellooligosaccharide-containing composition used as a bone calcium concentration enhancer will be explained below.

The cellooligosaccharide-containing composition used as a bone calcium concentration enhancer of the present invention preferably has an increasing rate of calcium concentration in thigh bone of 5% or higher after oral intake thereof with calcium. Since higher effects of preventing or improving osteoporosis or the like are obtained with a greater increasing rate of calcium concentration in thigh bone, this rate is more preferably 10% or higher, particularly preferably 15% or higher.

The term "increasing rate of calcium concentration in thigh bone" means the total amount of calcium existing in the thigh bone per unit amount (mg/g-dry thigh bone). The increasing rate is obtained by the following expression from total calcium concentrations in the thigh bone after cellooligosaccharides are ingested and when they are not ingested.

Increasing rate(%)=([concentration ater cellooligosaccharides are ingested]−[concentration when they are not ingested])/(concentration when they are not ingested)(%)

The cellooligosaccharide-containing composition used as an agent for improving skin barrier function of the present invention will be explained below.

The cellooligosaccharide-containing composition used as an agent for improving skin barrier function of the present invention preferably has a cellooligosaccharide composition in which the cellobiose content is 70% by mass or higher, 0 to 30% by mass of one or more selected from the group consisting of cellotriose, cellotetraose, cellopentaose, and cellohexaose is contained, and the glucose content is 3.5% by mass or lower. When the above-described cellooligosaccharide composition is contained, the recovery rate of transepidermal water loss of the damaged skin is improved, and an agent for improving barrier function which has no "greasiness" and has "smoothness" and favorable usability can be obtained without using glucose in combination.

The cellobiose content in the cellooligosaccharides of the present invention is preferably 70% by mass or higher. The recovery-promoting rate of transepidermal water loss is improved with h a higher cellobiose content. Therefore, the cellobiose content is more preferably 80% by mass or higher, further preferably 90% by mass or higher, particularly preferably 95% by mass or higher. Since the above-described effects are increased with a higher cellobiose content, the upper limit thereof is not particularly limited, but the range that can be obtained by a simple procedure is 99.9% by mass and lower.

The cellooligosaccharide composition of the present invention preferably contains 0 to 30% by mass of one or more selected from the group consisting of cellotriose, cellotetraose, cellopentaose, and cellohexaose. When the cellooligosaccharide composition contains one or more selected from the group consisting of cellotriose, cellotetraose, cellopentaose, and cellohexaose in the above-described range, it has the excellent recovery effect of transepidermal water loss and "smoothness" and less "greasiness." However, if the content of these components is too high, "smoothness" of the agent for improving barrier function is decreased. Therefore, the content is more preferably 0.1 to 10% by mass, further preferably 0.1 to 1% by mass or lower, particularly preferably 0.1 to 3% by mass or lower.

The glucose content in the cellooligosaccharide-containing composition used as an agent for improving barrier function of the present invention is preferably 3.5% by mass or lower. Glucose reacts with an amino acid and a component having an amino group of a protein saccharine and causes browning of the agent for improving skin barrier function and inactivation of an active ingredient. Therefore, a lower glucose content is preferable because the above-described browning and inactivation of an active ingredient can be prevented to a greater extent. The glucose content is more preferably 3.0% by mass or lowers particularly preferably 2% by mass or lower. The lower limit is not particularly limited, but the range obtained by a simple procedure is 0.1% by mass and higher. The contents of cellooligosaccharides and glucose in the agent for improving barrier function of the present invention are analyzed as described above.

The barrier function in the present invention is expressed by the recovery-promoting rate of transepidermal water loss, and the recovery-promoting rate of transepidermal water loss of the agent for improving barrier function of the present invention is preferably 10% or higher. The recovery-promoting rate referred to herein is expressed by a decreasing rate of relative transepidermal water loss of the cellooligosaccharide-containing composition to a relative transepidermal water loss of purified water using a relative transepidermal water loss 2 hours after applications of the aqueous cellooligosaccharide solution and a relative transepidermal water loss obtained from purified water to the rough skin. This value is obtained by the following expression.

Recovery-promoting rate(%)=([relative transepidermal water loss of water)−[relative transepidermal water loss of cellooligosaccharide-containing composition]/(relative transepidermal water loss of water)×100

The above-described effect of improving barrier function is higher with a higher recovery-promoting rate, and this rate is preferably 20% or higher, more preferably 25% or higher.

Furthermore, a relative value of the above-mentioned transepidermal water loss (relative transepidermal water loss) can be measured by transepidermal water loss (TEWL) in the rough skin. First, the inner side of the forearm (test site) is wiped with 70% ethanol and habituated in a room with a constant temperature and a humidity (room temperature 22° C., humidity 45%) for 15 minutes, and the test site is measured with a 2-channel moisture loss monitor (manufactured by Asahi Biomed, TW-AS type to obtain the initial TEWL value (TEWEL0). Then, after measurement of the initial TEWL, the test site is washed with water, the test site is coated with 2% by mass of sodium dodecylsulfate (SDS, by a closed patch and washed with water using a Finn chamber (manufactured by Epitest), and then TEWL (TSWL rough skin) is measured in the same manner as described above. Then purified water or the aqueous cellooligosaccharide solution of the present invention is applied to the same site, and TEWL at the site is measured 2 hours after application (TEWL2) by the above-described method. Taking the rough skin as 100, relative TEWL values are obtained by the following expression.

Relative transepidermal water loss(%)=(TEWL2−TEWLO/(TEWL rough skin−TFWE0)×100

The cellooligosaccharide-containing composition used as an agent for improving indigenous dermal bacteria flora of the present invention will be explained below.

To impart refreshingness and smoothness as a touch of dried hair, it is preferable that the cellobiose content is 70% by mass or higher, and 0 to 30% by mass of one or more selected from the group consisting of cellotriose, cellotetraose, cellopentaose, and cellohexaose are contained. Furthermore, it is more preferable that the cellobiose content is 95% by mass or higher and lower than 99.5% by mass, and 0.1 to 5% by mass of one or more selected from the group consisting of cellotriose, cellotetraose, cellopentaose, and cellohexaose are contained. When the cellobiose content does not reach 70% by mass, refreshingness and smoothness cannot be imparted as a touch of dried hair. Furthermore, when cellobiose is degraded to glucose, a monosaccharide, free glucose is easily assimilated by harmful bacteria, and refreshingness and smoothness are decreased as a touch of dried hair. Therefore, the free glucose content is preferably 0.1 to 5% by mass or lower relative to the cellooligosaccharide content, more preferably 4% by mass or lower, further preferably 3.5% by mass or lower, particularly preferably 2% by mass or lower. The contents of cellooligosaccharides and glucose in the agent for improving barrier function of the present invention are analyzed as described above.

By containing the cellooligosaccharide composition of the present invention, the cellooligosaccharide-containing composition used as an agent for improving indigenous dermal bacteria flora of the present invention does not exhibit a bacteriostatic action against a beneficial skin bacterium, i.e. *Staphylococcus epidermis*, but exhibits a bacteriostatic action or an action for inhibiting propagation of harmful bacteria, i.e. *Staphylococcus aureus* and *Pseudomonas aeruginosa*, and can impart refreshingness and smoothness as a touch of dried hair when it is used as a dermal topical agent or a hair agent.

In the present invention, cell counts of *Staphylococcus epidermidis, Staphylococcus aureus* and *Pseudomonas aerugonosa*, which is a harmful bacterium, can be measured by the following method. First, *Staphylococcus epidermis, Staphylococcus aureus,* and *Pseudomonas aeruginosa*, which is a harmful bacterium, are cultured in a nutrient bouillon medium at 35° C. for 24 hours, and the medium is diluted with sterilized distilled water to about $10^7$ cells/mL to obtain a bacterial cell solution for addition. Test substances such as saccharides are dissolved in sterilized distilled water at predetermined concentrations, 1 mL of the bacterial cell solution for addition is added to 9 mL of each solution, and the mixture is stirred. This sample solution is added dropwise to an egg yolk-added mannitol salt agar medium and cultured at 35° C. for 48 hours, and then the bacterial cell count is measured (initial value). Furthermore, the sample solution is maintained at 35° C., and the same procedures are performed at 1 day and 2 days after preparation to measure the bacterial cell count.

The measured bacterial cell count of the blank and those of the sample solutions containing test substances such as saccharides are compared to evaluate the bacteriostatic effect and the bacterial propagation effect of the saccharides against *Staphylococcus epidermis, Staphylococcus aureus,* and *Pseudomonas aeruginosa*.

The property of preventing starch retrogradation of the cellooligosaccharides of the present invention preferably has a starch retrogradation rate of 20% or lower. The starch retrogradation rate referred to herein is an indicator showing a degree in which the cellooligosaccharides of the present invention suppress retrogradation of starch in coexistence of starch. The effect of preventing starch retrogradation is increased with a lower retrogradation rate. This retrogradation rate is measured by the following method. First, a water dispersion of potato starch (manufactured by Sanwa Cornstarch Co., Ltd.) having a concentration of 1% by mass is heated at 100° C. for 1 hour to obtain an aqueous starch solution. The cellooligosaccharide composition of the present invention dissolved in this aqueous starch solution at 6% by mass at room temperature, sealed, and stored at 4° C. for 12 hours. Subsequently, turbidity (transmissivity) of the aqueous solution after storage is measured at a wavelength of 660 nm at room temperature, and the rate of increasing turbidity of the aqueous solution from before refrigerated storage ([turbidity after storage−turbidity before storage]/turbidity before storage×100%). The effect of preventing starch retrogradation is increased with a lower retrogradation rater and it is more preferably 15% or lower, particularly preferably 1% or lower.

The property of preventing protein modification of the cellooligosaccharide of the present invention is preferably 10% or lower as the protein modification rate. The "protein modification rate" referred to herein is an indicator showing a degree of suppression of protein modification by the cellooligosaccharide composition of the present invention in the coexistence of the protein. The effect of suppressing protein modification is increased with a lower modification rate. This modification rate is measured by the following method. First, an aqueous solution of the cellooligosaccharides of the present invention at 10% by mass is mixed with an equivalent of egg white at room temperature, sealed, and stored at −20° C. for 5 days. Then, turbidity (transmissivity) of the aqueous solution after storage is measured at room temperature at a wavelength of 660 nm to obtain the increasing rate of turbidity of the aqueous solution from before refrigerated storage ([turbidity after storage−turbidity before storage]/turbidity before storage×100%). The effect is increased with a lower modification rates and the modification rate is more preferably 75% or lower, particularly preferably 5% or lower.

The method or producing the cellooligosaccharides of the present invention will be explained below.

Origins of the cellooligosaccharides of the present invention are not particularly limited. The may be produced by hydrolysis of a cellulose substance, condensation or saccharide transfer of a monosaccharide such as glucose or derivatives thereof, but are preferably obtained by enzymatic degradation in view of safety.

Cellulose substances used for enzymatic degradation may be of plant or animal origin, and examples thereof include natural products derived fibrous substances contained in wood, bamboo, cotton, ramie, sea squirt, bagasse, kenaf, wheat, rice plant, bacterial cellulose, and the like. Furthermore, regenerated celluloses obtained by once dissolving these in a solvent to regenerate or cellulose derivatives obtained by subjecting these to chemical treatment may be used, or one or two or more of the above-mentioned cellulose substances may be used in combination. Natural cellulose substances not dissolved or subjected to chemical treatment among these are preferable because a solvent or a chemical substance harmful to a human body is not contained in the obtained cellooligosaccharides. Furthermore, cellulose substances are preferably used in the form of a purified pulp. The method for purification of a pulp is not particularly limited, and any pulps such as sulfite pulp, kraft pulp, and NBKP pulp may be used.

Furthermore, when a cellulose substance is enzymatically degraded, the cellulose substances which is once hydrolyzed and partially hydrolyzed to an average degree of polymerization of 700 or lower are preferably used to improve the yield of a cellooligosaccharide. Furthermore, the cellulose substances having specific polymerization degrees preferably have an average particle size regulated to 100 μm or lower and a colloidal cellulose component content regulated to 10% by mass or higher to improve the enzymatic degradation rate and the cellooligosaccharide selection rate.

In the present invention, an enzyme used for hydrolysis of a cellulose substance is referred to as cellulase. The cellulase used in the present invention is a generic name of enzymes that degrade cellulose, and enzymes having an activity of degrading cellulose are included in cellulase referred to in the present invention. Examples of the cellulase enzyme sources include cellulose-producing viable cells themselves, purified enzymes secreted from cellulase-producing viable bacterial cells, formulations of purified enzymes, formula ions prepared with additives such as excipients and stabilizers, and so forth. In the case of cellulase formulation products, additives added thereto are not particularly limited either, and the dosage form thereof may be any of powder, granule, liquid, and the like.

The cellulase source is not particularly limited, but examples of known cellulose producing microorganisms include bacteria belonging to the genera *Trichoderma, Acremonium, Aspergllus, Bacillus, Pseudomonas, Penioillium, Aeromonus, Irpex, Sporotrlchum, Humicola, Cellovibrio*, and the like described in "Cellulase" (published by Kodansha Scientific [1987]) and "Encyclopedia of cellulose" published by Asakura Publishing Co., Ltd. [2000]). Cellulase is not limited to enzymes produced by the above-mentioned known bacteria, and novel bacteria derived enzymes are also include in the cellulose of the present invention so long as they are cellulose degrading enzymes.

The method for degrading cellulose substances by enzymes is not particularly limited, and known methods can be used. One example is a method comprising suspending a cellulose substance in an aqueous medium adding cellulose, and heating the mixture with stirring or shaking for glycation reaction.

In the above-mentioned method, reaction conditions such as a suspension method, a stirring method, a cellulase and substrate addition method, an order of addition, and concentrations thereof are suitably adjusted to obtain a high yield of cellooligosaccharides. At this time, pH and temperature of the reaction mixture are not limited so long as they are within a range in which the enzyme is not inactivated. In general, when a reaction is performed under normal pressure, it is sufficient that temperature is in the range of 5 to 950, and pH is in the range of 1 to 11. Furthermore, these pressure, temperature, and pH are suitably adjusted as described above so that a higher yield of cellooligosaccharides can be obtained.

The aqueous cellooligosaccharide solution obtained by the above-described enzymatic degradation can be subjected to purification treatment such as decolorization, desalting, and enzyme removal, if necessary. The purification method is not particularly limited so long as it is a known method, but, for example, active carbon treatment, ion exchange resin treatment, chromatography treatment, filtration treatment such as microfiltration, ultrafiltration, and reverse osmosis filtration, or crystallization treatment may be employed, and each of these treatments may be employed solely, or two or more thereof may be employed in combination.

Among the cellooligosaccharide purification methods, crystallization treatment is preferable because the cellooligosaccharide composition is easily regulated.

As an example of the enzyme degradation method, the cellooligosaccharides produced by the method disclosed in WO2006/011479A1 is preferably used.

Among the cellooligosaccharide purification methods, crystallization treatment is preferable because average L/D and purity of cellooligosaccharide crystals can be simultaneously regulated.

In crystallization of the present invention, one or two or more solvents are mixed to an aqueous cellooligosaccharide solution, cellooligosaccharides are crystallized from Hildebrand's solubility parameter δ of 8.0 to 22.2. When this solubility parameter δ is within the range of the present invention, the average L/D of the obtained cellooligosaccharide crystals or crystal aggregate can be regulated, and fluidity of the cellooligosaccharide composition is improved. This solubility parameter is preferably 10 to 20, more preferably 12 to 18.

The solubility parameter referred to in the present invention is Hildebrand's solubility parameter δ and is obtained by the following expression 1, $$\delta = (\Delta E^v/V)^{1/2} \quad (1)$$

$\Delta E^v$ represents heat of evaporation (cal/mol) of a solvent at 25° C., and V represents molar volume of a solvent (cm³/mol). $\Delta E^v$ is calculated by the following expression (2).

$$\Delta E^v(\text{cal/mol}) = -3.542 + 23.7T_b + 0.020T_b \quad (2)$$

T represents a boiling point of a solvent expressed by absolute temperature.

Furthermore, the solubility parameter $\delta_{mix}$ of a mixed solvent is calculated by the following expression (3) from the solubility parameter of each solvent.

$$\delta_{mix} = (X_1 V_1 \delta_1 + X_2 V_2 \delta_2 + X_3 V_3 \delta_3 + \ldots + X_n V_n \delta_n) \quad (3)$$

X represents the molar fraction (% by mole) of each solvent, and V (cm³/mol) represents the molar volume of a solvent.

The type of the solvent used in crystallization of the present invention is not particularly limited so long as the solubility parameter thereof is 8.0 to 22.2 Examples of the solvent used herein include water, alcohols such as methanol, ethanol, n-propyl alcohol, isopropyl alcohol, butyl alcohol, 2-methylbutyl alcohol, and benzyl alcohol, ketones such as acetone, methyl ethyl ketone, diethyl ketone, and methyl propyl ketone, nitriles such as acetonitrile, and so forth. In particular, organic solvents used in processes for producing drugs, foods, and additives are preferable, and examples thereof include compounds classified as solvents in "Japanese Pharmaceutical Excipients Directory" (published by Yakuji Nippo Limited), "Japanese Pharmacopoeia" and "Japanese Standards of Food Additives" (all published by Hirokawa-Shoten Ltd.). Each of water and organic solvents may be used solely, or two or more thereof may be used in combination. They may be once dispersed in one type of medium, followed by removal of the medium, and be dispersed in a different medium.

The crystallization method used herein is not particularly limited, but preferred examples thereof include solvent evaporation concentration crystallization method (concentration crystallization method), cooling crystallization method, poor solvent addition crystallization method (extraction crystallization method, pressure crystallization method, and reaction crystallization method. One or two or more of these may be used in combination. A solvent used as a mother liquor, a crystallization device, and crystallization conditions are suitably adjusted so that cellooligosaccharide crystals should have an average L/D within the range of the present invention. In particular, the concentration crystallization method in the aqueous system, the cooling crystallization method, and a combination method thereof are preferable because the cellooligosaccharide crystallization rate and the average L/D can be easily regulated.

The crystallization device used herein is not particularly limited either, but any devices such as a stationary crystallizer, a usual stirring crystallizer, a draft tube stirring crystallizer, an Oslo type crystallizer, an indirect cooling crystallizer, a scratching crystallizer, a calandria type crystallizer, a Brody crystallizer, and a continuous melt purification type crystallizer can be used. Each of these may be used solely, or two or more thereof may be used in combination in particular, when concentration and cooling crystallization are performed in the aqueous system, and a crystal size is regulated to be large, and the average L/D is regulated to be small, a stationary type is preferable. When a stirring type is used, the stirring rate is preferably as low as possible. Furthermore, when the above-mentioned crystal size and average L/D are regulated in cooling crystallization, the cooling rate is preferably made low. When extraction crystallization is performed, the rate of addition of a poor solvent is preferably made low.

A cellooligosaccharide-containing composition comprising the cellooligosaccharide composition of the present invention as an active ingredient will be explained below.

The cellooligosaccharide-containing composition comprising the cellooligosaccharide composition of the present invention as an active ingredient may use the cellooligosaccharide composition of the present invention solely in the form of powder, as an aqueous solution or a dispersion, a food material, a cosmetic material, drug medicinal component, or as a food or a drug in the form of granule, mold, aqueous solution, water dispersion, paste, or gel together with one or more components selected from additives used therein in addition to the cellooligosaccharide composition of the present invention.

The mixture ratio of cellooligosaccharides in the cellooligosaccharide composition of the present invention is preferably 0.01 to 100% by mass. The term "mixture ratio of cellooligosaccharides" here means a total amount of cellobiose, cellotriose, cellotetraose, cellopentaose, and cellohexaose contained in the agent for preventing or improving a lifestyle-related disease of the present invention. A mixture ratio of cellooligosaccharides of lower than 0.01% by mass is not preferable because adequate effects are not observed in prevention or improvement of lifestyle-related diseases, activation of enteric bacteria flora, improvement of the skin barrier function, or improvement of the indigenous dermal bacteria flora. A higher rate is preferable because the above-described effects are promoted with a higher cellooligosaccharide mixture ratio. This rate is more preferably in the range of 0.6% by mass or higher, particularly preferably in the range of 0.75% by mass or higher.

The cellooligosaccharide-containing composition of the present invention may contain an oligosaccharide or a very sweet sweetener in addition to the cellooligosaccharide composition of the present invention. The mixture ratios of cellooligosaccharides and an oligosaccharide or a very sweet sweetener are not particularly limited so long as they are within the range in which the effects of the present invention are obtained, but are, for example, 0.11/99.9 to 99.9/0.1 as a mass ratio of cellooligosaccharides and an oligosaccharide.

In particular, it is preferable to add a non-digestible oligosaccharide because actions of activating useful intestinal bacteria and regulating intestinal functions can also be obtained in addition to lipid metabolism of the cellooligosaccharide. Furthermore, it is preferable to add a very sweet sweetener to the cellooligosaccharides of the present invention because a quality of taste can be adjusted without increasing calories of the cellooligosaccharides.

Examples of this oligosaccharide include compounds classified as sweeteners in "Japanese Standards of Food Additives" published by Hirokawa-Shoten Ltd.) such as monosaccharides such as galactose, fructose, mannose, arabinose, rhamnose, ribose, xylose, sorbose, and reduction products thereof, disaccharides such as sucrose, melibiose, trehalose, lactose, maltose, gentiobiose, laminaribiose, lactulose, xylobiose, and reduction products thereof, trisaccharides such as lactosucrose, raffinose, maltotriose, isomaltose, paratinose, kestose, and geontiosyl cellobiose, and reduction products thereof, tetrasaccharides such as maltotetraose, gentiosyl cellotriose, nistose, and reduction products thereof, penta- or hexasaccharides such as maltopentaose, maltohexaose, and reduction products thereof, cyclic oligosaccharides such as β-cyclodextrin, γ-cyclodextrin, and dextran, water-soluble polysaccharides such as non-digestible dextrin, polydextrose, gum arabic, carboxymethylcellulose, guar gum, curdlan, and reduction products thereof, sugar alcohols such as sorbitol, xylitol, multilol, mannitol, and lactitol. These oligosaccharides may be used as oligosaccharides as they are, or as derivatives obtained by subjecting a part of the chemical structure thereof to chemical treatments such as carboxylation, ethylation, methylation, and sulfuric acid esterification to improve solubility or the like.

Examples of the very sweet sweetener include compounds classified as very sweet sweeteners in "Japanese Standards of Food Additives" published by Hirokawa-Shoten Ltd.) such as saccharin, licorice (glycyrrhizin), stevia, aspartame, sucralose, and acesulfame potassium. These very sweet sweeteners may also be used as sweeteners as they are, or as derivatives obtained by replacing a part of the chemical structure thereof with other substituents.

The term "components" used in the present invention means additives such as oligosaccharides other than cellooligosaccharides, very sweet sweeteners, food materials, cosmetic materials, drug medicinal components, dyes, flavors, metals, ceramics or excipients, disintegrating agents, binders, fluidizers, lubricants, flavoring agents, coloring materials, sweeteners, solvents, oils and fats, surfactants, thickening agents, and gelatinization agents, and they may be in any form of powder, crystals, oil, liquid, semisolid, and the like. For example, those described in "Japanese Standards of Food Additives" published by Hirokawa-Shoten Ltd.) Japanese Standards of Cosmetic Ingredients (JSCI)," "Comprehensive Licensing Standards of Cosmetics by Category (both published by Yakuji Nippo Limited), "Japanese Pharmacopoeia" (published by Hirokawa-Shoten Ltd.), and "Encyclopedia of Drug Additives" (published by Yakuji Nippo Limited) can be used.

Furthermore, these may be subjected to industrial processes such as coating and liposome encapsulation for various purposes. Each of these components may be used solely, or two or more thereof may be used in combination. The lifestyle-related disease preventing or improving agent of the present invention can be processed by known methods such as dissolution, mixing dispersion, granulation, melting/caking, compression, and drying.

Methods for producing compositions containing the cellooligosaccharide composition of the present invention as an active ingredient (cellooligosaccharide-containing compositions, food materials, cosmetic materials, drug medicinal components, and foods, cosmetics, drugs, and quasi-drugs comprising one or more components selected from additives used therein will be described below.

The method of adding each component is not particularly limited so long as it is a commonly used method, but 1) a method comprising adding cellooligosaccharides and components simultaneously and mixing or dispersing them, 2) a method comprising mixing or dispersing cellooligosaccharides and specific components beforehand, then adding other components, and mixing or dispersing them, or 3) a method comprising mixing or dispersing two or more components beforehand, then adding cellooligosaccharides, and mixing or dispersing them may be used, or these addition methods may be used in combination.

These components may be continuously added or input in a batch using a small suction transport device, a pneumatic transport device, a bucket conveyor, a pressure feed transport device, a vacuum conveyor, an oscillating quantitative feeder, a spray, a funnel, or the like as a device used here. Furthermore, the method for mixing components is not particularly limited so long as it is a commonly used method, but container rotating blenders such as V-type, W-type, double cone type, and container tucked type blenders, or stirring blenders such as high-speed stirring type, universal stirring, ribbon type, pug type, or Nauta blenders, high-speed fluidized blenders, drum blenders, or fluidized bed blenders may be used. Furthermore, container shaking blenders such as a shaker can be used.

The dispersion method is not particularly limited so long as it is a commonly used dispersion method, but stirring mixing methods using a stirring wing using one-direction rotating type such as a portable mixer, a stereomixer, and a lateral mixer, a multiaxial rotating type, a reciprocating reversing type, a vertical movement type, a rotation+vertical movement type, and a pipeline type, jet stirring mixing methods such as a line mixer, stirring mixing methods using a gas blowing-in type, a high shear homogenizer, a high pressure homogenizer, an ultrasonic homogenizer, or the like, container shaking mixing methods using a shaker, and the like may be used, or methods using these in combination may be employed.

Furthermore, in the above-described mixture or dispersion, the order of adding an aqueous medium obtained by adding a surfactant, a thickening agent, or a gelatinization agent to water or organic solvent as required is not particularly limited, but 1) a method comprising adding an aqueous medium to cellooligosaccharides beforehand, dissolving or dispersing it, then adding other components, 2) a method comprising adding an aqueous medium to components beforehand, dissolving or dispersing it, then adding cellooligosaccharides, or 3) a method comprising mixing or dispersing cellooligosaccharides and components beforehand, then adding an aqueous medium, or combination methods of these may be used. Liquid foods or drugs such as aqueous solutions, dispersions, or lotions, or semisolid foods or drugs such as pastes or gels obtained here may be dried and subjected to an industrial process such as granulation, coating, or molding, if necessary.

The granulation or coating method is not particularly limited so long as it is a known method, but stirring and fluidized bed methods may be used, or combination methods thereof may be used. Examples of stirring granulation devices include stirring devices such as one-direction rotating types such as a portable mixer, a stereomixer, and a lateral mixer, a multiaxial rotating type, a reciprocating reversing type, a vertical movement type, and a rotation+vertical movement type. Examples of the fluidized bed type include an upper jet type, a center jet type, a lower jet type, combinations with stirring types, a central tin jet, a wurster type, and so forth. Furthermore, dry granulation using a roller compactor may be performed.

For coating, granulation products are obtained beforehand and may be subjected to a known coating method, or may be further subjected to another coating to obtain multiple layers after coating. The method for jetting a coating agent may be any of a method of jetting an active ingredient solution or dispersion using a pressure nozzle, two-fluid nozzle, fourfluid nozzle, rotating disk, ultrasonic nozzle, or the like or a method of adding an active ingredient solution or dispersion dropwise from a tubular nozzle. When an active ingredient solution or dispersion is added, laminating or coating to layer an active ingredient on the cellooligosaccharide particle surface may be performed, or it may be carried by a cellooligosaccharide, or a mixture of cellooligosaccharides and other components may be granulated in a matrix using a component solution or dispersion as a coupling liquid Layering or coating has similar effects whether it is wet or dry.

The molding method is not particularly limited so long as it is a commonly used method, but a mold may be used, or known molding methods such as compression, melting, jetting, and rolling can be applied. Combination method thereof may be used. Examples of the molding machine used herein include a compressed molding machine, a melt molding machine, a jet molding machine, a rolling molding machine, and so forth, and known molding machines such as molding machines for production of confectioneries, cosmetics, or drugs, a cooked rice molding machine, a compressed molding machine, a machine for wrapping fillings, a minced and steamed fish maker, a Chinese dumpling/bun molding machine, and a compressed molding machine for foundation base material can be used. In particular, compressed molding may be performed by a method of compression molding into a desired shape using a mold or a method of compression molding in a sheet beforehand and then cutting into a desired shape. As a compression molding machine, for example, a static pressure press, roller presses such as a bricketing roller press and a smooth roller press, and compressors such as a single punch tablet press and a rotary tablet press can be used.

Examples of the components used in the above-described cellooligosaccharide composition will be described below.

For example, as food materials or additives used therein, if necessary, preservatives and storable duration improving agents, antioxidants, sweeteners, coloring matters, emulsifiers, thickening agents, quality improving agents, seasonings, acidifiers, nutrient supplements, spices and herbs, food flavors, enzymes, and the like may be added in addition to the cellooligosaccharides of the present invention. Each of these food materials or additives may be used solely, or two or more thereof may be used in combination.

Examples of the preservatives and storable duration improving agents include compounds classified as preservatives and storable duration improving agents in "Japanese Standards of Food Additives" published by Hirokawa-Shoten Ltd.) such as sorbic acid, potassium sorbate, benzoic acid, sodium benzoate, p-hydroxybenzoate, dihydrosodium acetate, propionic acid, propionates, acetic acid, sodium acetate, glycine, ethyl alcohol, polylysine, protamine, lysozyme, pectin degradation products, alanine, thiamin lauryl sulfate, yucca foam extract, chitosan, and propylene glycol.

Examples of the antioxidants include compounds classified as antioxidants in "Japanese Standards of Food Additives" (published by Hirokawa-Shoten Ltd.) such as butylhydroxyanisole, butylated hydroxytoluene, vitamin C, sodium ascorbate, erythorbic acid, sodium erythorbate, and vitamin E.

Examples of the sweeteners include compounds classified as sweeteners in "Japanese Standards of Food Additives" (published by Hirokawa-Shoten Ltd. such as saccharin, licorice, stevia, aspartame, sucralose, acesulfame potassium, fructose, panose, trehalose, xylitol, erythritol, sorbitol, lactitol, maltitol, reduced paratinose, reduced starch syrup, mannitol, coupling sugar, fructooligosaccharide, galactooligosaccharide, emulsified oligosaccharide, nigerooligosaccharide, xylooligosaccharide, maltooligosaccharide, isomaltooligosaccharide, soybean oligosaccharide, paratinose, paratinose oligosaccharide, and raffinose.

Examples of the coloring matters include edible tar dyes such as Red Nos. 2, 3, 40, 102, 105, and 106, Yellow Nos. 4 and 5, Blue Nos. 1, 2, Red No. 3 lake, Red No. 40 lake, Yellow No. 4 lake, Yellow No. 5 lake, Blue No. 1 lake, and Blue No. 2 lake, and dyes classified as coloring matters in "Japanese Standards of Food Additives" (published by Hirokawa-Shoten Ltd.) such as carotene dyes, annatto dyes, paprika dyes, cochineal dyes, gardenia dyes, safflower dyes, monascus dyes, beet red, xanthine dyes, spirulira dyes, anthocyanin dyes, and caramel.

Examples of the emulsifiers include those classified as emulsifiers in "Japanese Standards of Food Additives" (published by Hirokawa-Shoten Ltd.) such as glycerine fatty acid ester, sucrose fatty acid ester, sorbitan fatty acid ester, propylene glycol fatty acid ester, saponin, and lecithin.

Examples of the thickening agents include compounds classified as thickening agents in "Japanese Standards of Food Additives" (published by Hirokawa-Shoten Ltd.), such as guar gum, locust bean gum, carrageenan, agar, pectin, xanthan gum, gellan gum, gum arabic, glucomannan, algic acid, psyllium seed gum, gelatin, methylcellulose, curdlan, crystalline cellulose, carboxymethylcellulose, tamarind gum, and non-digestible dextrin.

Examples of the quality improving agents include compounds classified as quality improving agents 1 in "Japanese Standards of Food Additives" (published by Hirokawa-Shoten Ltd.) such as soybean protein, wheat protein, casein, caseinates, lactoprotein concentrate, lactose, and phosphates.

Examples of the seasonings include compounds classified as seasonings in "Japanese Standards of Food Additives" (published by Hirokawa-Shoten Ltd.) such as monosodium glutamate, nucleic acid seasonings meat extracts, fish extracts, vegetable extracts, yeast extracts, amino acid seasonings, fish sauce seasoning, rich taste seasonings, and seasoning oils.

Examples of the acidifiers include compounds classified as acidifiers in "Japanese Standards of Food Additives" (published by Hirokawa-Shoten Ltd.) such as citric acid, lactic acid, malic acid, tartaric acid, fumaric acid, succinic acid, adipic acid, and gluconic acid.

Examples of the nutrient supplements include compounds classified as nutrient supplements in "Japanese Standards of Food Additives" (published by Hirokawa-Shoten Ltd.) such as vitamin A, vitamin B family, vitamin D, vitamin K, carotenoid, beef bone calcium, eggshell calcium, calcium carbonate, pearl oyster, pearl powder, oyster shell, scallop shell calcium, coral powder, fish bone powder, dolomite, magnesium chloride, yeast minerals, heme iron, deep water, salt water lake water minerals, and seaweed/plant-derived minerals.

Examples of the spices and herbs include compounds classified as spices and herbs in "Japanese Standards of Food Additives" (published by Hirokawa-Shoten Ltd.) such as peppers, chili peppers, pimenta, vanilla bean, cinnamon, clove, nutmeg, nutmeg flower, cardamom, anise, large fennel, coriander, cumin, caraway, fennel, juniper, ginger, saffron, turmeric, laurel, thyme, and curry.

Examples of the edible flavors include compounds classified as edible flavors in "Japanese Standards of Food Additives" (published by Hirokawa-Shoten Ltd.) such as fruit flavors such as peach flavor, orange flavor, and lemon flavor, aroma flavors, sugar flavors such as maltol and furaneol, flavor enhancers such as sotolone, flavonoids, polyphenols such as cacao mass, precursor flavors, meat flavors, coffee flavors, milk flavor, menthols, and decalactones.

Examples of the enzymes include compounds classified as enzymes in "Japanese Standards of Food Additives" (published by Hirokawa-Shoten Ltd.) such as α-amylase, β-amylase, glucose isomerase, protease, rennet, pancreatin, papine, lipase, cellulase, bromelain, pectinase, lysozyme, hesperidinase, pullulanase, transglutaminase, hemicellulase, β-galactanase, lactase, dextranase, invertase, catalase, deaminase, urease, tannase, lipoxygenase, and adenyl aminase.

Examples of drug medicinal components or additives used therein will be shown below.

Examples of the drug medicinal components include transdermally or orally administered agents such as antipyretic analgesic antiphlogisthics, sedative hypnotics, sleep-averting drugs, antidinics, analgesics for pediatric use, stomachics, antacids, digestives, cardiotonics, antiarrhythmic drugs, hypotensive drugs, vasodilators, diuretics, anti-ulcer drugs, drugs regulating intestinal functions, therapeutic agents for osteoporosis, antiussive expectrorants, anti-asthma drugs, antibacterial agents, pollakiuria improving agents, revitalizers, and vitamin agents. Each of medicinal components may be used solely, or two or more thereof may be used in combination.

Furthermore, examples of additives used for drugs include excipients, disintegrating agents, binders, fluidizers, lubricants, flavoring agents, flavors, coloring materials, sweeteners, solvents, oils and fats, thickening agents, surfactants, gelatinizing agents, and so forth. Each of these additives may be used solely, or two or more thereof may be used in combination.

Examples of the excipients include compounds classified as excipients in "Japanese Pharmacopoeia" (published by Hirokawa-Shoten Ltd.) and "Encyclopedia of Drug Additives" (Yakuji Nippo Limited) such as starch acrylate, L-aspartic acid, aminoethylsulfonic acid, aminoacetic acid, candy (powder), gum arabic, powdered gum arabic, alginic acid, sodium alginate, a starch, inositol, ethylcellulose, ethylene vinyl acetate copolymer, sodium chloride, olive oil, kaolin, cacao butter, casein, fructose, pumice particles, carmellose, carmellose sodium, hydrous silicon dioxide, dry yeast, dry aluminium hydroxide gel, dry sodium sulfate, dry magnesium sulfate, agar, powdered agar, xylitol, citric acid, sodium citrate, disodium citrate, glycerine, calcium glycerophosphate, sodium gluconate, L-glutamine, clay, clay particles, croscarmellose sodium, cross-linked polyvinylpyrrolidone, magnesium aluminosilicate, calcium silicate, magnesium silicate, light anhydrous silicic acid, light liquid paraffin, cinnamon bark powder, crystalline cellulose, crystalline cellulose/carmellose sodium, crystalline cellulose (particles), brown rice malt, synthetic aluminium silicate, synthetic hydrotalcite, sesame oil, wheat powder, wheat starch, wheat germ powder, rice powder, rice starch, potassium acetate, calcium acetate, cellulose acetate phthalate, safflower oil, bleached beeswax, zinc oxide, titanium oxide, magnesium oxide, β-cyclodextrin, dihydroxyaluminium aminoacetata, 2,6-di-butyl-4-methyl phenol, dimethylpolysiloxane, tartaric acid, potassium hydrogen tartrate, exciccated gypsum, sucrose fatty acid ester, alumina/magnesium hydroxide, aluminium hydroxide gel, aluminum hydroxide/sodium hydrogencarbonate coprecipitates, magnesium hydroxide, squalane, stearyl alcohol, stearic acid, calcium stearate, polyoxyl stearate, magnesium stearate, Sterotex HM, purified gelatin, purified shellac, purified sucrose, purified sucrose spherical granules, cetostearyl alcohol, cetopolyethylene glycol, gelatin, sorbitan fatty acid ester, D-sorbitol, calcium phosphate tribasic, soybean oil, soybean unsaponifiables, soybean lecithin, powdered skim milk, talc, ammonium carbonate, calcium carbonate, magnesium carbonate, neutral anhydrous sodium sulfate, low-substituted hydroxypropylcellulose, dextran, dextrin, natural aluminum silicate, maize starch, powdered tragacanth, silicon dioxide, lactic acid calcium, lactose, white Vaseline, sucrose, sucrose/starch spherical granules, green rye leaf extract powder, rye malt green soup dry powder, honey, paraffin, potato starch, semidigested starch, human serum albumin, hydroxypropyl starch, hydroxypropylcellulose, hydroxypropyl methylcellulose phthalate, phytic acid, glucose, glucose hydrate, partial alpha starch, Pullulan, propylene glycol, powdered reduced maltose starch syrup, powdered cellulose, pectin, bentonite, sodium polyacrylate, polyoxyethylene alkyl ether, polyoxyethylene hydrogenated caster oil, polyoxyethylene poly oxypropylene glycol, sodium polystyrene sulfonate, polyvinylacetaldiethyl aminnacetate, polyethylene glycol, maltitol, maltose, D-mannitol, starch syrup, isopropyl myristate, anhydrous lactose, anhydrous calcium hydrogen phosphate, granulated anhydrous calcium phosphate, magnesium aluminometasilicate, methylcellulose, cotton seed powder, cottonseed oil, Japan tallow, monoaluminium stearate, glycerine monostearate, sorbitan monostearate, medicinal charcoal, peanut oil, aluminium sulfate, calcium sulfate, granulated maize starch, liquid paraffin, dl-malic acid, phosphoric acid-hydrogen calcium, calcium hydrogen phosphate, granulated calcium hydrogen phosphate, sodium hydrogen phosphate, potassium dihydrogen phosphate, calcium dihydrogen phosphate, and sodium dihydrogen phosphate. Each of these may be used solely, or two or more thereof may be used in combination.

Examples of the disintegrating agents include compounds classified as disintegrating agents in "Japanese Pharmacopoeia" (published by Hirokawa-Shoten Ltd.) and "Encyclopedia of Drug Additives" (Yakuji Nippo Limited) such as celluloses such as croscarmellose sodium, carmellose, carmellose calcium, carmellose sodium, and low-substituted hydroxypropylcellulose, starches such as carboxymethyl starch sodium, hydroxypropyl starch, rice starch, wheat starch, maize starch, potato starch, and partial alpha starch, and synthetic polymers such as cross-linked polyvinylpyrrolidone and cross-linked polyvinylpyrrolidone copolymer. One selected from the above compounds may be used solely, or two or more thereof may be used in combination.

Examples of the binders include compounds classified as binders in "Japanese Pharmacopoeia" (published by Hirokawa-Shoten Ltd.) and "Encyclopedia of Drug Additives" (Yakuji Nippo Limited) such as saccharides such as sucrose, glucose, lactose, and fructose, sugar alcohols such as mannitol, xylitol, maltitol, erythritol, and sorbitol, water-soluble polysaccharides such as gelatin, Pullulan, carrageenan, locust bean gum, agar, glucomannan, xanthan gum, tamarind gum, pectin, sodium alginate, and gum arabic, celluloses such as crystalline cellulose, powder cellulose, hydroxypropylcellulose, and methylcellulose, starches such as alpha starch and starch paste, synthetic polymers such as polyvinylpyrrolidone, carboxyvinyl polymers, and polyvinyl alcohol, and inorganic compounds such as calcium hydrogen phosphate, calcium carbonate, synthetic hydrotalcite, and magnesium aluminosilicate. One selected from the above may be used solely, or two or more thereof may be used in combination.

Examples of the fluidizers include compounds classified as fluidizers in "Encyclopedia of Drug Additives" (Yakuji Nippo Limited) such as silicon compounds such as hydrous silicon dioxide and light anhydrous silicic acid. One selected from the above compounds may be used solely, or two or more thereof may be used n combination.

Examples of the lubricants include compounds classified as lubricants in "Japanese Pharmacopoeia" (published by Hirokawa-Shoten Ltd.) and "Encyclopedia of Drug Additives" (Yakuji Nippo Limited) such as magnesium stearate, calcium stearate, stearic acid, sucrose fatty acid ester, and talc. One selected from the above compounds may be used solely, or two or more thereof may be used in combination.

Examples of the flavoring agents include compounds classified as flavoring agents in "Japanese Pharmacopoeia" (published by Hirokawa-Shoten Ltd.) and "Encyclopedia of Drug Additives" (Yakuji Nippo Limited) such as glutamic acid, fumaric acid, succinic acid, citric acid, sodium citrate, tartaric acid, malic acid, ascorbic acid, sodium chloride, and 1-menthol. One selected from the above compounds may be used solely, or two or more thereof may be used in combination.

Examples of the flavors include compounds classified as flavoring agents or flavors in "Japanese Pharmacopoeia" (published by Hirokawa-Shoten Ltd.) and "Encyclopedia of Drug Additives" (Yakuji Nippo Limited) such as orange, vanilla, strawberry, yoghurt, menthol, oils such as fennel oil, cinnamon bark oil, orange peel oil, and peppermint oil, and green tea powder. One selected from the above compounds may be used solely, or two or more thereof may be used in combination.

Examples of the coloring materials include compounds classified as coloring materials in "Japanese Pharmacopoeia" (published by Hirokawa-Shoten Ltd.) and "Encyclopedia of Drug Additives" (Yakuji Nippo Limited) such as edible dyes such as edible Red No. 3, edible Yellow No. 5, and edible Blue No. 1, sodium copper chlorophyllin, titanium oxide, and riboflavin. One selected from the above compounds may be used solely, or two or more thereof may be used in combination.

Examples of the sweeteners include compounds classified as sweeteners in "Japanese Pharmacopoeia" (published by Hirokawa-Shoten Ltd.) and "Encyclopedia of Drug Additives" (Yakuji Nippo Limited) such as aspartame, saccharin, dipotassium glycyrrhizinate, stevia, maltose, maltitol, starch syrup, and powdered sweet hydrangea leaves. One selected from the above compounds may be used solely, or two or more thereof may be used in combination.

The solvents are not particularly limited so long as they are used in drugs, but examples thereof include compounds classified as solvents in "Japanese Pharmacopoesa" (published by Hirokawa-Shoten Ltd.) and "Encyclopedia of Drug Additives" (Yakuji Nippo Limited) such as alcohols such as methanol and ethanol and ketones such as acetone. Each of these compounds may be used solely, or two or more thereof may be used in combination.

Examples of the oils and fats include oils and fats described in "Japanese Pharmacopoeia" (published by Hirokawa-Shoten Ltd.) and "Encyclopedia of Drug Additives" (Yakuji Nippo Limited) such as paraffins such as monoglyceride stearate, triglyceride stearate, sucrose stearic acid ester, and liquid paraffin, hydrogenated oils such as Carunauba wax and hydrogenated caster oil, caster oil, stearic acid, stearyl alcohol, and polyethylene glycol. Each of these compounds may be used solely, or two or more thereof may be used in combination.

Examples of the thickening agents include thickening agents described in "Japanese Pharmacopoeia" (published by Hirokawa-Shoten Ltd.) and "Encyclopedia of Drug Additives" (Yakuji Nippo Limited), such as hydroxypropylcellulose, hydroxypropylmethylcellulose, polyacrylic acid, carboxyvinyl polymers, polyethylene glycol, polyvinyl alcohol, polyvinylpyrrolidone, methylcellulose, ethylcellulose, gum arabic, and starch paste. Each of these compounds may be used solely, or two or more thereof may be used in combination.

Examples of the surfactants include compounds classified as surfactants in "Japanese Pharmacopoeia" (published by Hirokawa-Shoten Ltd.) and "Encyclopedia of Drug Additives" Yakuji Nippo Limited) such as phospholipids, glycerine fatty acid esters, polyethylene glycol fatty acid esters, sorbitan fatty acid esters, polyoxyethylene hydrogenated caster oil, polyoxyethylene cetyl ether, polyoxyethylene stearyl ether, polyoxyethylene nonylphenyl ether, polyoxyethylene polyoxypropylene glycol, polyoxyethylene sorbitan acid monolaurate, polysorbate, sorbitan monooleate, glyceride monostearate, monooxyethylene sorbitan monopalmitate, monooxyethylene sorbitan monostearate, polyoxyethylene sorbitan monooleate, sorbitan monopalmitate, and lauryl sodium sulfate. Each of these compounds may be used solely, or two or more thereof may be used in combination.

Examples of the gelatinizing agents include compounds classified as gelatinizing agents in "Japanese Pharmacopoeia" (published by Hirokawa-Shoten Ltd.) and "Encyclopedia of Drug Additives" (Yakuji Nippo Limited) such as animal gelatinizing agents such as gelatin, vegetable polysaccharides such as agar, xanthan gum, guar gum, gum arabic, curdlan, locust bean gum, carboxymethylcellulose, hydroxyethylcellulose, cellulose, and microcrystalline cellulose, and chemical synthetic polymers such as polyvinylpyrrolidone. Each of these may be used solely, or two or more thereof may be used in combination.

For example, as cosmetic materials or additives used therein, moisturizing agents, amino acids, vitamins, hydrocarbons, higher fatty acids, esters, silicone, surfactants, pH modifiers, and water may be added in addition to the cellooligosaccharide composition of the present invention, if necessary. Each of these cosmetic materials or additives may be used solely, or two or more thereof may be used in combination.

Examples of the moisturizing agents include compounds classified as moisturizing agents in "Japanese Standards of Cosmetic Ingredients (JSCI)" and "Comprehensive Licensing Standards of Cosmetics by Category" (both published by Yakuji Nippo Limited) such as polyethylene glycol, propylene glycol, glycerine, 1,3-butylene glycol, sorbitol, maltitol, chondroitin sulfuric acid, collagen, sodium lactate, dl-pyrrolidinecarboxylic acid, coix seed extract, and so-bean lecithin.

Examples of the amino acids include compounds classified as amino acids in "Japanese Standards of Cosmetic ingredients (JSCI)" and "Comprehensive Licensing Standards of Cosmetics by Category" (both published by Yakuji Nippo Limited) such as neutral amino acids such as glycine, alanine, valine, leucine, isoleucine, serine, threonine, tryptophan, cystine, methionine, proline, hydroxyproline, glutamine, and asparagine, acidic amino acids such as aspartic acid and glutamic acid, and basic amino acids such as arginine, histidine, lysine, hydroxylysine.

Preferable examples of vitamins include vitamin A, vitamin D, vitamin E, vitamin K, vitamin $B_1$, vitamin $B_2$, vitamin $B_6$, vitamin $B_{12}$, folic acid, niacin, pantothenic acid, biotin, and vitamin C can be used. Examples of vitamin A include retinol, retinal, retinoic acid, 3-dehydroretinol, 3-dehydroretinal, 3-dehydroretinoic acid, and β-catechin. Examples of vitamin D include ergocalciferol (D2), cholecalciferol (D3), ergosterol, and 7-hydrocholesterol. Examples of vitamin E include α-tocopherol. Examples of vitamin K include phylloquinone (K1), menaquinone (K2), and menadione (K3). Examples of vitamin $B_1$ include thiamin (aneurine). Examples of vitamin $B_2$ include riboflavin. Examples of vitamin $B_6$ include pyridoxine, pyridoxal, and pyridoxamine. Examples of vitamin $B_{12}$ include cobalamin. Examples of folio acid include pteroylglutamic acid. Examples of niacin include nicotinic acid and nicotinamide (nicotinic acid amide). Examples of vitamin C include ascorbic acid. Each of these vitamins may be used solely, or two or more thereof may be used in combination. Furthermore, these vitamins may be lipid-soluble or water-soluble, and it is preferable to use those commonly used for cosmetics, drugs, quasi-drugs, and foods. It is preferable to use vitamins classified in "Japanese Pharmacopoeia" (published by Hirokawa-Shoten Ltd., and "Japanese Standards of Cosmetic ingredients (JSCI)" (Yakuji Nippo Limited).

Examples of the hydrocarbons include compounds classified as hydrocarbons in "Japanese Standards of Cosmetic Ingredients (JSCI)" and "Comprehensive Licensing Standards of Cosmetics by Category" (both published by Yakuji Nippo Limited) such as liquid paraffin, paraffin, squalane, and Vaseline.

Examples of the higher fatty acids include compounds classified as higher fatty acids in "Japanese Standards of Cosmetic Ingredients" (published by Yakuji Nippo Limited) such as lauric acid, myristic acid, palmitic acid, stearic acid, beheric acid, oleic acid, hydroxystearic acid, undecylenic acid, isostearic acid, linoleic acid, linolenic acid, eicosapentaenoic acid, and docosahexaenoic acid.

Examples of the esters include compounds classified as esters in "Japanese Standards of Cosmetic Ingredients (JSCI)" and "Comprehensive Licensing Standards of Cosmetics by Category" (both published by Yakuji Nippo Limited) such as isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl hydroxystearate, ethylene glycol di-2-ethylhexylate, dipentaerythritol fatty acid ester, N-alkylglycol monoisostearate, neopentylglycol dicaprate, diisostearyl malate, glycerine di-2-heptyl undecanoate, glycerine tri-2-ethylhexylate, trimethylolpropane triisostearate, cetyl2-ethyl hexanoate, 2-ethylhexyl palmitate, glycerine trimyristate, glyceride tri-2-heptyl undecanoate, 2-hexyldecyl myristate, 2-hexyldecyl palmitate, 2-hexyldecyl adipate, diisopropyl sebacate, 2-ethylhexyl succinate, and triethyl citrate.

Examples of the silicones include compounds classified as silicones in "Japanese Standards of Cosmetic Ingredients (JSCI)" and "Comprehensive Licensing Standards of Cosmetics by Category" (both published by Yakuji Nippo Limited) such as chain polysiloxanes such as dimethylpolysiloxane and methylphenylpolysiloxane, cyclic siloxanes such as decamethylcyclopentasiloxane and dodecamethylcyclohexasiloxane, and silicone resins having a cross-linked mesh structure.

Examples of the surfactants include compounds classified as surfactants in "Japanese Standards of Cosmetic Ingredients (JSCI)" and "Comprehensive Licensing Standards of Cosmetics by Category" both published by Yakuji Nippo Limited) such as, in addition to anionic surfactants including acylamino acid salts such as acylglutamic acid salts, higher alkyl sulfuric acid ester salts such as sodium laurate, sodium palmitate, sodium lauryl sulfate, and potassium lauryl sulfate, alkyl ether sulfuric acid ester salts such as polyoxyethylene lauryl sulfate triethanolamine and sodium lauryl polyoxyethylene sulfate, and N-acyl sarcosine acid salts such as lauroylsarcosine sodium, cationic surfactants such as alkyl trimethyl ammonium salts such as stearyl trimethyl ammonium chloride and lauryl trimethyl ammonium chloride, distearyl dimethyl ammonium chloride, dialkyl dimethyl ammonium salts, alkyl pyridinium salts such as (N,N'-dimethyl-3,5-methylenepiperidinium) chloride and cetyl pyridinium chloride, alkyl amine salts such as alkyl quaternary ammonium salts and polyoxyethylene alkyl amides, polyamine fatty acid derivatives, and amyl alcohol fatty acid derivatives, imidazoline ampholytic surfactants such as 2-undecyl-N,N,N-(hydroxyethylcarboxymethyl-2-imidazoline sodium and 2-cocoil-2-imidazoliniumhydroxide-1-carboxymethyloxy-2-sodium salts, ampholytic surfactants such as betaine ampholytic surfactants such as 2-heptadecyl-N-carboxymethyl-N-hydroxyethylimidazolinium betaines, lauryl dimethylaminoacetic acid betaines, alkyl betaines, amide betaines, and sulfobetaines, and nonionic surfactants including sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate, glycerine monostearate, glycerine polyglycerin fatty acids such as glycerine α,α'-oleate pyroglutamate, and glycerine monostearate malate, propylene glycol fatty acid esters such as propylene glycol monostearate, hydrogenated caster oil derivatives, glycerine alkyl ethers, polyoxyethylene-sorbitan fatty acid esters such as polyoxyethylene-sorbitan monostearate, polyoxyethylene-sorbitan monooleate, and polyoxyethylene-sorbitan tetraoleate, polyoxyethylene-glycerine fatty acid esters such as polyoxyethylene-sorbit monolaurate, polyoxyethylene-sorbit monooleate, polyoxyethylene-sorbit pentaoleate, polyoxyethylene-sorbit monostearate, polyoxyethylene-glycerine monoisostearate, and polyoxyethylene-glycerine triisostearate, polyoxyethylene fatty acid esters such as polyoxyethylene monooleate, polyoxyethylene distearate, polyoxyethylene monodioleate, and ethylene glycol distearate, and polyoxyethylene caster oil hydrogenated caster oil derivatives such as polyoxyethylene hydrogenated caster oil, polyoxyethylene caster oil, polyoxyethylene hydrogenated caster oil monoisostearate, polyoxyethylene hydrogenated caster oil triisostearate, polyoxyethylene hydrogenated caster oil monopyroglutamate monoisostearate diester, and polyoxyethylene hydrogenated caster oil maleate.

Examples of the pH modifier include buffers described in "Japanese Standards of Cosmetic Ingredients" and "Comprehensive Licensing Standards of Cosmetics by Category" (both published by Yakuji hippo Limited) such as lactic acid-sodium lactate, citric acid-sodium citrate, phosphoric acid-sodium phosphate, acetic acid-sodium acetate, and McIlvaine reagent.

Examples of the cellooligosaccharide containing food of the present invention include gels such as jelly, cream caramels, and yoghurts, seasonings such as mayonnaise, dressings, sauces, basting sauces, soups, and processed vegetable products, retorable foods such as curries, hashed beefs, meat sauces, stews, and soups, chilled foods, processed meat products such as hamburger steaks, bacons, sausages, salami sausages, and hams, fish paste products such as minced and steamed fish products, fish sausages, fish hams and sausages, and fried minced and steamed fish products, processed wheat products such as breads, raw noodles, dried noodles, macaronis, spaghettis, Chinese bun pastries, cake mixes, premixes, while sauces, and pastries for jiaozis and spring rolls, canned and bottled foods such as curries, sauces, soups, fish boiled in soy sauce, and Jams, confectioneries such as candies, lozenges, tablet confectioneries, chocolates, biscuits, cookies, rice crackers, Japanese and Western cakes, unbaked cakes, snacks, sugar confectioneries, and cream caramels, deep-fried foods, cooked and processed foods such as croquettes, jiaozis, and Chinese buns, and pastes such as vegetable pastes, minced meats, fruit pastes, and seafood pastes. Furthermore, examples thereof include dairy products such as ice creams, ice milks, lacto-ices, whipping creams, confluents, butters, yoghurts, cheeses, and white sauces, processed oils and fats such as margarines, fat spreads, and shortenings, and so forth. Furthermore, it may be used in carbonated beverages such as colas, carbonated fruit beverages, alcoholic fruit beverages, fruit beverages mixed with dairy products, fruit juices, fruit-containing beverages, lactic acid beverages or milk beverages such as milk drinks, coffees, cow's milks, soy milks, cocoa milks, fruit milks, and yogurts, tea beverages such as natural leaf teas, oolong teas, green powdered teas, black teas, and the like.

Examples of the cellooligosaccharide containing drugs and quasi-drugs of the present invention include solid formulations such as tablets, powders, subtilized granules, granules, extracts, and pills. In addition to the above-mentioned solid formulations, those utilized in confectioneries, foods such as health foods, texture improving agents, dietary fiber nutrient supplements, solid foundations, bath agents, veterinary drugs, diagnostic agents, agricultural chemicals, fertilizers, ceramic catalysts, and the like are also included in the present invention.

Examples of cosmetics and quasi-drugs include cosmetics described in "Cosmetic Science Guide Book" (edited by Society of Cosmetic Chemists of Japan, published by Yakuji Nippo Limited) such as hairdressing products such as perfumed oils, hair oils, greasing oils, combing oils, oils for sidelock, set lotions, hair sticks, hair creams, pomades, hair sprays, and hair liquids, hair growth stimulants such as hair tonics, hair treatments, and hair lotions, hair coloring agents such as color spray and color conditioner, agents for scalp, hair wash agents such as shampoo powders and shampoos, conditioners such as hair conditioners, oil conditioners, cream conditioners, body conditioners, and facial conditioners, facial cleansers such cleansing creams, face-wash creams, cleansing milks, cleansing lotions, and soap powders, creams such as packs, oily creams, neutral creams, and weak acidic creams, lotions such as milk lotion and skin milks, face lotions such as face lotions for dry skin, face lotions for normal skin, face lotions for oily skin, male face lotions, male lotions, and aftershave lotions, makeup bases, foundations, face powders, lip colors such as lip colors, lipsticks, lip rouges, lip glosses, and lip creams, cosmetics for eyebrows, eyes, and cheeks such as eye shadows, eyeliners, eye creams, eyebrow paints, eyelash cosmetics, eye makeup removers, eye makeups, rouges, eyebrow pencils, eyebrow brushes, and mascaras, nail cosmetics such as nail enamels, nail creams, manicures, pedicures, enamel removers, and nail polish removers, colognes such as perfumes, eau de colognes, perfumed colognes, and eau de toilettes, bath cosmetics such as bath salts and bath oils, cosmetic oils containing olive oil, camellia oil, baby oil, or the like, suntan-control cosmetics, cold creams, sunscreen cosmetics, shaving creams such as shaving creams and shaving foams, pre-shave cosmetics, nursery powders such as talcum powders, body powders bath powders, and perfume powders, and so forth, and they may be used for compounds classified as these cosmetics and quasi-drugs.

Since the cellooligosaccharide-containing composition of the present invention is expected to have various bioactivities such as improvement of the enteric bacteria flora, activation of lactic bacteria, lactobacillus, and the like, decreasing of blood sugar levels, blood insulin concentrations, blood cholesterol concentrations, and body fat rates, promotion of lipid and carbohydrate metabolisms, improvement of bowel movement and fecal odor, and prevention of dental caries, in addition to the above-mentioned usual use for foods, it may be used for functional foods, health foods, diet foods, drugs, quasi-drugs, and the like as a bioactive substance.

Furthermore, since the cellooligosaccharide composition of the present invention has effects of improving the skin barrier function and the indigenous dermal bacteria flora, It may be used for functional cosmetics, quasi-drugs, and drugs for prevention or improvement of damaged skin such as dermatitis and dry skin.

EXAMPLES

The present invention will be explained with reference to the following examples. However the scope of the present invention is not limited to these examples.

Preparation Example 1

*Trichoderma reesei* NBRC13-29 was inoculated in a nutrient agar medium and cultured 37° C. for 7 days, and one loopful of spores were scooped from the medium surface, inoculated in a medium obtained by suspending and dissolving all of 1 g of polypeptone, 0.5 g of yeast extract, 2 g of monopotassium phosphate, 1.5 g of ammonium sulfate, 0.3 g of magnesium sulfate, 0.3 g of calcium chloride, 1 mL of trace elements (obtained by dissolving all of 6 mg of boric acid, 26 mg of ammonium molybdate tetrahydrate, 100 mg of iron(III) chloride hexahydrate, 40 mg of copper sulfate pentahydrate, 8 mg of manganese sulfate tetrahydrate, and 200 mg of zinc sulfate heptahydrate in 100 mL of purified water), 1 mL of adekanol, and 10 g of crystalline cellulose (manufactured by Asahi Kasei Chemicals Corporation, trade name PH-101) in 1 L of purified water, and aerobically cultured with stirring at 28° C. for 5 days. During the culture, the medium was adjusted to pH 2.8 to 4.7 using aqueous sodium hydroxide. After the culture, the solution was centrifuged, the supernatant was collected and subjected to sterile filtration using a microfiltration membrane having a mesh size of 0.46 µm, and the filtrate was concentrated to 10% of the original volume using an ultrafiltration membrane having a molecular weight cutoff of 13,000 (manufactured by Asahi Kasei Chemicals Corporation, trade name Microza Pencil-Type Module ACP-0013) to obtain a crude enzyme.

Subsequently, a commercially available dissolving pulp derived from a coniferous tree was hydrolyzed under conditions of hydrolysis with aqueous hydrochloric acid containing hydrochloric acid at a concentration of 0.4% at 120° C. for 1 hour, and acid-insoluble residues were washed and filtered to obtain a wet cake. This wet cake was converted to a water dispersion containing cellulose at a concentration of 10% and subjected to compression/grinding treatment using a super performance dispersing/wet-pulverizing machine (manufactured by Ashizawa Co., trade name Pearl Mill RT using $\phi$1 mm zirconium beads, the filling rate 80%) to obtain a cellulose microparticle dispersion (average degree of polymerization 220, diethyl ether-soluble matter content 0.7%, average particle size 0.7 µm, colloidal component content 51.5%).

This ground cellulose and the crude enzyme were suspended and dissolved in a 50 mM acetic acid-sodium acetate buffer (pH 4.5) to make 1000 mL as a total volume so that the ground cellulose content should be 2% by mass, and the crude enzyme should have a protein concentration of 0.25%, and poured in a glass flask. This glass flask was placed in a water bath at 55° C., and the solution therein was reacted for 4 hours with stirring. After completion of the reaction, 300 µL of the reaction mixture was dispensed in the state suspension, the enzyme and undegraded cellulose were removed using an ultrafiltration module molecular weight cutoff 10000), and then the saccharide concentrations were analyzed by high performance liquid chromatography. The saccharide concentrations in the reaction mixture were 0.1% by mass of cellotriose, 1.5% by mass of cellobiose, and 0.3% by mass of glucose.

This reaction mixture was filtered through an ultrafiltration membrane having a molecular weight cutoff of 13,000 (manufactured by Asahi Kasei Chemicals Corporation, trade name Microza Pencil-Type Module ACP-0013), and the obtained filtrate was deionized using a cation/anion exchange resin and distilled at 70° C. under reduced pressure to obtain an aqueous solution having 20 times higher saccharide concentrations.

Example 1

100 mL of the aqueous cellooligosaccharide solution obtained in Preparation Example 1 was poured into a 200-mL glass flask and cooled from 70° C. to 25° C. at a rate of 10° C. per hour with stirring (solubility parameter δ of the solvent 22.2). A cellooligosaccharide crystallized in the aqueous solution at 25° C. was filtered under reduced pressure, dried with a circulation drier at 40° C., pulverized with a mortar, and sifted through a sieve having a mesh size of 15 μm, and the sifted powder was sifted through a sieve having a mesh size of 45 μm to remove fire powders to obtain a cellooligosaccharide powder. 50 mg of the obtained cellooligosaccharide powder was placed in a ϕ1.1 mm cylindrical steel mortar, pressure was applied with a ϕ1.1 mm flat pestle at 150 MPa for 10 seconds, and hardness of the obtained mold was measured (average L/D 1.7, bulk density 0.43 g/mL, cellobiose content 99% by mass, content of cellotriose, cellotetraose, cellopentaose, and cellohexaose 0.1% by mass, glucose content 0.9% by mass, powder repose angle 43°, crystallization yield 50% by mass, mold hardness 67 N)

Example 2

A commercially available cellobiose manufactured by Aldrich, purity 98% by mass) was dissolved in water at 70° C. in a 200-mL glass flask at a concentration of 30% by mass to make 100 mL as a total volume, the solution was cooled from 70° C. to 25° C. at a rate of 10° C. per hour, then an isopropyl alcohol/ethanol solution of a volume mixing ratio of 50/50 was added at a ratio of 50% by mass to water at a rate of 10 g per minute, and the mixture was cooled from 70° C. to 25° C. at a rate of 10° C. per hour (solubility parameter δ of the solvent 16.6). A cellooligosaccharide crystallized in the aqueous solution was filtered under reduced pressure, dried, pulverized, and sifted in the same manner as in Example 1 to obtain a cellooligosaccharide powder. Hardness of the obtained cellooligosaccharide mold was measured in the same manner as in Example 1 (average L/D 2.3, bulk density 0.54 g/mL, cellobiose content 99% by mass, content of cellotriose, cellotetraose, cellopentaose, and cellohexaose 0.5% by mass, glucose content 0.5% by mass, powder repose angle 48°, crystallization yield 89% by mass, mold hardness 107 N)

Example 3

100 mL of the aqueous cellooligosaccharide solution obtained in Preparation Example 1 was poured into a 200-mL glass flask and cooled from 70° C. to 25° C. at a rate of 10° C. per hour with stirring, then ethanol was added at a ratio of 75% by volume to water at a rate of 10 g per minute to crystallize the mixture (solubility parameter δ of the solvent 14.5). A cellooligosaccharide crystallized in the aqueous solution was filtered under reduced pressure, dried, pulverized, and sifted in the same manner as in Example 1 to obtain a cellooligosaccharide powder. Hardness of the obtained cellooligosaccharide mold was measured in the same manner as in Example 1 (average L/D 2.5, bulk density 0.51 g/mL, cellobiose content 99.9% by mass, glucose content 0.1% by mass, powder repose angle 55°, crystallization yield 92% by mass, mold hardness 115 N)

Example 4

1 g each of the cellooligosaccharide powders used in Examples 1 to 3 was placed on a glass plate, rapeseed oil (Nissin Canola Oils was added dropwise with a burette, the mixture was kneaded after each drop, and the amount of oil retention was measured at room temperature. The end point (saturated oil absorption, was defined as the point at which oil began to soak out on the powder surface, and the oil retention was calculated by:

Oil retention=saturated oil absorption (g)/amount of cellooligosaccharide powder (g)

The oil retention of the cellooligosaccharide powder of Example 1 was 1.0 g/g, that of Example 2 was 1.1 g/g, that of Example 3 was 0.95 g/g, and all the powders showed a high oil absorbing property.

Comparative Example 1

The oil retention of a commercially available D-cellobiose powder (manufactured by Sigma Aldrich) was measured in the same manner as in Example 4. The oil retention of the commercially available D-cellobiose was 0.85.

Example 5

The moisture absorption rates of the cellooligosaccharide powders of Examples 1 to 3 were measured after allowed to stand in an environment with a relative humidity of 75% and a temperature of 40° C. for 18 hours.

Moisture absorption rate=weight increase after allowed to stand (g)/amount of cellooligosaccharide powder (g)×100(% by mass)

The moisture absorption rates of all the powders were lower than 1% by mass, and no blocking of powder or increase in the repose angle was observed.

Example 6

The residual rates after heating of the cellooligosaccharide powders of Examples 1 to 3 were determined by dissolving the cellooligosaccharide powders in McIlvaine buffer (pH 3.0) at a concentration of 1% by mass and heating the solutions at 121° C. for 20 minutes using an autoclave, and determining the saccharide composition. The residual rates of all the cellooligosaccharide powders after heating were 90% or higher, and high heat resistance/acid resistance was demonstrated.

Example 7

A commercially available potato starch was suspended in pure water at 2% by mass and heated at 95° C. for 2 hours to obtain an aqueous starch solution. Then, aqueous cellooligosaccharide solutions were prepared by dissolving the cellooligosaccharide powders obtained in Examples 1 to 3 in pure water at 6% by mass. Equal parts of the aqueous starch solution and each of the aqueous cellooligosaccharide solutions were mixed and stored at 4° C. for 12 hours, and turbidity (wavelength 660 nm) was measured before and after the storage to obtain the modification rata of the starch.

Starch modification rate=(turbidity after storage=turbidity before storage)/(turbidity after storage)×100(%)

The starch modification rates of the cellooligosaccharide powders of Examples 1 to 3 were 5%, 17%, and 9%, respectively, and an effect of preventing starch modification was observed as compared with a solution with no added cellooligosaccharide, which had a starch modification rate of 31%.

Example 8

The cellooligosaccharide powders 2 obtained in Examples 1 to 3 were dissolved in commercially available egg white at 5% by mass to prepare solutions of cellooligosaccharide in egg white. These solutions of cellooligosaccharide in egg white were stored at −20° C. for 5 days, and the protein modification rates were obtained by measuring turbidity (wavelength 660 nm) before and after storage.

Protein modification rate=(turbidity after storage−turbidity before storage/(turbidity after storage)× 100(%)

The protein modification rates of the cellooligosaccharide powders of Examples 1 to 3 were 3%, 9%, and 7%, respectively, and an effect of preventing protein modification was observed as compared with a solution with no added cellooligosaccharide, which had a protein modification rate of 62%.

Example 9

A food composition was prepared by the following method using the cellooligosaccharide powder obtained in Example 1.

First, 675.6 g of pharmacopoeial corn starch (average grain size 9 μm) and 15 g of talc (manufactured by Wako Pure Chemical Industries, Ltd.) were placed in a polyethylene bag and shaken with a hand for 3 minutes, then 195 g of the cellooligosaccharide powder of Example 1 was weighed and add to the mixed powder (total amount 900 g), and the mixture was placed in a 5-L V-shaped blender (manufactured by Dalton Co., Ltd.) and mixed for 30 minutes. 0.5 g each of the powder was collected from 10 random powder layers, and the cellooligosaccharide concentrations in the powder were measured. The coefficient of variation of the cellooligosaccharide concentration was 0.9% at this time. When this mixed powder was sifted through a sieve having a mesh size of 150 μm, no agglutinate was observed on the sieve.

The coefficient of variation referred to here is obtained by the following expression from the mean value and the standard deviation of the cellooligosaccharide concentrations in 10 powder samples in the above-mentioned analysis of the cellooligosaccharide concentrations.

Coefficient of variation(%)=standard deviation/mean concentration×100

Preparation Example 2

The *Trichoderma reesei* GL-1 strain international Patent Organism Depositary, National Institute of Advanced Industrial Science and Technology, Accession No. FERM ABP-10323) was inoculated in a nutrient agar medium and cultured at 37° C. for 7 days, and one loopful of spores were scooped from the medium surface, inoculated in a medium obtained by suspending and dissolving all of 1 g of polypeptone, 0.5 g of yeast extract, 2 g of monopotassium phosphate, 1.5 g of ammonium sulfate, 0.3 g of magnesium sulfate, 0.3 g of calcium chloride, 1 mL of trace elements (obtained by dissolving all of 6 mg of boric acid, 26 mg of ammonium molybdate tetrahydrate, 100 mg of iron(III) chloride hexahydrate, 40 mg of copper sulfate pentahydrate, 8 mg of manganese sulfate tetrahydrate, and 200 mg of zinc sulfate heptahydrate in 100 mL of purified water), 1 mL of adekanol, and 10 g of crystalline cellulose (manufactured by Asahi Kasei Chemicals Corporation, trade name PH-101, in 1 L of purified water, and aerobically cultured with stirring at 28° C. for 5 days. During the culture, the medium was adjusted to pH 2.8 to 4.7 using aqueous sodium hydroxide. After culture, the solution was centrifuged, the supernatant was collected and subjected to sterile filtration using a microfiltration membrane having a mesh size of 0.46 μm, and the filtrate was concentrated to 10% of the original volume using an ultrafiltration membrane having a molecular weight cutoff of 13,000 (manufactured by Asahi Kasei Chemicals Corporation, trade name Microza Pencil-Type Module ACP-0013) to obtain a crude enzyme.

Subsequently, a commercially available dissolving pulp derived from a coniferous tree was hydrolyzed under conditions of hydrolysis with aqueous hydrochloric acid containing hydrochloric acid at a concentration of 0.4% at 120° C. for 1 hour, and acid-insoluble residues were washed and filtered to obtain a wee cake. This wet cake was converted to a water dispersion containing cellulose at a concentration of 10% and subjected to compression/grinding treatment using a super performance dispersing/wet-pulverizing machine (manufactured by Ashizawa Co., trade name Pearl Mill RL using φ1 mm zirconium beads, filling rate 80%) to obtain a cellulose microparticle dispersion (average degree of polymerization 220, diethyl ether soluble matter content 0.7%, average particle size 0.7 μm, colloidal component content 51.5%).

This ground cellulose and the crude enzyme were suspended and dissolved in a 50 mM acetic acid-sodium acetate buffer (pH 4.5° to make 1000 mL as a total volume so that the ground cellulose content should be 2% by mass, and the crude enzyme should have a protein concentration of 0.25%, and poured in a glass flask. This glass flask was placed in a water bath at 55° C., and the content therein was reacted for 4 hours with stirring. After completion of the reaction, 300 μL of the reaction mixture was dispensed in the state of suspension, the enzyme and undegraded cellulose were removed using an ultrafiltration module (molecular weight cutoff 10,000), and then the saccharide concentrations were analyzed by high performance liquid chromatography. The saccharide concentrations of the reaction mixture were 0.2% by mass of cellotriose, cellotetraose, cellopentaose, and cellohexaose, 1.5% by mass of cellobiose, and 0.3% by mass of glucose.

This reaction mixture was filtered through an ultrafiltration membrane having a fraction molecular weight cutoff of 13,000 (manufactured by Asahi Kasei Chemicals Corporation, trade name Microza Pencil-Type Module ACP-0013), and the obtained filtrate was deionized using a cation/anion exchange resin and distilled at 70° C. under reduced pressure to obtain an aqueous solution having a 20 times higher saccharide concentration.

Preparation Example 3

100 mL of the aqueous cellooligosaccharide solution obtained in Preparation Example 2 was poured into a 200-mL glass flask and cooled from 70° C. to 5° C. at a rate of 10° C. per hour with stirring. A cellooligosaccharide crystallized in the aqueous solution at 25° C. was filtered under reduced pressure, dried with a circulation drier at 40° C., pulverized with a mortar, and sifted through a sieve having a mesh size of 150 μm, and the sifted powder was sifted through a sieve having a mesh size of 45 μm to remove fine powders to obtain a cellooligosaccharide powder CE-1A. The saccharide composition in the obtained cellooligosaccharide powder is shown in Table 1.

Preparation Example 4

An aqueous cellooligosaccharide solution was prepared in the same manner as in Preparation Example 1 except that the bacterial strain in Preparation Example 2 was chanced to *Cellovibrio gilvus*, pH during culture was changed to 4 to 10, and the buffer or enzymatic reaction was changed to a phosphate buffer (pH 6.5).

The obtained aqueous cellooligosaccharide solution was allowed to pass through a column filled with active carbon to remove cellobiose-rich fractions, and a cellooligosaccharide powder CE-2A was obtained by the same procedure as in Preparation Example 2. The saccharide composition in the obtained cellooligosaccharide powder is shown in Table 1.

Preparation Example 5

Ethanol having a 2.5 times weight was added to an aqueous cellooligosaccharide solution at room temperature in the cellooligosaccharide production method of Preparation Example 3, and the mixture was crystallized by cooling in the same manner as in Preparation Example 1 to obtain a cellooligosaccharide powder CE-3A.

Preparation Example 6

The aqueous cellooligosaccharide solution obtained in Preparation Example 4 was spray-dried as it was (using a spray drier manufactured by Tokyo Rikakikai Co., Ltd., outlet temperature 72° C.) to obtain a cellooligosaccharide powder CE-4A.

were lower than 30%, and it was confirmed that these cellooligosaccharides had an insulin non-elevating-property.

Improvement of Lifestyle-Related Diseases in Mice Spontaneously Developing Type 2 Diabetes Examples 10 to 12

As laboratory animals, 5-week-old male KK-$A^y$ mice (produced by CLEA Japan, Inc., Ta/Jc1) were used. Mice were housed in individual stainless cages and bred in a breeding room maintained at room temperature of 23±5° C. and a humidity of 40 to 70% with a light-dark cycle of 12 hours (light on 7.00 a.m. to 7.00 p.m.) and 12 times/hour ventilation (fresh air subjected to sterile filtration by a filter).

First, animals were preliminarily bred for 5 days. A powder feed (manufactured by CRF-1Oriental Yeast Co., Ltd.) was placed in a feeder and provided ad libitum during the preliminary breeding. Furthermore, tap water was used as drinking water and given ad libitum during the breeding period.

After the preliminary breeding, animals were divided by randomization using a computer into groups each consisting of 10 animals so that blood sugar levels and body weight should virtually match before grouping. After the grouping, the powder feed was replaced with a standard feed manufactured by Oriental Yeast Co., Ltd., AIN-93G, and the animals were similarly bred. Effects of addition of a cellooligosaccharide were compared by fixing the amount of sucrose in the above-described standard feed and replacing 2.5 or 5% by mass of components other than sucrose with a cellooligosaccharide de powder of CE-1A to -3A shown in Table 1. The results after breeding for 30 and 60 days are shown in Table 2.

Comparative Examples 2 and 3

Animals were bred under the same conditions as in Examples 10 to 12 except that E-3A and CE-4A were used as cellooligosaccharides. The results are shown in Table 2.

Comparative Example 4

As a control, animals were bred using a standard feed alone without adding any cellooligosaccharide. The results are

TABLE 1

| SACCHARIDE COMPOSITION | | PREPARATION EXAMPLE 3 CE-1A | PREPARATION EXAMPLE 4 CE-2A | PREPARATION EXAMPLE 5 CE-3A | PREPARATION EXAMPLE 6 CE-4A |
|---|---|---|---|---|---|
| CONTENT OF G1 | % BY MASS | 1.8 | 0.8 | 9.1 | 21.2 |
| CONTENT OF CE2 | % BY MASS | 96.5 | 71.3 | 81.2 | 68.4 |
| CONTENT OF CE3, CE4, CE5, AND CE6 | % BY MASS | 1.7 | 27.9 | 9.7 | 10.4 |

* G1, GLUCOSE; CE2, CELLOBIOSE; CE3, CELLOTRIOSE; CE4, CELLOTETRAOSE; CE5, CELLOPENTAOSE; CE6, CELLOHEXAOSE

Identification Test for Insulin Non-Elevating-Property 7-week-old SD rats were preliminarily bred by feeding AIN-93G (manufactured by Oriental Yeast Co., Ltd.) ad libitum for 1 week, fasted for 16 hours, and given 1500 mg/kg of an aqueous cellooligosaccharide solution in Table 1 using a sonde. Before dosing, after dosing, and at 30 minutes after dosing, blood was collected from the extracranial vein under no anesthesia, and the insulin concentration (ng/mL: using Lbis Insulin Kit manufactured by Shibayagi Co., Ltd.) was measured. The insulin level increasing rates by CE-1A to -3A shown in Table 2. There was no significant difference between the Examples and the Comparative Examples in food intake and body weight throughout the test.

Feed Composition

Casein 20.0% by mass
L-cysteine 0.3% by mass
Corn starch 39.7% by mass
α-corn starch 13.2% by mass
Sucrose 10.0% by mass
Soybean oil 7.0% by mass Cellulose powder 5.0% by mass
AIN-93 mineral mixture 3.5% by mass
AIN-93 vitamin mixture 1.0% by mass
Choline bitartrate 0.25% by mass
Tertiary butylhydroquinone 0.0014% by mass
In the cellooligosaccharide-added group, the above-described sucrose amount, 10.0% by masse was fixed and 5.0% by mass of the other components relative to the total feed amount was replaced by cellooligosaccharide.

Test Items and Methods (Body Weight Measurement)
Body weight of each mouse was measured at 30 and 60 days after grouping.
(Food Intake Measurement)
At 8, 15, 30, and 60 days after grouping, food intake of the day was measured for each mouse.
(Blood Collection and Blood Analysis)
At 15, 30, and 60 days after grouping, about 100 μL of blood was collected from the caudal vein using a heparin-treated capillary. The obtained blood was centrifuged by a centrifugal machine (manufactured by Hitachi Koki Co., Ltd., trade name CF8DL) at 4° C. and 1972 G for 15 minutes, and plasma was measured for the following items.
Blood adiponectin concentration (using Adiponectin ELISA Kit manufactured by Otsuka Pharm. Co., Ltd. was used)
Plasma neutral fat using Triglyceride E-test Wako manufactured by Wako Pure Chemical Industries, Ltd.)
Plasma total cholesterol (using Cholesterol E-test Wako manufactured by Wako Pure Chemical Industries, Ltd.)
(Measurement of Isolated Organs)
At 60 days after dosing, the liver and the epididymis fat were removed under intraperitoneal administered anesthesia with 50 mg/kg of ketamine hydrochloride and 2 ma/kg of xylazine, measured for weight, and frozen with liquid nitrogen. Lipids were extracted from the above-mentioned liver with hexane, and total cholesterol concentrations and neutral fat concentrations in the liver were measured as lipids in the liver.

TABLE 2

| | | EXAMPLE 10 CE-1A 2.5% REPLACED | | | EXAMPLE 11 CE-1A 5.0% REPLACED | | | EXAMPLE 12 CE-2A 5.0% REPLACED | | |
|---|---|---|---|---|---|---|---|---|---|---|
| MEASUREMENT DAY (DAYS AFTER GROUPING) | | 0 | 30 | 60 | 0 | 30 | 60 | 0 | 30 | 60 |
| BLOOD ADIPONECTIN CONCENTRATION (μg/ml) | | | 12.9 | 13.0 | | 11.7 | 11.1 | | 12.1 | 10.5 |
| DECREASING RATE OF BLOOD ADIPONECTIN CONCENTRATION (%) | | | 16.8 | 5.1 | | 24.5 | 19.0 | | 21.9 | 23.4 |
| PLASMA | TRIGLYCERIDE CONCENTRATION (mg/dL) | 302.8 | 299.4** | 275.3** | 304.7 | 259.4** | 214.0** | 306.7 | 272.0** | 258.7** |
| | TOTAL CHOLESTEROL CONCENTRATION (mg/dL) | 159.6 | 152.9 | 147.3** | 158.2 | 156.1** | 149.5** | 160.2 | 155.1 | 151.3* |
| LIVER | TRIGLYCERIDE CONCENTRATION (mg/g-wet liver) | — | 40.02 | 46.03** | — | 32.1* | 43.75** | — | 26.64** | 42.38** |
| | DECREASING RATE OF TRIGLYCERIDE CONCENTRATION (%) | | | 18.39 | | | 22.44 | | | 24.86 |
| | TOTAL CHOLESTEROL CONCENTRATION (mg/g-wet liver) | — | 6.01 | 6.88* | — | 7.10 | 6.50** | — | 5.29* | 6.06** |
| | DECREASING RATE OF TRIGLYCERIDE CONCENTRATION (%) | | | 5.75 | | | 11.02 | | | 17.00 |
| INTRAPERIONEAL | EPIDIDYMIS LIPID WEIGHT (g/animal) | — | 0.71 | 0.73** | — | 0.62* | 0.69** | — | 0.52** | 0.52** |

| | | COMPARATIVE EXAMPLE 2 CE-3A 2.5% REPLACED | | | COMPARATIVE EXAMPLE 3 CE-4A 5.0% REPLACED | | | COMPARATIVE EXAMPLE 4 NO CELLOOLIGOSACCHARIDE ADDED (CONTROL) | | |
|---|---|---|---|---|---|---|---|---|---|---|
| MEASUREMENT DAY (DAYS AFTER GROUPING) | | 0 | 30 | 60 | 0 | 30 | 60 | 0 | 30 | 60 |
| BLOOD ADIPONECTIN CONCENTRATION (μg/ml) | | | 10.1 | 9.5 | | 9.1 | 8.6 | | 15.5 | 13.7 |
| DECREASING RATE OF BLOOD ADIPONECTIN CONCENTRATION (%) | | | 34.8 | 30.7 | | 41.3 | 37.2 | | — | — |
| PLASMA | TRIGLYCERIDE CONCENTRATION (mg/dL) | 299.6 | 300.4* | 345.9* | 300.4 | 345.5 | 376.4 | 300.5 | 353.3 | 406.8 |
| | TOTAL CHOLESTEROL CONCENTRATION (mg/dL) | 158.1 | 155.2 | 148.5** | 158.0 | 150.2 | 151.2 | 157.2 | 150.4 | 157.2 |
| LIVER | TRIGLYCERIDE CONCENTRATION (mg/g-wet liver) | — | 46.00 | 53.42 | — | 45.30 | 56.50 | — | 39.70 | 56.40 |
| | DECREASING RATE OF TRIGLYCERIDE CONCENTRATION (%) | | | 5.28 | | | (0.18) | | | — |
| | TOTAL CHOLESTEROL CONCENTRATION (mg/g-wet liver) | — | 7.10 | 7.40 | — | 7.21 | 7.28 | — | 6.30 | 7.30 |

TABLE 2-continued

| | | | | | | | | | | |
|---|---|---|---|---|---|---|---|---|---|---|
| | DECREASING RATE OF TRIGLYCERIDE CONCENTRATION (%) | | | (1.37) | | | 0.27 | | | — |
| INTRAPERIONEAL | EPIDIDYMIS LIPID WEIGHT (g/animal) | | 0.77 | 0.72* | — | 0.71 | 0.70* | | 0.72 | 0.89 |

Note:
THE SYMBOL "*" IN THE TABLE INDICATES A RESULT OF STATISTICAL TESTING BY STUDENT'S T TEST BETWEEN EACH CELLOOLIGOSACCHARIDE ADDED GROUP AND CONTROL DURING THE SAME BREEDING PERIOD.
*SIGNIFICANT DIFFERENCE WAS DETERMINED AT SIGNIFICANCE LEVEL OF 0.10.
**SIGNIFICANT DIFFERENCE WAS DETERMINED AT SIGNIFICANCE LEVEL OF 0.05.

As shown in the results in Table 2, the decreasing rate of blood adiponectin was suppressed to 30% or lower during the same breeding period in all the Examples, and the decreasing rate of the triglyceride concentration in the liver was also 15% or higher. On the other hand, neither the decreasing rate of blood adiponectin or the decreasing rate of the neutral fat concentration in the liver was in the range of the present invention in Comparative Examples 2 and 3.

Furthermore, the cellooligosaccharide-added groups in Examples 10 to 12 significantly decreased plasma and intraperitoneal lipids as compared with Comparative Example 4. Comparison between Examples 10 and 11 showed that the increase in the cellooligosaccharide content in the feed shortened the time to exhibition of effect and decreased the absolute value in long-term treatment. Comparison between Examples 11 and 12 showed that a high content of cellotriose, cellotetraose, cellop, cellohexaose delayed the exhibition of hematological effects but promoted the decrease in liver lipids.

Furthermore, comparison between Comparative Example 2 and Examples 10 to 12, an effect of decreasing epididymis lipid was exhibited in spite of the high glucose content in the feed, but exhibition of effects on blood lipids was delayed, and there was no significant difference in liver lipids.

Furthermore, since the cellobiose content is less than 70% by mass, which is out of the range of the present invention, in Comparative Example 3, effects on epididymis lipid and blood lipid levels were lower than in Examples and Comparative Example 2.

Improvement of Lifestyle-Related Diseases in Healthy Rats

Examples 13 and 14

As laboratory animals, 5-week-old male SD rats (produced by Clea Japan, Inca) were used. Rats were housed in individual stainless cages and bred in a breeding room maintained at room temperature of 23±5° C. and a humidity 40 to 70% with a light-dark cycle of 12 hours light on 7.50 a.m. to 7.00 p.m.) and 12 times/hour ventilation (fresh air subjected to sterile filtration by a filter).

First, animals were preliminarily bred for 5 days. A powder feed (manufactured by CRF-1Oriental Yeast Co., Ltd., was placed in a feeder and provided ad libitum during the preliminary breeding. Furthermore, tap water was used as drinking water and given ad libitum during the breeding period.

After the preliminary breeding, animals were divided by randomization using a computer into groups each consisting of 10 animals so that blood sugar levels and body weight should virtually match before grouping. After grouping, animals were similarly bred without changing the powder feed.

The above-described CE-1A was dissolved or suspended in purified water, and 160 or 1000 mg/kg of cellooligosaccharide was given once daily for 13 weeks using a sonde. After dosing, rats were anesthetized by intraperitoneally dosing 30 mg/kg of pentobarbital sodium, then 2.0 to 2.5 mL of blood was collected from the postcava abdomen, and 0.9 mL of blood was dispensed into a test tube containing 0.1 mL of 3.8% w/v sodium citrate and centrifuged at 1870 G for 15 minutes. Using the centrifuged plasma, blood adiponectin concentrations and plasma and liver triglyceride concentrations were measured in the same manner as described above.

Comparative Example 5

Animals were bred by the same procedures as in Examples 13 and 14 except that no cellooligosaccharide was given, and blood adiponectin concentrations in plasma and neutral fat concentrations in the liver were measured.

There was no significant difference between Examples and Comparative Example in food intake and body weight throughout the test.

TABLE 3

| | | EXAMPLE 13 CE-1A | EXAMPLE 14 CE-1A | COMPARATIVE EXAMPLE 5 NO CELLOOLIGOSACCHARIDE GIVEN |
|---|---|---|---|---|
| DOSE | mg/kg | 160 | 1000 | 0 |
| BLOOD ADIPONECTIN CONCENTRATION | μg/ml | 0.838 | 0.729 | 0.976 |
| DECREASING RATE OF BLOOD ADIPONECTIN CONCENTRATION | % | 14.139 | 25.307 | — |
| PLASMA NEUTRAL FAT CONCENTRATION | mg/dL | 5014 | 49 ± 14*** | 68 ± 68 |
| LIVER WEIGHT | g/animal | 14.11 ± 1.53 | 13.64 ± 1.50* | 14.32 ± 1.69 |
| NEUTRAL FAT CONCENTRATION IN LIVER | mg/g-wet liver | 67.01 ± 9.20 | 55.59 ± 9.7** | 79.61 ± 7.56 |

TABLE 3-continued

|  |  | EXAMPLE 13 CE-1A | EXAMPLE 14 CE-1A | COMPARATIVE EXAMPLE 5 NO CELLOOLIGOSACCHARIDE GIVEN |
|---|---|---|---|---|
| DECREASING RATE OF NEUTRAL FAT CONCENTRATION IN LIVER | % | 15.8 | 30.2 | — |

Note:
THE SYMBOL "*" IN THE TABLE INDICATES A RESULT OF STATISTICAL TESTING BY STUDENT'S T TEST BETWEEN EITHER CELLOLIGOSACCHARIDE-ADDED GROUP AND CONTROL DURING THE SAME BREEDING PERIOD.
*SIGNIFICANT DIFFERENCE WAS DETERMINED AT SIGNIFICANCE LEVEL OF 0.10.
**SIGNIFICANT DIFFERENCE WAS DETERMINED AT SIGNIFICANCE LEVEL OF 0.05.
***SIGNIFICANT DIFFERENCE WAS DETERMINED AT SIGNIFICANCE LEVEL OF 0.1.

As shown in Table 3, the decreasing rate of adiponectin concentration was 30% or lower, and the decreasing rate of the neutral fat concentration in the liver was 15% or higher, which were within the range of the present invention, in the Examples as compared with the Comparative Example. Furthermore, blood and liver lipid concentrations decreased dose-dependently in the cellooligosaccharide-added groups, and liver weight also tended to decrease in the high dose group. This test demonstrated that blood and liver lipid concentrations could also be decreased in healthy rats by intake of a cellooligosaccharide without changing the amount of food intake.

Activation of Enteric Bacteria Flora

Preparation Example 7

*Trichoderma reesei* was inoculated in a nutrient agar medium and cultured 37° C. for 7 days, and one loopful of spores were scooped from the medium surface, inoculated in a medium obtained by suspending and dissolving all of 1 g of polypeptone, 0.5 g of yeast extract, 2 g of monopotassium phosphate, 1.5 g of ammonium sulfate, 0.3 g of magnesium sulfate, 0.3 g of calcium chloride, 1 mL of trace elements (obtained by dissolving all of 6 mg of boric acid, 26 mg of ammonium molybdate tetrahydrate, 100 mg of iron(III) chloride hexahydrate, 40 mg of copper sulfate pentahydrate, 8 mg of manganese sulfate tetrahydrate, and 200 mg of zinc sulfate heptahydrate in 100 mL of purified water), 1 mL of adekanol, and 10 g of crystalline cellulose (manufactured by Asahi Kasei Chemicals Corporation, trade name PH-101 in 1 L of purified water, and aerobically cultured with stirring at 28° C. for 5 days. During the culture, the medium was adjusted to pH 2.8 to 4.7 using aqueous sodium hydroxide. After culture, the solution was centrifuged, the supernatant was collected and subjected to sterile filtration using a microfiltration membrane having a mesh size of 0.46 μm, and the filtrate was concentrated to 10% of the original volume using an ultrafiltration membrane having a molecular weight cutoff of 13,000 (manufactured by Asahi Kasei Chemicals Corporation, trade name Microza Pencil-Type Module ACP-0013) to obtain a crude enzyme.

Subsequently, a commercially available dissolving pulp derived from coniferous tree was hydrolyzed under conditions of hydrolysis with aqueous hydrochloric acid containing hydrochloric acid at a concentration of 0.4% at 120° C. for 1 hour, and acid-insoluble residues were washed and filtered to obtain a wet cake. This wet cake was converted to a water dispersion containing cellulose at a concentration of 10% and subjected to compression/grinding treatment using a super performance dispersing/wet-pulverizing machine (manufactured by Ashizawa Co., trade name Pearl Mild RL using a φ1 mm zirconium beads, filling rate 80%) to obtain a cellulose microparticle dispersion average degree of polymerization 220, diethyl ether-soluble matter content 0.7%, average particle size 0.7 μm, colloidal component content 51.5%).

This ground cellulose and the crude enzyme were suspended and dissolved in a 50 mm acetic acid-sodium acetate buffer (pH 4.5) to make 1000 mL as a total volume so that the ground cellulose content should be 2% by mass, and the crude enzyme should have a protein concentration of 0.25%, and poured in a glass flask. This glass flask was placed in a water bath at 55° C., and the content therein was reacted for 4 hours with stirring. After completion of the reaction, 300 μL of the reaction mixture was dispensed in the state of suspension, the enzyme and undegraded cellulose were removed using an ultrafiltration module (molecular weight cutoff 10,000), and then the saccharide concentrations were analyzed by high performance liquid chromatography. The saccharide concentrations of the reaction mixture were 0.2% by mass of cellotriose, cellotetraose, cellopentaose, and cellohexaose, 1.5% by mass of cellobiose, and 0.3% by mass of glucose.

This reaction mixture was filtered through an ultrafiltration membrane having a molecular weight cutoff of 13,000 manufactured by Asahi Kasei Chemicals Corporation, trade name Microza Pencil-Type Module ACP-0013), and the obtained filtrate was deionized using a cation/anion exchange resin and distilled at 70° C. under reduced pressure to obtain an aqueous solution having a 20 tires higher saccharide concentration.

Preparation Example 8

100 mL of the aqueous cellooligosaccharide solution obtained in Preparation Example 7 was poured into a 200-mL glass flask and cooled from 70° C. to 5° C. at a rate of 10° C. per hour with stirring. A cellooligosaccharide crystallized in the aqueous solution at 25° C. was filtered under reduced pressure, dried with a circulation drier at 40° C., pulverized with a mortar, and sifted through a sieve having a mesh size of 150 μm, and the sifted powder was sifted through a sieve having a mesh size of 45 μm to remove fine powders to obtain a cellooligosaccharide powder CE-1B. The saccharide composition of the obtained cellooligosaccharide powder is shown in Table 4.

Preparation Example 9

100 mL of the aqueous cellooligosaccharide solution obtained in Preparation Example 7 was poured into a 200-mL glass flask and cooled from 700° to 5° C. at a rate of 10° C. per hour with stirring, and ethanol was added at a ratio of 70% by volume to water at a rate of 10 g per minute to crystallize the mixture. A cellooligosaccharide crystallized in the aqueous solution was filtered under reduced pressure, dried, pulverized, and sifted in the same manner as in Example 8 to obtain a cellooligosaccharide powder CE-2B. The saccharide composition of the obtained cellooligosaccharide powder is shown in Table 4.

Preparation Example 10

A aqueous cellooligosaccharide solution was prepared in the same manner as in Preparation Example 1 except that the bacterial strain in Preparation Example 7 was changed to *Cellovibrio gilvus*, pH during culture was changed to 4 to 10, and the buffer for enzymatic reaction was changed to a phosphate buffer (pH 6.5).

The obtained aqueous cellooligosaccharide solution was allowed to pass through a column filled with active carbon to remove cellobiose-rich fractions, and a cellooligosaccharide powder CE-3B was obtained by the same procedure as in Preparation Example 9. The saccharide composition of the obtained cellooligosaccharide powder is shown in Table 4.

Preparation Example 11

The aqueous cellooligosaccharide solution of Preparation Example 7 was once crystallized by the method of Preparation Example 2, an aqueous solution of the obtained cellooligosaccharide was prepared, and fractions having a molecular weight of cellotriose or higher were cut off by the active carbon treatment described in Preparation Example 4. The aqueous cellooligosaccharide solution was powderized by the same procedures as in Preparation Example 9 to obtain a cellooligosaccharide powder CE-4B.

Preparation Example 12

Glucose-rich fractions were collected from the column fractions treated with active carbon in Preparation Example 10, dried in a ventilated oven at 60° C. for 16 hours, and powderized by the same procedures as in Preparation Example 8 to obtain a cellooligosaccharide powder CE-5B. The saccharide composition of the obtained cellooligosaccharide powder is shown in Table 4.

Preparation Example 13

Fractions rich with cellotriose, cellotetraose, cellopentaose, and cellohexaose were collected from the column fractions treated with active carbon in Preparation Example 10, dried in a ventilated oven at 60° C. for 16 hours, and powderized by the same procedures as in Preparation Example 9 to obtain a cellooligosaccharide powder CE-6B. The saccharide composition of the obtained cellooligosaccharide powder is shown in Table 4.

Example 15

Using CE-1B to -3B obtained in Preparation Examples 7 to 1, an assimilation test of each bacterial strain was performed by the following method.

1.5 mL of a sterilized medium (pH 7.2) was prepared by adding 1.0% by mass of the cellooligosaccharide of present invention to Peptone-Yeast-Fildes solution (manufactured by Nihon Pharmaceutical Co., Ltd., PYF) medium, and 0.03 mL of a test bacterial solution in which the following various bacterial strains were pre-cultured beforehand in a Fildes solution-added GAM bouillon medium (0.4% by volume of Fildes solution was added to GAM, bouillon [product name] manufactured by Nihon Pharmaceutical CO., Ltd.) was inoculated therein and anaerobically cultured at 37° C. for 96 hours, then pH was measured to determine an assimilation property. When the pH is decreased to lower than 6.0, it can be determined that the bacterial strain has assimilated a cellooligosaccharide. The lower pH means that propagation of the bacterial strain has proceeded. The results are shown in Table 5.

Comparative Example 6

The assimilation property was evaluated in the same manner as the method of the Example, except that the cellooligosaccharide was replaced with CE-4B to -6B.

Reference Example 1

Using gentiooligosaccharide (manufactured by Nihon Shokuhin Kako Co., Ltd. trade name Gentose 80P) and fructooligosaccharide (manufactured by Meiji Seika Kaisha, Ltd. trade name Meioligo P) instead of a cellooligosaccharide, the assimilation property was evaluated in the same manner as in the Example.

Bacterial Strains Used

1) *Bifidobacterium adlescentis*
2) *Bifidobacterium bifidum*
3) *Bifidobactenurium breve*
4) *Bifidobacterium infantis*
5) *Bifidobacterium longum*
6) *Lactobacillus acidophilus*
7) *Lactobacillus casei*
8) *Lactobacillus salibarius*
9) *Lactobacillus gasseri*
10) *Lactobacillus fermentum*
11) *Streptococcus pyogenes*
12) *Bacteroides destasonis*

TABLE 4

| SACCHARIDE COMPOSITION | | PREPARATION EXAMPLE 8 CE-1B | PREPARATION EXAMPLE 9 CE-2B | PREPARATION EXAMPLE 10 CE-3B | PREPARATION EXAMPLE 11 CE-4B | PREPARATION EXAMPLE 12 CE-5B | PREPARATION EXAMPLE 13 CE-6B |
|---|---|---|---|---|---|---|---|
| CONTENT OF G1 | % BY MASS | 0.9 | 1.8 | 0.8 | 1.6 | 26.2 | 0.2 |
| CONTENT OF CE2 | % BY MASS | 98.3 | 96.5 | 79.3 | 98.4 | 71.2 | 67.3 |
| CONTENT OF CE3, CE4, CE5 AND CE6 | % BY MASS | 0.8 | 1.7 | 19.9 | 0 | 2.6 | 32.5 |

* G1, GLUCOSE; CE2, CELLOBIOSE; CE3, CELLOTRIOSE; CE4, CELLOTETRAOSE; CE5, CELLOPENTAOSE; CE6, CELLOHEXAOSE

13) *Bacteroides fragilis*
14) *Bacteroides ovatus*
17) *Bacteroides thetaiotaomicron*
16) *Bacteroides vulfatus*
17) *Bacteroides uniformis*
18) *Bacteroides meraminogenicus*
19) *Fusobacterium vanium*
20) *Fusobacterium necrophorum*
21) *Maegamonas hypermegas*
22) *Mitsuokella muitiacidus*
23) *Eubacterium limosum*
24) *Eubacterium aerofacience*
25) *Eubacterium nitritogenes*
26) *Eubacterium lentum*
27) *Enterobacter aerogenes*
28) *Enterococcus faecauis*
29) *Clostridium butyricum*
30) *Clostridium clostridiiforme*
31) *Clostridium coccoides*
32) *Clostridium difficile*
33) *Clostridium perfringens*
34) *Clostridium paraputrificum*
35) *Clostridium ramosum*
36) *Clostridium innocuum*
37) *Clostridium sporogenes*
38) *Propionibacterium acnes*
39) *Peptostreptcoccus parvulus*
40) *Peptostreptcoccus asaccharolyticus*
41) *Peptostreptcoccus magnus*
42) *Peptostreptcoccus prevolli*
43) *Escherichia coli*
44) *Klebsielia pneumoniae*

Evaluation Criteria

−: pH≧6.0
±: pH 5.5-<6.0
+: pH 5.0-<5.5
++: pH 4.5-<5.0
+++: pH<4.5

TABLE 5

| | | EXAMPLE | | | COMPARATIVE EXAMPLE | | | REFERENCE EXAMPLE | |
|---|---|---|---|---|---|---|---|---|---|
| BACTERIAL STRAIN | | CE-1B | CE-2B | CE-3B | CE-4B | CE-5B | CE-6B | GO | FO |
| *Bifidobacterium* | adolescentis | +++ | +++ | +++ | +++ | +++ | +++ | +++ | +++ |
| | bifidum | − | − | − | ± | − | − | +++ | − |
| | breve | ++ | ++ | ++ | ++ | ++ | ++ | +++ | ++ |
| | infantis | − | − | − | ± | − | − | +++ | +++ |
| | longum | − | − | − | ± | − | − | +++ | ++ |
| *Lactobacillus* | acidophilus | +++ | +++ | +++ | +++ | +++ | +++ | +++ | +++ |
| | casei | +++ | +++ | +++ | +++ | +++ | +++ | +++ | − |
| | salibarius | − | − | − | ++ | − | − | − | ++ |
| | gasseri | +++ | +++ | +++ | +++ | +++ | +++ | +++ | +++ |
| | fermntum | − | − | − | ± | − | − | − | − |
| *Streptococcus* | pyogenes | ± | ± | ± | + | ± | ± | | − |
| *Staphylogcoccus* | aureus | − | − | − | ± | − | − | | + |
| *Bateroides* | distasonis | ± | ± | ± | ± | ± | ± | + | ± |
| | fragilis | − | − | ± | + | − | + | ++ | + |
| | ovatus | + | + | + | ++ | + | + | ++ | + |
| | thetaiotaomicron | ± | ± | + | + | ± | + | ++ | + |
| | vulgatus | − | − | − | − | − | − | + | + |
| | uniformis | + | + | + | + | + | + | + | + |
| *Fsobacterium* | varium | − | − | − | ± | − | − | | − |
| | necrophorum | − | − | − | − | − | − | | − |
| *Megamonas* | hypermegas | − | − | − | + | − | − | | ++ |
| *Mitsuokella* | multiacidus | +++ | +++ | +++ | +++ | +++ | +++ | | +++ |
| *Eubacterium* | limosum | − | − | − | + | − | − | ± | − |
| | aerofaciens | ± | ± | ± | ++ | + | ± | − | ± |
| | nitritogenes | + | ± | ± | + | + | ± | ± | ± |
| | lentum | − | − | − | − | − | − | − | − |
| *Enterobacter* | aerogenes | + | + | + | + | + | + | | − |
| *Enterococcus* | faecalis | +++ | +++ | +++ | +++ | +++ | +++ | | + |
| *Clostridium* | butyricum | ++ | ++ | ++ | ++ | ++ | ++ | ++ | ++ |
| | clostridiiforme | ± | ± | ± | ± | ± | ± | − | − |
| | difficile | − | − | − | ± | − | − | − | − |
| | perfringens | − | − | − | + | + | ± | ± | − |
| | paraputrificum | ++ | ++ | ++ | ++ | ++ | ++ | + | − |
| | ramosum | + | + | + | + | + | + | ++ | ± |
| | innocuum | + | + | + | + | + | + | ± | ± |
| | sporogenes | − | − | − | − | − | − | − | − |
| *Propionibacterium* | acnes | − | − | − | + | − | − | − | − |
| *Peptostreptcoccus* | parvulus | + | + | ++ | ++ | + | ++ | | + |
| | asaccharolyticus | − | − | − | − | − | − | | − |
| | magnus | − | − | − | − | − | − | | − |
| | prevolli | ± | ± | ± | − | ± | ± | | ± |
| *Escharichia* | coli | − | − | − | + | ++ | − | ± | − |
| *Klebsiella* | pneumoniae | + | + | + | + | + | + | | ± |

* "GO2 IN THE TABLE DENOTES GENTIOOLIGOSACCHARIDE, AND "FO" DENOTES FRUCTOOLIGOSACCHARIDE.

As shown in Table 5, bifidobacteria and lactic bacteria could be selectively activated, and propagation of *Bacteroides fragilis* and *Eubacterium aerofaciens* could be suppressed in addition of propagation of *Clostrtdium* perfringens and *Escherichia coli* by making the cellobiose content high, the glucose concentration low, and the content of cellotriose, cellotetraose, cellopentaose, and cellohexaose within a proper range.

Suppressing or Improving Agents for *Helicobacter pylori*

Preparation Example 14

*Trichoderma reesei* was inoculated in a nutrient agar medium and cultured 37° C. for 7 days, and one loopful of spores were scooped from the medium surface, inoculated in a medium obtained by suspending and dissolving all of 1 g of polypeptone, 0.5 g of yeast extract, 2 g of monopotassium phosphate, 1.5 g of ammonium sulfate, 0.3 g of magnesium sulfate, 0.3 g of calcium chloride, 1 mL of trace elements (obtained by dissolving all of 6 mg of boric acid, 26 mg of ammonium molybdate tetrahydrate, 100 mg of iron(III) chloride hexahydrate, 40 mg of copper sulfate pentahydrate, 8 mg of manganese sulfate tetrahydrate, and 200 mg of zinc sulfate heptahydrate in 100 mL of purified water), 1 mL adekanol, and 10 g of crystalline cellulose manufactured by Asahi Kasei Chemicals Corporation, trade name PH-101) in 1 L of purified water, and aerobically cultured with stirring at 28° C. for 5 days. During the culture, the medium was adjusted to pH 2.8 to 4.7 using aqueous sodium hydroxide. After culture, the solution was centrifuged, the supernatant was collected and subjected to sterile filtration using a microfiltration membrane having a mesh size of 0.46 μm, and the filtrate was concentrated to 10% of the original volume using an ultrafiltration membrane having a molecular weight cutoff of 13,000 (manufactured by Asahi Kasei Chemicals Corporation, trade name Microza Pencil-Type Module ACP-0013; to obtain a crude enzyme.

Subsequently, a commercially available dissolving pulp derived from a coniferous tree was hydrolyzed under conditions of hydrolysis with aqueous hydrochloric acid containing hydrochloric acid at a concentration of 0.4% at 120° C. for 1 hour, and acid-insoluble residues were washed and filtered to obtain a wet cake. This wet cake was converted to a water dispersion containing cellulose at a concentration of 10% and subjected to compression/grinding treatment using a super performance dispersing/wet-pulverizing machine manufactured by Ashizawa Co., trade name Pearl Mill RL using φ1 nm zirconium beads, filling rate 80%) to obtain a cellulose microparticle dispersion (average degree of polymerization 220, diethyl ether soluble matter content 0.7%, average particle size 0.7 μm, colloidal component content 51.5%).

This ground cellulose and the crude enzyme were suspended and dissolved in a 50 mM acetic acid-sodium acetate buffer (pH 4.5) to make 1000 mL as a total volume so that the ground cellulose content should be 2% by mass, and the crude enzyme should have a protein concentration of 0.25%, and poured in a glass flask. This glass flask was placed in a water bath at 55° C., and the content therein was reacted for 4 hours with stirring. After completion of the reaction, 300 μL of the reaction mixture was dispensed in the state of suspension, the enzyme and undegraded cellulose were removed using an ultrafiltration module (molecular weight cutoff 10,000, and then the saccharide concentrations were analyzed by high performance liquid chromatography. The saccharide concentrations of the reaction mixture were 0.2% by mass of cellotriose, cellotetraose, cellopentaose, and cellohexaose, 1.5% by mass of cellobiose, and 0.3% by mass of glucose.

This reaction mixture was filtered through an ultrafiltration membrane having a molecular weight cutoff of 13,000 (manufactured by Asahi Kasei Chemicals Corporation, trade name Microza Pencil-Type Module ACP-0013), and the obtained filtrate was deionized using a cation/anion exchange resin and distilled at 70° C. under reduced pressure to obtain an aqueous solution having a 20 times higher saccharide concentration.

Preparation Example 15

100 mL of the aqueous cellooligosaccharide solution obtained in Preparation Example 14 was poured into a 200-mL glass flask and cooled from 70° C. to 5° C. at a rate of 10° C. per minute with stirring, and ethanol was added at a ratio of 70% by volume to water at a rate of 10 g per minute to crystallize the mixture. A cellooligosaccharide crystallized in the aqueous solution was filtered under reduced pressure, dried, pulverized, and sifted to obtain a cellooligosaccharide powder CE-1C. The saccharide composition of the obtained cellooligosaccharide powder is shown in Table 6.

Preparation Example 16

An aqueous cellooligosaccharide solution was prepared in the same manner as in Preparation Example 14 except that the bacterial strain in Preparation Example 14 was changed to *Cellovibrio gilvus*, pH during culture was changed to 4 to 10, and the buffer for enzymatic reaction was changed to a phosphate buffer (pH 6.5).

The obtained aqueous cellooligosaccharide solution was allowed to pass through the column treated with active carbon to collect glucose-rich fractions/dried in a ventilated oven at 60° C. for 16 hours, and powder-zed by the same procedures as in Preparation Example 2 to obtain a cellooligosaccharide powder CE-2C. The saccharide composition of the obtained cellooligosaccharide powder is shown in Table 6.

TABLE 6

| SACCHARIDE COMPOSITION | | PREPARATION EXAMPLE 15 CE-1C | PREPARATION EXAMPLE 16 CE-2C |
|---|---|---|---|
| CONTENT OF G1 | % BY MASS | 1.8 | 26.2 |
| CONTENT OF CO2 | % BY MASS | 96.5 | 71.2 |
| CONTENT OF CO3, CO4, CO5 AND CO6 | % BY MASS | 1.7 | 2.6 |

* ABBREVIATIONS IN THE TABLE DENOTE THE FOLLOWING SACCHARIDES.
G1, GLUCOSE;
CO2, CELLOBIOSE;
CO3, CELLOTRIOSE;
CO4, CELLOTETRAOSE;
CO5, CELLOPENTAOSE;
CO6, CELLOHEXAOSE

Example 16

Using CE-1C as a cellooligosaccharide, the following test solutions were prepared to determine the suppressing rate of *Helicobacter pylori* propagation The results are shown in Table 7.

Test Solutions (0) 5% equine serum-added (1/10) *Brucella* broth to which no cellooligosaccharide was added
(1) 5% equine serum-added (1/10) *Brucella* broth in which 2% CE-1C was dissolved
(2) 5% equine serum-added (1/10) *Brucella* broth in which 5% CE-1C was dissolved
(3) 5% equine serum-added (1/10) *Brucella* broth in which 10% CE-1C was dissolved Culture Method The test bacterial strain (*Helicobacter pylori* ATCC43504) was microaerobically cultured in a sheep blood agar medium K (BBL) at 35° C. for 3 days and adjusted with sterilized physiological saline to obtain McFarland No. 2 (about $10^7$ to $10^8$ CFU/mL). This solution was 100-fold diluted with sterilize physiological saline to obtain a bacterial solution for addition. 1 mL of the bacterial solution for addition was added to 9 mL of each test solution, the bacterial cells were cultured at 35° C. under a microaerobic condition with stirring, and the solution was used as a sample solution. After 72 hours of culture, each test solution was collected, a series of 10-fold diluted solutions were prepared with sterilized physiological saline. 50 µL each of the stock solution and the series of diluted solutions were smeared with a Conradi's glass rod to a sheep blood agar medium K and cultured under a microaerobic condition at 35° C. for 4 to 5 days. After 0 hour, only test solutions were Quantified. The number of bacterial cells that grew after the culture were counted to obtain the viable cell count per mL. The propagation suppressing rate was obtained by the following expression.

Suppressing rate of propagation(%)=(viable cell count 2−viable cell count 1)/viable cell count 2×100

Example 17

By changing the cellooligosaccharide in Example 26 to CE-2C and adding the cellooligosaccharide to the test solution at 2%, the suppressing rate of *Helicobacter pylori* propagation was obtained in the same manner as in Example 16. The results are shown in Table 7.

Comparative Example 7

Using D-glucose (manufactured by Wako Pure Chemical Industries, Ltd.) instead of a cellooligosaccharide in Example 13 and adding the cellooligosaccharide to the test solution at 2%, the suppressing rate of *Helicobacter pylori* propagation was obtained in the same manner as in Example 13. The results are shown in Table 7.

more, Example 16 showed that as the amount of the added cellooligosaccharide was increased, the suppressing rate of *Helicobacter pylori* propagation improved, which resulted in an increase of the effect of suppressing the *Helicobacter pylori*.

Furthermore, the cellobiose content was higher, and the content of cellotriose, cellotetraose, cellopenta, and cellohexaose and the glucose content were lower in Example 16 as compared with Example 17. However, the viable cell count of *Helicobacter pylori* was less with the equal addition amount. That is, the suppression effect was increased with a cellobiose content in the cellooligosaccharide.

Furthermore, Comparative Example 7 showed that glucose had no effect of suppressing *Helicobacter pylori*

Example 18

Using CE-1C as a cellooligosaccharide with the addition amounts of 5% and 10%, the bacterial strain was cultured by the same procedures as in Example 16. The various culture time were scheduled over 48 to 96 hours, and the viable cell counts were compared with that in the solution containing no cellooligosaccharide. The results are shown in FIG. 1.

Agent for Improving Skin Barrier Function

Preparation Example 17

*Trichoderma reesei* was inoculated in a nutrient agar medium and cultured 37° C. for 7 days, and one loopful of spores were scooped from the medium surface, inoculated in a medium obtained by suspending and dissolving all of 1 g of polypeptone, 0.5 g of yeast extract, 2 g of monopotassium phosphate, 1.5 g of ammonium sulfate, 0.3 g of magnesium sulfate, 0.3 g of calcium chloride, 1 mL of trace elements (obtained by dissolving all of 6 mg of boric acid, 26 mg of ammonium molybdate tetrahydrate, 100 mg of Iron(III) chloride hexahydrate, 40 mg of copper sulfate pentahydrate, 8 mg of manganese sulfate tetrahydrate, and 200 mg of zinc sulfate heptahydrate in 100 mL of purified water), 1 mL of adekanol, and 10 g of crystalline cellulose (Asahi Kasei Chemicals Corporation, trade name PH-101) in 1 L of purified water, and aerobically cultured with stirring at 28° C. for 5 days. During the culture, the medium was adjusted to pH 2.8 to 4.7 using aqueous sodium hydroxide. After culture, the solution was centrifuged, the supernatant was collected and subjected to sterile filtration using a microfiltration membrane having a mesh size of 0.46 µm, and the filtrate was concentrated to 10% of the original volume using an ultrafiltration membrane having a molecular weight cutoff of 13,000 (manufactured by Asahi Kasei Chemicals Corporation, trade name Microza Pencil-Type Module ACP-001) to obtain a crude enzyme.

TABLE 7

| | CELLOOLIGOSACCHARIDE/ ADDITION AMOUNT | TEST SOLUTION | VIABLE CELL COUNT | SUPPRESSING RATE OF PROPAGATION % |
|---|---|---|---|---|
| EXAMPLE 16 | NO CELLOOLIGOSACCHARIDE ADDED | (0) | $122 \times 10^5$ | — |
| | CE-1C/2% | (1) | $60 \times 10^5$ | 51 |
| | CE-1C/5% | (2) | $28 \times 10^5$ | 77 |
| | CE-1C/10% | (3) | 0 | 100 |
| EXAMPLE 17 | CE-2C/2% | (4) | $72 \times 10^5$ | 41 |
| COMPARATIVE EXAMPLE 7 | GLUCOSE/2% | (5) | $122 \times 10^5$ | 0 |

Examples 16 and 17 showed that the cellooligosaccharides had the effect of suppressing *Helicobacter pylori*. Further- Subsequently, a commercially available dissolving pulp derived from a coniferous tree was hydrolyzed under conditions of hydrolysis with aqueous hydrochloric acid containing hydrochloric acid at a concentration of 0.4% at 120° C. for 1 hour, and acid-insoluble residues were washed and filtered to obtain a wet cake. This wet cake was converted to a water dispersion containing cellulose at a concentration of 10% and subjected to compression/grinding treatment using a super performance dispersing/wet-pulverizing machine (manufactured by Ashizawa Co., trade name Pearl Mill RL using φ1 mm zirconium beads, filling rate 80%) to obtain a cellulose microparticle dispersion average degree of polymerization 220, diethyl ether soluble matter content 0.7%, average particle size 0.7 μm, colloidal component content 51.5%).

This ground cellulose and the crude enzyme were suspended and dissolved in a 50 mM acetic acid-sodium acetate buffer (pH 4.5) to make 1000 mL as a total volume so that the ground cellulose content should be 2% by mass, and the crude enzyme should have a protein concentration of 0.25%, and poured in a glass flask. This glass flask was placed in a water bath at 55° C., and the content therein was reacted for 4 hours with stirring. After completion of the reaction, 300 μL of the reaction mixture was dispensed in the state of suspension, the enzyme and undegraded cellulose were removed using an ultrafiltration module (molecular weight cutoff 10,000), and then the saccharine concentrations were analyzed by high performance liquid chromatography. The saccharide concentrations of the reaction mixture were 0.2% by mass of cellotriose, cellotetraose, cellopentaose, and cellohexaose, 1.5% by mass of cellobiose, and 0.3% by mass of glucose.

This reaction mixture was filtered through an ultrafiltration membrane having a molecular weight cutoff of 13,000 (manufactured by Asahi Kasei Chemicals Corporation, trade name Microza Pencil-Type Module ACP-0013), and the obtained filtrate was deionized using a cation/anion exchange resin and distilled at 70° C. under reduced pressure to obtain an aqueous solution having a 20 times higher saccharide concentration.

Preparation Example 18

100 mL of the aqueous cellooligosaccharide solution obtained in Preparation Example 17 was poured into a 200-mL glass flask and cooled from 70° C. to 5° C. at a rate of 10° C. per hour with stirring, and ethanol was added at a ratio of 60% by volume to water at a rate of 10 g per minute to crystallize the mixture. A cellooligosaccharide crystallized in the aqueous solution was filtered under reduced pressure, dried, pulverized, and sifted in the same manner as in Example 2 to obtain a cellooligosaccharide powder CE-1D. In the saccharide composition of CE-1D, the cellobiose content was 94.9% by mass, the content of cellotriose, cellotetraose, cellopentaose, and cellohexaose combined was 2.6% by mass, and the glucose content was 2.5% by mass.

Preparation Example 19

CE-1D obtained by Preparation Example 18 was used to obtain an aqueous solution containing 25% by mass of a solid and used instead of the aqueous cellooligosaccharide solution of Preparation Example 18. The same procedures as in Preparation Example 18 were repeated to obtain CE-2D. In the saccharide composition of CE-2D, the cellobiose content was 96.3% by mass, the content of cellotriose, cellotetraose, cellopentaose, and cellohexaose combined was 1.7% by mass, and the glucose content was 2.0% by mass.

Preparation Example 20

CE-1D obtained by Preparation Example 18 was used to obtain an aqueous solution containing 25% by mass of a solid and used instead of the aqueous cellooligosaccharide solution of Preparation Example 18. The same procedures as in Preparation Example 18 were repeated to obtain CE-3D. In the saccharide composition of CE-3D, the cellobiose content was 99.1% by mass, and the content of cellotriose, cellotetraose, cellopentaose, and cellohexaose combined was 0.9% by mass. A commercially available glucose (manufactured by Wako Pure Chemical Industries, Ltd., obtained by pulverizing glucose of the special grade) was added to CE-3D at 2.0% by mass relative to the CE-3D content to obtain CE-4D.

Preparation Example 21

A commercially available glucose (manufactured by Wako Pure Chemical Industries, Ltd., obtained by pulverizing glucose of the special grade) was added to CE-1D at 11.5% by mass relative to the total amount of cellobiose, cellotriose, cellotetraose, cellopentaose, and cellohexaose to obtain CE-5D.

Preparation Example 22

An aqueous cellooligosaccharide solution was prepared by the same method as in Preparation Example 17 except that the bacterial strain of Preparation Example 17 was changed to *Cellovibrio gilvus*, pH during culture was not adjusted, and a buffer used for enzymatic reaction was changed phosphate buffer (pH 6.5).

The obtained aqueous cellooligosaccharide solution was allowed to pass through a column filled with active carbon to remove cellobiose-rich fractions, and a cellooligosaccharide powder CE-6D was obtained by the same procedures as in Preparation Example 18. In the saccharide composition of CE-6D, the cellobiose content was 74.5% by mass, the content of cellotriose, cellotetraose, cellopentaose, and cellohexaose combined was 21.8% by mass, and the glucose content was 3.7% by mass.

Examples 19 to 23

CE-1D, -2D, -4D, -5D, and -6D obtained in Preparation Examples 17 to 22 were prepared as aqueous cellooligosaccharide solutions having the composition shown in Table 1 and used to perform the following test.

Transepidermal water loss (TEWL) recovery was tested in 3 male and 2 female subjects (average age 36 years). First, each subject wiped the inner side of the forearm (test site) with 70% ethanol, and the test site was habituated in a room with constant temperature and humidity (room temperature 22° C., humidity 45%) for 15 minutes and measured 3 times with a 2-channel moisture loss monitor manufactured by Asahi Biomed, TW-AS type). The initial TEWL value (TEWL0) was obtained as the average of these values. Then, after measurement of the initial TEWL, the test site was washed with water, the test site was coated with 2% by mass of sodium dodecylsulfate (SDS, by a closed patch using a Finn chamber (manufactured by Epitest) and washed with water, and then TEWL (TEWL rough skir) was measured in the same manner as described above. Then, purified water or the aqueous cellooligosaccharide solution of the present invention was further applied to the same site, and TEWL (TEWL2) at the site was measured by the above-described method 2 hours after the application. Taking the rough skin as 100, relative TEWL values were obtained by the following expression (1). Furthermore, the recovery rate of the transepidermal water loss was obtained by the following expression (2) based on the above-mentioned relative TEWL value. The obtained results are shown in Table 8.

[Expression 1]

$$\text{Relative value} = \frac{TEWL2 - TEWL0}{TWEL \text{ rough skin} - TWEL0} \times 100(\%) \quad (1)$$

$$\text{Recovery-promoting rate } (\%) = \frac{\text{relative water loss from purified water} - \text{relative water loss from aqueous cellooligosaccharide solution}}{\text{relative water loss from purified water}} \times 100(\%) \quad (2)$$

Comparative Example 8

Evaluation was made in the same manner as in Examples 19 to 23 by using purified water containing no saccharide instead of an aqueous cellooligosaccharide solution. The results are shown in Table 8.

Comparative Example 9

Evaluation was made in the same manner as in Examples 19 to 23 by using an aqueous solution of raffinose manufactured by Asahi Kasei Chemicals Corporation, oligo GGF), which has a solid content of 5% with the carbohydrate excluding crystallization water, instead of an aqueous cellooligosaccharide solution. The results are shown in Table 8.

The results in Table 8 show that the relative TEWL values were decreased, and the recovery-promoting rate of transepidermal water loss was increased, that is, the skin barrier function was improved by using the cellooligosaccharide of the present invention.

Furthermore, raffinose had poor relative TEWL against purified water, and the recovery rate was negative.

Examples 24 to 26, Comparative Examples 10 to 13

In Examples 24 to 26 and Comparative Examples 10 and 11, aqueous solutions of cellooligosaccharides and glucose were prepared with the prescription shown in Table 9 (total saccharide concentration 5% by masse) and "greasiness," "smoothness," and browning were evaluated Aqueous solutions comprising 5% by mass of Vaseline and 5% by mass of raffinose were prepared in Comparative Examples 12 and 13, respectively, and evaluated as described above (the relative TEWL value measured in the same manner as in Examples 19 to 23 was 26.4% in Comparative Example 12 and 42.1% in Comparative Example 13).

Evaluation Method

The samples obtained in the Examples and the Comparative Examples were evaluated for 1) greasiness, 2) smoothness, and 3) browning. For evaluation of 1) greasiness and 2) smoothness, the aqueous solutions of Examples 24 to 26 and Comparative Examples 10 to 13 and water were applied to the inner arm of healthy subjects aged 24 to 55 years (6 males, 6 females), and the subjects answered questionnaires with the following evaluation criteria 1) Evaluation Method of "Greasiness"
(Greasiness)
1 point: Greasy
2 points: Slightly greasy
3 points: Neutral
4 points: Slightly ungreasy
5 points: Ungreasy
Evaluations were all made in comparison with water.

2) Evaluation Method of Smoothness
1 point: Poor
2 points: Slightly poor
3 points: Neutral
4 points: Slightly good
5 points: Good
Evaluations were all made in comparison with water.

3) Evaluation Method of Browning
Using the saccharide compositions in Examples 24 to 26 and Comparative Examples 12 and 13 in Table 3, aqueous McIlvaine solutions having a total saccharide concentration of 10% by mass and further containing 0.5% by mass of glycine were prepared at pH 7. The prepared aqueous solutions were heated at 100° C. for 1 hour and cooled to 20° C., and the absorbance at $\lambda=480$ nm was measured.

TABLE 8

| | CELLOOLIGOSACCHARIDE COMPOSITION | | SACCHARIDE CONCENTRATION IN AQUEOUS SOLUTION | | | | |
|---|---|---|---|---|---|---|---|
| | CELLOBIOSE (% BY MASS) | CELLOTRIOSE, CELLOTETRAOSE, CELLLOPENTAOSE, CELLOHEXAOSE (% BY MASS) | CELLOOLIGO-SACCHARIDE (% BY MASS) | GLUCOSE (% BY MASS) | GLUCOSE/ALL SACCHARIDES (% BY MASS) | ABSOLUTE TEWL VALUE AFTER 2 HOURS(%) | TEWL RECOVERY-PROMOTING RATE AFTER 2 HOURS (%) |
| EXAMPLE 19 | 97.3 | 2.7 | 5.0 | 0.130 | 2.5 | 26.1 | 33.6 |
| EXAMPLE 20 | 98.3 | 1.7 | 5.0 | 0.100 | 2.0 | 27.5 | 30.0 |
| EXAMPLE 21 | 99.1 | 0.9 | 5.0 | 0.175 | 3.4 | 28.9 | 26.5 |
| EXAMPLE 22 | 97.3 | 2.7 | 10.0 | 1.300 | 11.5 | 22.4 | 43.0 |
| EXAMPLE 23 | 77.4 | 22.6 | 5.0 | 0.190 | 3.7 | 19.9 | 49.4 |
| COMPARATIVE EXAMPLE 8 | — | — | — | — | — | 39.3 | — |
| COMPARATIVE EXAMPLE 9 | — | — | — | — | — | 42.1 | −7.1 |

TABLE 9

|  |  |  | EXAMPLE 24 | EXAMPLE 25 | EXAMPLE 26 | COMPARATIVE EXAMPLE 10 |
|---|---|---|---|---|---|---|
| SACCHARIDE CONCENTRATION IN AQUEOUS SOLUTION | CELLOBIOSE | % BY MASS | 0.947 | 0.969 | 0.720 | 0.884 |
|  | CELLOTRIOSE, CELLOTETRAOSE, CELLOPENTAOSE AND CELLOHEXAOSE | % BY MASS | 0.027 | 0.012 | 0.264 | 0.018 |
|  | GLUCOSE | % BY MASS | 0.026 | 0.019 | 0.016 | 0.098 |
| SACCHARIDE COMPOSITION IN CELLOOLIGOSACCHARIDE | CELLOBIOSE CONTENT | % BY MASS | 97.2 | 98.8 | 73.2 | 98.0 |
| GLUCOSE/CELLOOLIGOSACCHARIDES RATIO IN AQUEOUS SOLUTION |  | % BY MOLE | 5.1 | 3.7 | 3.1 | 20.6 |
| EVALUATION RESULTS | "GREASINESS"*1 | — | ○ | ○ | ○ | ○ |
|  | "SMOOTHNESS"*2 | — | ○ | ⊚ | ○ | ○ |
|  | BROWNING*3 | — | ○ | ○ | ○ | X |

|  |  |  | COMPARATIVE EXAMPLE 11 | COMPARATIVE EXAMPLE 12 | COMPARATIVE EXAMPLE 13 |
|---|---|---|---|---|---|
| SACCHARIDE CONCENTRATION IN AQUEOUS SOLUTION | CELLOBIOSE | % BY MASS | 0.520 | — | — |
|  | CELLOTRIOSE, CELLOTETRAOSE, CELLOPENTAOSE AND CELLOHEXAOSE | % BY MASS | 0.469 | — | — |
|  | GLUCOSE | % BY MASS | 0.011 | — | — |
| SACCHARIDE COMPOSITION IN CELLOOLIGOSACCHARIDE | CELLOBIOSE CONTENT | % BY MASS | 52.6 | — | — |
| GLUCOSE/CELLOOLIGOSACCHARIDES RATIO IN AQUEOUS SOLUTION |  | % BY MOLE | 2.1 | — | — |
| EVALUATION RESULTS | "GREASINESS"*1 | — | ○ | X | X |
|  | "SMOOTHNESS"*2 | — | X | X | X |
|  | BROWNING*3 | — | ○ | — | — |

*1 As a result of the questionnaire, ○ was given when the average was 3.5 points or higher, and X was given when it was lower than 3.5 points.
*2 As a result of the questionnaire, evalutions were made in the same manner as *1 except that ⊚ was given when the average was 4.0 points or higher.
*3 As a result of browning test, ○ was given when the absorbance was 0.40 or lower, and X was given when it exceeded 0.40.

As shown in Table 9, comparison of Examples 24 to 26 shows that "smoothness" improved with a higher cellobiose content in a cellooligosaccharide. Furthermore, comparison between the Examples and Comparative Example 11 shows that smoothness worsened with increases in the high molecular weight components, i.e., cellotriose, celloterraose, cellopentaose, and cellohexaose, in a cellooligosaccharide. As compared with the Examples for browning, absorbance of the evaluation samples markedly increased, and discoloration of the solution increased in Comparative Example 10. In this evaluation system, no change was observed in "greasiness" regardless of the glucose content.

In comparison between the Examples and Comparative Examples, Vaseline had relative TEWL values comparable to that of a cellooligosaccharide, but a touch such as "greasiness" and "smoothness" was poor. In Comparative Examples 1 to 3, raffinose alone showed a relative TEWL value and a touch not comparable to those of a cellooligosaccharide.

Prescription Example 1

A prescription example of a beauty skin lotion is shown in Table 10 below.

TABLE 10

| No | COMPONENT | MIXTURE RATIO |
|---|---|---|
| 1 | CELLOOLIGOSACCHARIDE | 0.1-40 |
| 2 | AMINOCOAT (MANUFACTURED BY ASAHI KASEI CHEMICALS CORPORATION) | 4.0 |
| 3 | DIPOTASSIUM GLYCYRRHIZINATE | 0.1 |

TABLE 10-continued

| No | COMPONENT | MIXTURE RATIO |
|---|---|---|
| 4 | CONCENTRATED GLYCERIN | 3.0 |
| 5 | SODIUM HYARULONATE | 0.1 |
| 6 | SORBITOL SOLUTION 70% | 2.0 |
| 7 | POLYOXYETHYLENE CETYL ETHER 80% | 0.5 |
| 8 | LIQUID PARAFFIN | 0.6 |
| 9 | SQUALANE | 0.1 |
| 10 | *ALOE* EXTRACT (4) | 2.0 |
| 11 | ROSE WATER | 15.0 |
| 12 | ETHANOL 95% (v/v) | 4.0 |
| 13 | ANTISEPTIC | AS REQUIRED |

* PURIFIED WATER WAS USED TO MAKE THE TOTAL VOLUME 100%.

Prescription Example 2

A prescription example of a white skin lotion is shown in Table 11 below.

TABLE 11

| No | COMPONENT | MIXTURE RATIO |
|---|---|---|
| 1 | CELLOOLIGOSACCHARIDE | 0.1-40 |
| 2 | AMINOCOAT (MANUFACTURED BY ASAHI KASEI CHEMICALS CORPORATION) | 4.0 |
| 3 | DIPOTASSIUM GLYCYRRHIZINATE | 0.1 |
| 4 | CONCENTRATED GLYCERIN | 3.0 |
| 5 | SODIUM HYARULONATE | 0.1 |
| 6 | SORBITOL SOLUTION 70% | 2.0 |
| 7 | POLYOXYETHYLENE CETYL ETHER 80% | 0.5 |

TABLE 11-continued

| No | COMPONENT | MIXTURE RATIO |
|---|---|---|
| 8 | LIQUID PARAFFIN | 0.6 |
| 9 | SQUALANE | 0.1 |
| 10 | ALOE EXTRACT (4) | 2.0 |
| 11 | ROSE WATER | 15.0 |
| 12 | ETHANOL 95% (v/v) | 4.0 |
| 13 | ANTISEPTIC | AS REQUIRED |

*PURIFIED WATER WAS USED TO MAKE THE TOTAL VOLUME 100%.

Prescription Example 3

A prescription example of a skin lotion gel is shown in Table 12 below,

TABLE 12

| No | COMPONENT | MIXTURE RATIO |
|---|---|---|
| 1 | CELLOOLIGOSACCHARIDE | 0.1-40 |
| 2 | AMINOCOAT (MANUFACTURED BY ASAHI KASEI CHEMICALS CORPORATION) | 4.0 |
| 3 | DIPOTASSIUM GLYCYRRHIZINATE | 0.03 |
| 4 | CARBOXYVINYL POLYMER | 0.3 |
| 5 | POTASSIUM HYDROXIDE | 0.03 |
| 6 | TRISODIUM HYDROXYETHYLENEDIAMINE TRIACETATE SOLUTION 40% | 0.02 |
| 7 | 1,3-BUTYLENE GLYCOL | 2.0 |
| 8 | POLYOXYETHYLENE METHYL GLUCOSIDE · 10 EO | 2.0 |
| 9 | CONCENTRATED GLYCERIN | 2.0 |
| 10 | WATER-SOLUBLE PLACENTA EXTRACT | 1.0 |
| 11 | CHAMOMILLA EXTRACT | 0.5 |
| 12 | ETHANOL 95% (v/v) | 5.0 |
| 13 | SODIUM HYARULONATE SOLUTION | |
| 14 | ANTISEPTIC | AS REQUIRED |

*PURIFIED WATER WAS USED TO MAKE THE TOTAL VOLUME 100%.

Prescription Example 4

A prescription example of a body fresh lotion is shown in Table 13 below.

TABLE 13

| No | COMPONENT | MIXTURE RATIO |
|---|---|---|
| 1 | CELLOOLIGOSACCHARIDE | 0.1-40 |
| 2 | AMINOCOAT (MANUFACTURED BY ASAHI KASEI CHEMICALS CORPORATION) | 3.0 |
| 3 | DIPOTASSIUM GLYCYRRHIZINATE | 0.1 |
| 4 | 1,3-BUTYLENE GLYCOL | 1.0 |
| 5 | POLYETHYLENE GLYCOL · 6000 | 2.0 |
| 6 | POLYOXYETHYLENE METHYL GLUCOSIDE · 10 EO | 1.0 |
| 7 | POLYOXYETHYLENE CETYL ETHER · 30 EO | 0.3 |
| 8 | ROSEMARY EXTRACT | 3.0 |
| 9 | ETHANOL 95% (v/v) | 23.0 |
| 10 | ESSENCE (FOR SKIN CARE) | AS REQUIRED |
| 11 | ANTISEPTIC | AS REQUIRED |

*PURIFIED WATER WAS USED TO MAKE THE TOTAL VOLUME 100%.

The cellooligosaccharide of the above-described Prescription Examples 1 to 4 may be added at the same time of the preparation of the above-described prescriptions. The cellooligosaccharide may also be added after mixing components other than the cellooligosaccharide. Other components may be added to a cellooligosaccharide dispersion. Furthermore, for the purpose of improvement of a touch, moisture-retaining property, and the like, the above-described oligosaccharides may be added as required Agent for Improving Indigenous Dermal Bacteria Flora 1 Testing of Staphylococcus epidermis and Staphylococcus aureus (Method of Measuring Change in Bacteria Cell Count)

Cell counts of Staphylococcus epidermis, Staphylococcus aureus, and Pseudomonas aeruginosa were measured by the following method.

First, Staphylococcus epidermis, Staphylococcus aureus, and Pseudomonas aeruginosa were cultured in a nutrient bouillon medium at 35° C. for 24 hours, and the medium was diluted with sterilized distilled water to about $10^7$ cells/mL to obtain a bacteria cell solution for addition. Test substances such as saccharides were dissolved in sterilize distilled water at predetermined concentrations (for example, 1.0%, 0.3%, and 0.1%), 1 mL of the bacterial cell solution for addition was added to 9 mL of each solution, and the mixture was stirred. This test solution was added dropwise to an egg yolk-added mannitol salt agar medium, cultured at 35° C. for 48 hours, and then the bacterial cell count was measured (initial value).

Furthermore, the test solution was maintained at 35° C., and the same procedures were performed at 1 day and 2 days after the preparation to measure the bacterial cell count.

As a blank, the same procedures as described above were performed using sterilized distilled water.

The measured bacterial cell count of the blank and those of the test solutions containing test substances such as saccharides were compared to evaluate the bacteriostatic effect and the bacteria propagating effect of the saccharides against Staphylococcus epidermris, Staphylococcus aureus, and Pseudomonas aeruginosa.

Examples 27 to 32

The saccharide compositions and the saccharide concentrations of the samples subjected to the test as Examples are shown in Table 14.

The results of the tests of these samples for Staphylococcus epidermis and Staphylococcus aureus are shown in Table 15.

Comparative Examples 14 to 16

By the test method in Examples 27 to 32, samples containing maltitol (manufactured by Wako Pure Chemical Industries, Ltd., special-grade reagent) used as a cosmetic raw material having saccharide concentrations of 0.1%, 0.3%, and 1.0% were prepared as Comparative Examples 14, 15, and 16, respectively. The results of the tests conducted similarly using these samples are shown in Table 15.

Comparative examples 17 to 19

By the test method in Examples 27 to 32, samples containing raffinose (manufactured by Wako Pure Chemical Industries, Ltd., special-grade reagent at a concentration of 0.1% 0.3%, and 1.0% were prepared as Comparative Examples 17, 18, and 19, respectively. The results of the tests conducted similarly using these samples are shown in Table 15

Comparative Examples 20 to 22

By the test method in Examples 27 to 32, samples containing isomaltooligosaccharide (manufactured by Wako Pure Chemical Industries, Ltd., special-grade reagent, at a concentration of 0.1%, 0.3%, and 1.0% were prepared as Comparative Examples 20, 21, and 22, respectively. The results of the tests conducted similarly using these samples are shown in Table 15.

Comparative Examples 23 to 25

By the test method in Examples 27 to 32, samples containing glucose (manufactured by Wako Pure Chemical Industries Ltd., special-grade reagent at a concentration of 0.1%, 0.3%, and 1.0% were prepared as Comparative Examples 23, 24, and 25, respectively. The results of the tests conducted similarly using these samples are shown in Table 15.

Comparative Examples 26 to 28

By the test method in Examples 27 to 32, samples containing maltose (manufactured by Wako Pure Chemical Industries, Ltd., special-grade reagent) at a concentration of 0.1%, and 1.0% were prepared as Comparative Examples 26, 27, and 28, respectively. The results of the tests conducted similarly using these samples are shown in Table 15.

TABLE 14

| | GLUCOSE β1,4 LINKED SACCHARIDES COMPOSITION | | TEST BACTERIAL SOLUTION | | |
|---|---|---|---|---|---|
| | CELLOBIOSE (% BY MASS) | CELLOTRIOSE, CELLOTETRAOSE, CELLOPENTAOSE, AND CELLOHEXAOSE (% BY MASS) | GLUCOSE β1,4 LINKED SACCHARIDES CONCENTRATION (% BY MASS) | FREE GLUCOSE CONCENRATION (% BY MASS) | TOTAL SACCHARIDE CONCENTRAION (% BY MASS) |
| EXAMPLE 27 | 97.3 | 2.7 | 0.97 | 0.3 | 0.1 |
| EXAMPLE 28 | 97.3 | 2.7 | 0.97 | 0.3 | 0.3 |
| EXAMPLE 29 | 97.3 | 2.7 | 0.97 | 0.3 | 1.0 |
| EXAMPLE 30 | 65.5 | 35.5 | 0.97 | 0.3 | 0.1 |
| EXAMPLE 31 | 65.5 | 35.5 | 0.97 | 0.3 | 0.3 |
| EXAMPLE 32 | 65.5 | 35.5 | 0.97 | 0.3 | 1.0 |

TABLE 15

| | TYPE OF SACCHARIDE | TOTAL SACCHARIDE CONCENTRATION | CHANGE IN CELL COUNT OF STAPHYLOCOCCUS EPIDERMIS | | CHANGE IN CELL COUNT OF STAPHYLOCOCCUS AUREUS | |
|---|---|---|---|---|---|---|
| | | | INITIAL VALUE | 2 DAYS | INITIAL VALUE | 2 DAYS |
| BLANK | — | — | +++ | +++ | +++ | +++ |
| EXAMPLE 27 | GLUCOSE β1,4 LINKED SACCHARIDES CELLOBIOSE 97.3% | 0.1% | +++ | +++ | +++ | ++ |
| EXAMPLE 28 | | 0.3% | +++ | +++ | +++ | − |
| EXAMPLE 29 | | 1.0% | +++ | +++ | +++ | − |
| EXAMPLE 30 | GLUCOSE β1,4 LINKED SACCHARIDES CELLOBIOSE 65.5% | 0.1% | +++ | +++ | +++ | ++ |
| EXAMPLE 31 | | 0.3% | +++ | +++ | +++ | − |
| EXAMPLE 32 | | 1.0% | +++ | +++ | +++ | − |
| COMPARATIVE EXAMPLE 14 | MALTITOL | 0.1% | +++ | +++ | +++ | +++ |
| COMPARATIVE EXAMPLE 15 | | 0.3% | +++ | +++ | +++ | +++ |
| COMPARATIVE EXAMPLE 16 | | 1.0% | +++ | +++ | +++ | ++++ |
| COMPARATIVE EXAMPLE 17 | RAFFINOSE | 0.1% | +++ | +++ | +++ | +++ |
| COMPARATIVE EXAMPLE 18 | | 0.3% | +++ | +++ | +++ | +++ |
| COMPARATIVE EXAMPLE 19 | | 1.0% | +++ | +++ | +++ | +++ |
| COMPARATIVE EXAMPLE 20 | ISOMALTOOLIGO-SACCHARIDE | 0.1% | +++ | +++ | +++ | +++ |
| COMPARATIVE EXAMPLE 21 | | 0.3% | +++ | ++ | +++ | ++ |
| COMPARATIVE EXAMPLE 22 | | 1.0% | +++ | ++ | +++ | ++ |
| COMPARATIVE EXAMPLE 23 | GLUCOSE | 0.1% | +++ | +++ | +++ | +++ |
| COMPARATIVE EXAMPLE 24 | | 0.3% | +++ | +++ | +++ | +++ |
| COMPARATIVE EXAMPLE 25 | | 1.0% | +++ | +++ | +++ | +++ |
| COMPARATIVE EXAMPLE 26 | MALTOSE | 0.1% | +++ | +++ | +++ | +++ |
| COMPARATIVE EXAMPLE 27 | | 0.3% | +++ | +++ | +++ | +++ |
| COMPARATIVE EXAMPLE 28 | | 1.0% | +++ | +++ | +++ | +++ |

The results of Examples 27 to 32 show that the more potent bacteriostatic action or propagation inhibiting action is exhibited against *Staphylococcus aureus*, a harmful bacterium, with a higher concentration of a water-soluble saccharide containing two or more glucose units linked by a β1,4 glucoside bond. Furthermore, it is shown that no bacteriostatic action is exhibited against *Staphylococcus epidermis*, a skin beneficial bacterium, and the bacterial cell count is maintained.

In Comparative Examples 14 to 20 and 23 to 28, no bacteriostatic action was exhibited against *Staphylococcus epidermis*, a skin beneficial bacterium, or *Staphylococcus aureus*, a harmful bacterium.

In Comparative Examples 21 and 22, a bacteriostatic action or propagation inhibiting action were exhibited against both *Staphylococcus epidermis*, a skin beneficial bacterium, and *Staphylococcus aureus*, a harmful bacterium.

2) Testing of *Pseudomonas aeruginosa*

Subsequently, effects of the samples used in Examples 28, 29, 31, and 32 and Comparative Examples 15 and 16 were tested against *Pseudomonas aeruginosa*. The test results are shown in Table 16. The results of Examples 28, 29, 31, and 32 show that the more potent bacteriostatic action or propagation-inhibiting action is exhibited against *Pseudomonas aeruginosa*, a harmful bacterium with a higher concentration of a water-soluble saccharide containing two or more glucose units linked by a β1,4 glucoside bond.

In Comparative Examples 15 and 16, no bacteriostatic action or propagation inhibiting action was exhibited against *Pseudomonas aeruginosa*, a harmful bacterium.

TABLE 16

| | TYPE OF SACCHARIDE | TOTAL SACCHARIDE CONCENTRATION | CHANGE IN CELL COUNT OF *PSEUDOMONAS AERUGINOSA* | | |
|---|---|---|---|---|---|
| | | | INITIAL VALUE | 6 HOURS | 1 DAYS |
| BLANK | — | — | +++ | +++ | +++ |
| EXAMPLE 28 | CELLOBIOSE | 0.3% | +++ | ++ | + |
| EXAMPLE 29 | 97.3% | 1.0% | +++ | + | − |
| EXAMPLE 31 | CELLOBIOSE | 0.3% | +++ | ++ | + |
| EXAMPLE 32 | 65.5% | 1.0% | +++ | + | − |
| COMPARATIVE EXAMPLE 15 | MALTITOL | 0.3% | +++ | +++ | +++ |
| COMPARATIVE EXAMPLE 16 | | 1.0% | +++ | +++ | +++ |

Testing of Touch of Hair

Subsequently, to evaluate a touch (refreshingness and smoothness) after the hair was coated with the improving agent of the present invention and dried, the samples of the above-mentioned Examples 28 and 31 and Comparative Examples 15, 18, and 24 were tested. The test method is as follows.

The evaluation results are shown in Table 17.

(Test Method)

The hair of healthy subjects aged 28 to 50 years (4 males, 3 females) was uniformly coated with 3 mL of an aqueous solution of the above-mentioned samples and 3 mL of distilled water and dried, and the touch was evaluated. The samples and distilled water were evaluated by the half-head method, and the subjects were not informed of the used test solution beforehand. Furthermore, a questionnaire was conducted using the following evaluation criteria.

(Refreshingness)
1 point: Unrefreshing
2 points: Slightly unrefreshing
3 points: Neutral
4 points: Slightly refreshing
5 points: Refreshing Evaluations were all made in comparison with distilled water.

(Smoothness)
1 point: Poor
2 points: Slightly poor
3 points: Neutral
4 points: Slightly good
5 points: Good Evaluations were all made in comparison with distilled water.

TABLE 17

| | | REFRESH- INGNESS OF DRIED HAIR | SMOOTH- NESS OF DRIED HAIR |
|---|---|---|---|
| EXAMPLE 28 | GLUCOSE β1,4 LINKED SACCHARIDES (CELLOBIOSE 97.3%) | ◎ | ◎ |
| EXAMPLE 31 | GLUCOSE β1,4 LINKED SACCHARIDES (CELLOBIOSE 65.5%) | ○ | ◎ |
| COMPARATIVE EXAMPLE 15 | MALTITOL | ○ | ○ |
| COMPARATIVE EXAMPLE 18 | RAFFINOSE | Δ | ○ |
| COMPARATIVE EXAMPLE 24 | GLUCOSE | X | Δ |

◎: AVERAGE 4.0 POINTS OR HIGHER
Δ: AVERAGE LOWER THAN 3.5 POINTS
○: AVERAGE 3.50 POINTS OR HIGHER
X: AVERAGE LOWER THAN 2.0 POINTS

Table 17 shows that the test solutions comprising water-soluble saccharides containing two or more glucose units linked by a β1,4 glucoside bond can impart refreshingness and smoothness as a hair touch when it is dried. Furthermore, comparison between Examples 28 and 31 shows that refreshingness is improved with a higher the cellobiose content in the cellooligosaccharide.

General Food

Example 33

An acidic sports drink was prepared with the following prescription A using CE-1C as a cellooligosaccharide. Raw materials of the prescription A were mixed beforehand, dissolved in water, and sterilized by heat in an autoclave at 121° C. for 20 minutes to produce the drink experimentally pH 3.2). When the cellooligosaccharide concentration was measured before and after sterilization, the residual rate of the cellooligosaccharide was 99%.

<Prescription A: Acidic Sports Drink>
1) Sucrose 4.0% by mass
2) Citric acid (hydrate, 0.1% by mass
3) Ascorbic acid 0.1% by mass
4) Undiluted grapefruit juice 1.0% by mass
5) Cellooligosaccharide CE-1 10.0% by mass
6) Water 83.8% by mass Example 34

An orange juice was prepared with the following prescription B using CE-1 as a cellooligosaccharide. Raw materials of the prescription B were mixed beforehand, dissolved in water, and sterilized by heat in an autoclave at 121° C. for 20 minutes to produce the drink experimentally (pH 3.2). When the cellooligosaccharide concentration was measured before and after sterilization, the residual rate of the cellooligosaccharide was 99%.

Prescription B: Orange Juice

1), Sucrose 7.5% by mass
2, Citric acid hydrate 0.1% by mass
4) 4 times concenrated orange juice 5.0% by mass
5) cellooligosaccharide CE-1 10.0% by mass
6) Water 76.9% by mass Example 35

2.0 parts of a commercially available gelatin was added to 98 parts of orange juice obtained in Example 34 and dissolved at 90° C. with stirring. After dissolution, the mixture was sealed in a 100-mL plastic container and stored at 5° C. for 18 hours to produce a cellooligosaccharide containing jelly. The cellooligosaccharide was uniformly dispersed, and 99% or higher thereof remained after this procedure.

Example 36

A cellooligosaccharide containing agar was produced using a commercially available agar instead of gelatin in the method of Example 35. The cellooligosaccharide was uniformly dispersed, and 99% or higher thereof remained after this procedure.

Example 37

A baked confectionery was produced experimentally with the following prescription C using CE-1C as a cellooligosaccharide.

Prescription C: Baked Confectionery

1) Flour 50.8 parts by mass
2) Sodium hydrogen carbonate 0.93 parts by mass
3) Margarin 23.1 parts by mass
4) Sugar 10.4 parts by mass
5) Sodium chloride 0.46 parts by mass
6) Whole egg 4.63 parts by mass
7) Cellooligosaccharide 5.0 parts by mass
8) Water 4.63 parts by mass Powder components except margarine, whole egg, and water were weighed in a plastic bag and mixed for 3 minutes. Margarine, whole egg, and water were added to the mixed powder, and the mixture was introduced into a planetary mixer. A hook wing was used in the planetary mixer to knead the mixture at 126 rpm for 2 minutes.

The dough obtained by kneading was placed in a 100-mL plastic container and stored at 5° C. for 2 days. When the dough was observed 2 days later, oil did not soak out at room temperature. Furthermore, the indentation load of the dough measured with a rheometer (manufactured by Fudow Corporation) was 1.2 kg/cm$^2$, and the tensile load was 0.31 kg/cm$^2$ (all are an average of 10 values).

The above-mentioned dough was molded into a rectangular solid of 3 cm×1.5 cm×1.5 cm (base area=4.5 cm$^2$) and heated in an oven at 160° C. for 20 minutes. Even after heating, 60% or higher of the cellooligosaccharide remained. Furthermore, the change of the shape was small after heating, with the base area expansion rate being lower than 50% (all are average of 10 values).

Comparative Example 29

A baked confectionery was produced in the same manner as in Example 37 except that the cellooligosaccharide in the prescription C of Example 37 was replaced with sucrose. As a result of observation of the dough in the same manner as in Example 37, oil soaking out was observed on the surface. Furthermore, the indentation load of the dough was 0.8 kg/cm$^2$, and the tensile load was 0.24 kg/cm$^2$. With this system containing no cellooligosaccharide, oil soaking out was not suppressed, and the indentation and tensile loads of the dough were small.

Furthermore, the confectionery was molded in the same manner as in Example 37 and then heated in an oven. The base area expansion rate of the baked confectionery after heating was 50% or higher, and the change in the shape due to heating was greater as compared with the cellooligosaccharide-added group.

INDUSTRIAL APPLICABILITY

Since the cellooligosaccharide composition of the present invention or the cellooligosaccharide powder comprising the composition of the present invention is excellent in oil retention in addition to powder fluidity and uniform dispersibility; hardly absorbs moisture; and has excellent handling properties such as compression moldability, heat resistance, acid resistance, a property of preventing starch retrogration, and a property of preventing protein modification, it can be utilized in the fields of foods, cosmetics, drugs, and quasi-drugs as a high fluidity cellooligosaccharide powder. Furthermore, a composition containing the same can be utilized as a food, a cosmetic, a drug, or a quasi-drug that does not suffer from agglutination of cellooligosaccharides, has improved dispersivity and excellent compression moldability, heat resistance, and acid resistance, in which starch retrogradation and protein modification are prevented.

In the fields of foods and drugs, the cellooligosaccharide composition of present invention can be utilized as an internal medicine which is an agent for preventing or improving a lifestyle-related disease, since a decrease of blood adiponectin concentration is suppressed by regulating the saccharide composition, and the neutral fat and total cholesterol concentrations in the liver are decreased by oral intake thereof.

Since the cellooligosaccharide composition of the present invention is not assimilated by harmful intestinal bacteria and selectively activates useful bacteria, it can be utilize as an agent for activating enteric bacteria.

Since the cellooligosaccharide composition of the present invention suppresses propagation of *Helicobacter pylori* or exhibits a bacteriostatic effect against *Helicobacter pylori*, it can be utilized as an agent for suppressing *Helicobacter pylori* propagation or bacteriostatic agent against *Helicobacter pylori*.

Particularly in the fields of cosmetics, drugs, and quasi-drugs, the cellooligosaccharide composition of the present invention can be utilized as a topical agent that is excellent in a moistening effect and improves the damaged skin such as rough skin, sensitive skin, and dry skin, as an agent for improving skin barrier function that promotes the recovery of the transepidermal water loss; has favorable usability; and is excellent in handling property, or as an agent for improving indigenous dermal bacteria flora that is not assimilated by harmful epidermal bacteria and selectively activates useful bacteria.

The invention claimed is:

1. A cellooligosaccharide composition, which comprises, as a principal ingredient, a cellooligosaccharide comprising cellobiose and one or more selected from the group consisting of cellotriose, cellotetraose, cellopentaose, and cellohexaose and is a powder having an average L/D of 3.0 or lower, a bulk density of 0.80 g/mL or lower, and a repose angle of 60° or smaller.

2. The cellooligosaccharide composition according to claim 1, wherein the average L/D is 2.5 or lower, and the bulk density is 0.55 g/mL or lower.

3. The cellooligosaccharide composition according to claim 1, wherein the repose angle is 45° or smaller.

4. The cellooligosaccharide composition according to claim 1, wherein the amount of oil retention is 0.9 g/g or more.

5. The cellooligosaccharide composition according to claim 1, wherein the moisture absorption rate after allowed to stand in an environment with a relative humidity of 75% and a temperature of 40° C. for 18 hours is 1% by mass or lower.

6. The cellooligosaccharide composition according to claim 1, wherein a mold formed from 200 mg of the composition by compression with 10 kN using a mortar and a pestle with circular flat surfaces of φ8.0 mm has a hardness of 60 N or higher.

7. The cellooligosaccharide composition according to claim 1, wherein the cellooligosaccharide residual rate is 90% or higher after heat treatment at 100° C. or higher and pH 7 or lower for 10 minutes or longer.

8. The cellooligosaccharide composition according to claim 1, wherein the cellobiose content is 70% by mass or higher, and the content of one or more selected from the group consisting of cellotriose, cellotetraose, cellopentaose, and cellohexaose is 0 to 30% by mass.

9. The cellooligosaccharide composition according to claim 8, which contains 9% by mass or lower of glucose relative to the cellooligosaccharides.

10. The cellooligosaccharide composition according to claim 9, wherein the cellobiose content is 90% by mass or higher, the content of one or more selected from the group consisting of cellotriose, cellotetraose, cellopentaose, and cellohexaose is 0.1 to 10% by mass, and the glucose content is 3.5% by mass or lower.

11. The cellooligosaccharide composition according to claim 10, wherein the cellobiose content is 95% by mass or higher, the content of one or more selected from the group consisting of cellotriose, cellotetraose, cellopentaose, and cellohexaose is 0.5 to 5% by mass.

12. The cellooligosaccharide composition according to claim 11, wherein the glucose content is 2% by mass or lower.

13. A cellooligosaccharide-containing composition, which comprises a cellooligosaccharide composition according to claim 1 as an active ingredient in which the cellobiose content is 50% by mass or higher, the content of one or more selected from the group consisting of cellotriose, cellotetraose, cellopentaose, and cellohexaose is 0 to 50% by mass, wherein the cellooligosaccharides are dispersed or dissolved in water or a mixed solution of water/organic solvent, and is used for any one or more of the following purposes (i) to (ix):

(i) an agent for preventing or improving a lifestyle-related disease, which suppresses the decreasing rate of a blood adiponectin concentration to 30% or lower by oral intake thereof;

(ii) an agent for activating enteric bacteria flora, which has a property of activating enteric bacteria flora by being assimilated by useful intestinal bacteria and not being assimilated by harmful intestinal bacteria, propagates one or more bacteria selected from the group consisting of *Bifidobacterium adolescentis*, *Bifidobacterium breve*, *Lactobacillus acidophilus*, *Lactobacillus casei*, and *Lactobacillus gasseri* as useful intestinal bacteria, and suppresses propagation of *Bacteroides fragilis* or *Eubacterium aerofaciens* as harmful intestinal bacteria;

(iii) an agent for activating enteric bacteria flora, which has a property of activating enteric bacteria flora by being assimilated by useful intestinal bacteria and not being assimilated by harmful intestinal bacteria and suppresses propagation of *Clostridium perfringens* as a harmful intestinal bacterium;

(iv) an agent for suppressing *Helicobacter pylori* propagation or a bacteriostatic agent against *Helicobacter pylori*, which has a suppressing rate of *Helicobacter pylori* propagation of 1% or higher;

(v) a bone calcium concentration enhancer, which has an increasing rate of calcium concentration in the thigh bone of 5% or higher by oral intake together with calcium;

(vi) an agent for improving skin barrier function, which has a recovery-promoting rate of transepidermal water loss of 10% or higher by application to the skin;

(vii) an agent for improving indigenous dermal bacteria flora, wherein the active ingredient does not exhibit a bacteriostatic effect against *Staphylococcus epidermidis* but exhibits a bacteriostatic effect against *Staphylococcus aureus* and *Pseudomonas aeruginosa;*

(viii) an agent for preventing starch retrogradation, which has a starch retrogradation rate of 20% or lower after stored in the coexistence with starch; and (ix) an agent for preventing protein modification, which has a protein modification rate of 10% or lower after stored in the coexistence with a protein.

14. A cellooligosaccharide-containing composition used as an agent for preventing or improving a lifestyle-related disease, which comprises the cellooligosaccharide composition according to claim 1 as an active ingredient and suppresses a decrease in a blood adiponectin concentration to 30% or lower by oral intake thereof.

15. The cellooligosaccharide-containing composition according to claim 13, wherein the decreasing rate of a neutral fat concentration in the liver by oral intake thereof is 15% or higher.

16. The cellooligosaccharide-containing composition according to claim 13, wherein the cellooligosaccharide composition surpresses the decreasing rate of a blood adiponectin concentration to 25% or lower by oral intake thereof.

17. A method of propagating one or more enteric bacteria selected from the group consisting of *Bifidobacterium adolescentis, Bifidobacterium breve, Lactobacillus acidophilus, Lactobacillus casei*, and *Lactobacillus gasseri*, and suppressing propagation of *Bacteroides fragilis* or *Eubacterium aerofaciens* in a subject in need thereof, which comprises administering the celloligosaccharide composition according to claim 1 to the subject.

18. A method of activating enteric bacteria flora, and suppressing propagation of *Clostridium perfringens* in a subject in need thereof, which comprises administering the celloligosaccharide composition according to claim 1 to the subject.

19. A method of suppressing *Helicobacter pylori* propagation in a subject in need thereof, which comprises administering the cellooligosaccharide composition according to claim 1 to the subject.

20. A method of enhancing bone calcium concentration in a subject in need thereof, which comprises administering the cellooligosaccharide composition according to claim 1 to the subject.

21. A method of improving skin barrier function in a subject in need thereof, which comprises administering the cellooligosaccharide composition according to claim 1 to the subject.

22. A method of improving indigenous dermal bacteria flora in a subject in need thereof, which comprises administering the cellooligosaccharide composition according to claim 1 to the subject in an amount sufficient to not exhibit a bacteriostatic effect against *Staphylococcus epidermidis* but exhibit a bacteriostatic effect against *Staphylococcus aureus* and *Pseudomonas aeruginosa*.

23. A method of preventing starch retrogradation, which comprises storing the cellooligosaccharide composition according to claim 1 in the coexistence with starch.

24. A method of preventing protein modification, which comprises storing the cellooligosaccharide composition according to claim 1 in the coexistence with a protein.

25. The cellooligosaccharide-containing composition according to claim 14, wherein the cellooligosaccharide composition is contained in one or more components selected from food materials, cosmetic materials, medicinal components of drugs or additives used therein, and is in the form of granule, mold, aqueous solution, water dispersion, paste, or gel.

26. The cellooligosaccharide-containing composition according to claim 25, wherein the cellooligosaccharide-containing composition in the form of aqueous solution, water dispersion, paste, or gel contains any one or more of surfactants, thickening agents, or gelatinizing agents.

27. A cellooligosaccharide-containing food, which comprises the cellooligosaccharide-containing composition according to claim 25.

28. A cellooligosaccharide-containing cosmetic, which comprises the cellooligosaccharide-containing composition according to claim 25.

29. A cellooligosaccharide-containing drug, which comprises the cellooligosaccharide-containing composition according to claim 25.

30. A cellooligosaccharide-containing quasi-drug, which comprises the cellooligosaccharide-containing composition according to claim 25.

* * * * *